United States Patent
Bigot et al.

(10) Patent No.: US 7,232,833 B2
(45) Date of Patent: Jun. 19, 2007

(54) 4-SUBSTITUTED QUINOLINE DERIVATIVES, METHOD AND INTERMEDIATES FOR THEIR PREPARATION AND PHARMACEUTICAL COMPOSITIONS CONTAINING THEM

(75) Inventors: Antony Bigot, Massy (FR); Youssef El-Ahmad, Creteil (FR); Jean-Luc Malleron, Marcoussis (FR); Jean-Paul Martin, Colombes (FR); Serge Mignani, Chatenay Malabry (FR); Guy Pantel, La Queue en Brie (FR); Baptiste Ronan, Clamart (FR); Michel Tabart, La Norville (FR); Michel Cheve, Soisy sur Seine (FR); Fabrice Viviani, Louvre (FR)

(73) Assignee: Novexel, Romainville (FR)

(*) Notice: Subject to any disclaimer, the term of this patent is extended or adjusted under 35 U.S.C. 154(b) by 482 days.

(21) Appl. No.: 10/810,711

(22) Filed: Mar. 26, 2004

(65) Prior Publication Data
US 2004/0224946 A1    Nov. 11, 2004

Related U.S. Application Data

(60) Provisional application No. 60/487,084, filed on Jul. 14, 2003.

(30) Foreign Application Priority Data

Mar. 28, 2003   (FR) .................................. 03 03812

(51) Int. Cl.
A61K 31/47    (2006.01)
A61K 31/517   (2006.01)
A61K 31/44    (2006.01)
A61K 31/50    (2006.01)
A61K 31/54    (2006.01)

(52) U.S. Cl. ............... 514/314; 514/266.1; 514/303; 514/249; 514/235.2; 546/122; 546/174; 544/128; 544/235; 544/284

(58) Field of Classification Search ............... 546/174, 546/122; 514/314, 235.2, 249, 266.1, 303; 544/128, 235, 284
See application file for complete search history.

(56) References Cited

U.S. PATENT DOCUMENTS
2004/0147518 A1    7/2004   Bacque et al.

FOREIGN PATENT DOCUMENTS
FR    2816618       5/2002
WO    WO 01/07432   2/2001

Primary Examiner—Bernard Dentz
Assistant Examiner—Binta Robinson
(74) Attorney, Agent, or Firm—Harness, Dickey & Pierce, P.L.C.

(57) ABSTRACT

The invention relates to 4-substituted quinoline compounds of general formula:

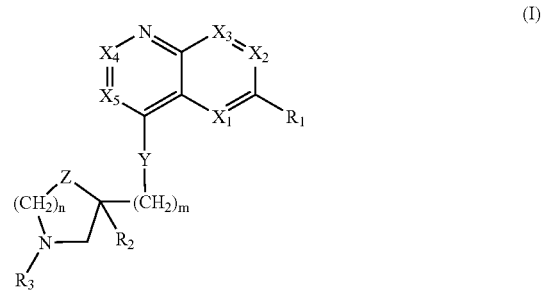

which are active as antimicrobials, in which:
$X_1$, $X_2$, $X_3$, $X_4$ and $X_5$ is C—$R'_1$, to C—$R'_5$ respectively, or alternatively at most one represents N,
Y represents CHR, CO, CROH, CRNH$_2$, CRF or CF$_2$, R being a hydrogen or alkyl, m is 1, 2 or 3 and n is 0, 1 or 2, Z is CH$_2$ or Z is O, S, SO, SO$_2$ and, in this case, n is equal to 2, $R_2$ is —CO$_2$R, —CH$_2$CO$_2$R, —CH$_2$—CH$_2$CO$_2$R, —CH$_2$OH or —CH$_2$—CH$_2$OH,
wherein R is as defined above,
$R_3$ represents phenyl, heteroaryl or alk-$R°_3$, where alk is alkyl and $R°_3$ represents various groups, where appropriate containing oxygen, sulfur or amine, in their enantiomeric or diastereoisomeric forms or their mixtures, and/or where appropriate in the syn or anti form or their mixtures, and their salts.

16 Claims, No Drawings

4-SUBSTITUTED QUINOLINE DERIVATIVES, METHOD AND INTERMEDIATES FOR THEIR PREPARATION AND PHARMACEUTICAL COMPOSITIONS CONTAINING THEM

This application claims the benefit of U.S. Provisional Application No. 60/487,084 filed Jul. 14, 2003 and right of priority from French Patent Application No. 03 03812, filed Mar. 28, 2003.

The present invention relates to 4-substituted quinoline derivatives of general formula:

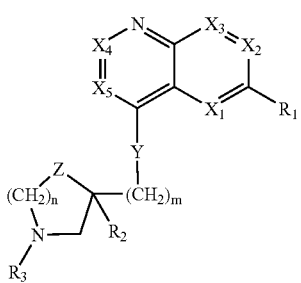
(I)

which are active as antimicrobials. The invention also relates to the method and intermediates for their preparation and the pharmaceutical compositions containing them.

In patent applications WO 99/37635 and WO 00/43383 have been described antimicrobial quinolylpropylpiperidine derivatives of general formula:

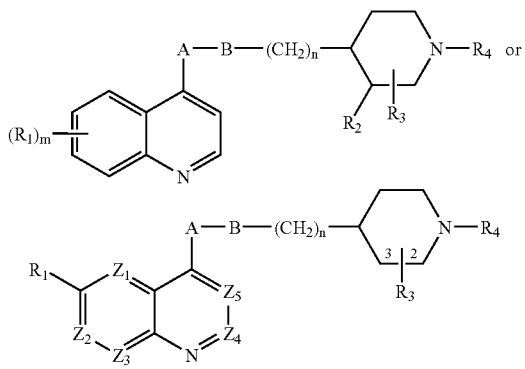

in which the radical $R_1$ is in particular alkoxy (C1–6), $R_2$ is hydrogen, $R_3$ is at the 2 or 3 position and represents alkyl (C1–6) which may be optionally substituted with 1 to 3 substituents chosen from thiol, halogen, alkylthio, trifluoromethyl, carboxy, alkyloxycarbonyl, alkylcarbonyl, alkenyloxycarbonyl, alkenylcarbonyl, hydroxyl optionally substituted with alkyl, $R_4$ is a group —$CH_2$—$R_5$ for which $R_5$ is selected from alkyl, hydroxyalkyl, alkenyl, alkynyl, tetrahydrofuryl, optionally substituted phenylalkyl, optionally substituted phenylalkenyl, optionally substituted heteroarylalkyl, optionally substituted heteroaroyl . . . , n is 0 to 2, m is 1 or 2 and A and B are in particular oxygen, sulfur, sulfinyl, sulfonyl, $NR_{11}$, $CR_6R_7$ for which $R_6$ and $R_7$ represent H, thiol, alkylthio, halo, trifluoromethyl, alkenyl, alkenylcarbonyl, hydroxyl, amino, and $Z_1$ to $Z_5$ are N or $CR_{1a}$ . . .

Other applications, in particular WO 00/21952, WO 00/21948, WO 01/07432, WO 01/07433, WO 03/010138, or alternatively WO 02/40474 or WO 02/072572 describe other 4-(quinolylpropyl)piperidine derivatives, substituted in particular at the 3 position or disubstituted at the 4 position, which are active in the same field. European application EP 30044 moreover describes related derivatives which are active in the cardiovascular field.

No derivative of this nature, in which the piperidine ring has been modified as in those of formula (I) above, has been described to date.

It has now been found, and that is what constitutes the subject of the present invention, that the compounds of general formula (I) in which:

$X_1$, $X_2$, $X_3$, $X_4$ and $X_5$ represent >C—$R'_1$ to >C—$R'_5$ respectively, or alternatively at most one of them represents a nitrogen atom, $R_1$, $R'_1$, $R'_2$, $R'_3$, $R'_4$ and $R'_5$ are identical or different and represent a hydrogen or halogen atom or an alkyl, cycloalkyl, phenyl, phenylthio, mono- or bicyclic heteroaryl or heteroarylthio, OH, SH, alkyloxy, difluoromethoxy, trifluoromethoxy, alkylthio, trifluoromethylthio, cycloalkyloxy, cycloalkylthio, acyl, acyloxy, acylthio, cyano, carboxyl, alkyloxycarbonyl, cycloalkyloxycarbonyl, nitro, —NRaRb or —CONRaRb radical (for which Ra and Rb can represent hydrogen, alkyl, cycloalkyl, phenyl, mono- or bicyclic heteroaryl or Ra and Rb form together with the nitrogen atom to which they are attached a 5- or 6-membered heterocycle which may optionally contain another heteroatom chosen from O, S or N and carrying, where appropriate, an alkyl, phenyl or mono- or bicyclic heteroaryl substituent on the nitrogen atom or, where appropriate, in which the sulfur atom is oxidized to the sulfinyl or sulfonyl state), or represent a methylene radical substituted with fluoro, hydroxyl, alkyloxy, alkylthio, cycloalkyloxy, cycloalkylthio, phenyl, mono- or bicyclic heteroaryl, carboxyl, alkyloxycarbonyl, cycloalkyloxycarbonyl, —NRaRb or —CONRaRb for which Ra and Rb are as defined above, or represent phenoxy, heterocyclyloxy, benzyloxy, heterocyclylmethyloxy, or alternatively $R_1$ may also represent difluoromethoxy, or a radical having the structure —$C_mF_{2m+1}$, —$SC_mF_{2m+1}$ or —$OC_mF_{2m+1}$ for which m is an integer from 1 to 6 or alternatively $R'_5$ may also represent trifluoroacetyl, m is equal to 1, 2 or 3;

n is equal to 0, 1 or 2;

Y represents a group CHR, CO, CROH, $CRNH_2$, CRF or $CF_2$, R being a hydrogen atom or an alkyl ($C_{1-6}$) radical;

Z represents a $CH_2$ group or alternatively Z represents an oxygen atom, a sulfur atom, or an SO group or an $SO_2$ group and, in this case, n is equal to 2;

$R_2$ represents a radical —$CO_2R$, —$CH_2CO_2R$, —$CH_2$—$CH_2CO_2R$, —$CH_2OH$ or —$CH_2$—$CH_2OH$, R being as defined above;

$R_3$ represents a radical phenyl, mono- or bicyclic heteroaryl, alk-$R°_3$ for which alk is an alkylene radical and $R°_3$ represents hydrogen, halogen, hydroxyl, alkyloxy, alkylthio, alkylsulfinyl, alkylsulfonyl, alkylamino, dialkylamino, cycloalkyl, cycloalkyloxy, cycloalkylthio, cycloalkylsulfinyl, cycloalkylsulfonyl, cycloalkylamino, N-cycloalkyl-N-alkylamino, —N-(cycloalkyl)$_2$, acyl, cycloalkylcarbonyl, phenyl, phenoxy, phenylthio, phenylsulfinyl, phenylsulfonyl, phenylamino, N-alkyl-N-phenylamino, N-cycloalkyl-N-phenylamino, —N-(phenyl)$_2$, phenylalkyloxy, phenylalkylthio, phenylalkylsulfinyl, phenylalkylsulfonyl, phenylalkylamino, N-alkyl-N-phenylaminoalkyl, N-cyclo-alkyl-N-phenylalkylamino, benzoyl, mono- or bicyclic heteroaryl, heteroaryloxy, heteroarylthio, heteroarylsulfinyl, heteroarylsulfonyl, heteroarylamino, N-alkyl-N-heteroarylamino, N-cycloalkyl-N-heteroarylamino, heteroarylcarbonyl, heteroarylalkyloxy, heteroarylalkylthio, heteroarylalkylsulfinyl, heteroarylalkyl-sulfonyl, heteroarylalkylamino, N-alkyl-N-heteroarylaminoalkyl, N-cycloalkyl-N-heteroarylaminoalkyl, (the heteroaryl parts mentioned above being mono- or bicyclic), carboxyl, alkyloxycarbonyl, —NRaRb or —CO—NRaRb for which Ra and Rb respectively represent hydrogen, alkyl, cycloalkyl, phenyl, mono- or bicyclic heteroaryl, or one of Ra or Rb represents hydroxyl, alkyloxy, cycloalkyloxy, or Ra and Rb form together with the nitrogen atom to which they are attached a 5- or 6-membered heterocycle which may optionally contain another heteroatom chosen from O, S and N and carrying, where appropriate, an alkyl, phenyl or mono- or bicyclic heteroaryl substituent on the nitrogen atom or, where appropriate, in which the sulfur atom is oxidized to the sulfinyl or sulfonyl state), or alternatively $R^{o}_{3}$ represents —CR'b═CR'c-R'a for which R'a represents phenyl, phenylalkyl, heteroaryl or heteroarylalkyl in which the heteroaryl part is mono- or bicyclic, phenoxyalkyl, phenylthioalkyl, phenylsulfinylalkyl, phenylsulfonylalkyl, phenylaminoalkyl, N-alkyl-N-phenylaminoalkyl, heteroaryloxyalkyl, heteroarylthioalkyl, heteroarylsulfinyl, heteroarylsulfonylalkyl, heteroarylaminoalkyl, N-alkyl-N-heteroarylaminoalkyl, heteroarylthio, heteroarylsulfinyl, heteroarylsulfonyl, (the heteroaryl parts mentioned above being mono- or bicyclic), phenylthio, phenylsulfinyl, phenylsulfonyl, and for which R'b and R'c represent hydrogen, alkyl or cycloalkyl, or alternatively $R^{o}_{3}$ represents a radical —C≡C-Rd for which Rd is alkyl, phenyl, phenylalkyl, phenoxyalkyl, phenylthioalkyl, N-alkyl-N-phenylaminoalkyl, mono- or bicyclic heteroaryl, heteroarylalkyl, heteroaryloxyalkyl, heteroarylthioalkyl, heteroarylaminoalkyl, N-alkyl-N-heteroarylaminoalkyl, (the heteroaryl parts mentioned above being mono- or bicyclic aromatic), or alternatively $R^{o}_{3}$ represents a radical —CF$_2$-phenyl or mono- or bicyclic —CF$_2$-heteroaryl, it being understood that the phenyl, benzyl, benzoyl or heteroaryl radicals or portions mentioned above are optionally substituted on the ring with 1 to 4 substituents chosen from halogen, hydroxyl, alkyl, alkyloxy, alkyloxyalkyl, haloalkyl, trifluoromethyl, trifluoromethoxy, trifluoromethylthio, carboxyl, alkyloxycarbonyl, cyano, alkylamino, —NRaRb for which Ra and Rb are as defined above, phenyl, hydroxyalkyl, alkylthioalkyl, alkylsulfinylalkyl, alkylsulfonylalkyl, it being understood that the alkyl or acyl radicals and portions contain (unless specifically stated) 1 to 10 carbon atoms in the form of a straight or branched chain and that the cycloalkyl radicals contain 3 to 6 carbon atoms, in their enantiomeric or diastereoisomeric forms or mixtures of these forms, and/or where appropriate in syn or anti form or mixtures thereof, and their salts, are very potent antibacterial agents.

It is understood that when the radicals represent or carry a halogen atom, the latter is chosen from fluorine, chlorine, bromine and iodine, and is preferably fluorine.

In the above general formula, when the radicals represent or carry a mono- or bicyclic heteroaryl substituent, the latter contains 5 to 10 members and may be chosen (without limitation) from thienyl, furyl, pyrrolyl, imidazolyl, thiazolyl, oxazolyl, thiadiazolyl, oxadiazolyl, tetrazolyl, pyridyl, pyridazinyl, pyrazinyl, pyrimidinyl, indolyl, benzothienyl, benzofuranyl, indazolyl, benzothiazolyl, naphthyridinyl, quinolyl, isoquinolyl, cinnolyl, quinazolyl, quinoxalyl, benzoxazolyl and benzimidazolyl which are optionally substituted with the substituents listed above.

Among the compounds of general formula (I), there may be mentioned in particular those in which $X_1$, $X_2$, $X_3$, $X_4$ and $X_5$ are as defined above, $R_1$, $R'_1$, $R'_2$, $R'_3$, $R'_4$ and $R'_5$, which are identical or different, represent a hydrogen or halogen atom, an alkyl or alkyloxy radical, or a methylene radical substituted with alkyloxy:

Y represents a radical CH$_2$, CHOH, CHF, CHNH$_2$ or C═O;
m is equal to 1;
n is as defined above;
Z is a CH$_2$ group or an oxygen atom and in the latter case, n is equal to 2;
$R_2$ is as defined above, and
$R_3$ represents a radical alk-$R^{o}_{3}$ for which alk is an alkylene radical and $R^{o}_{3}$ represents alkyloxy, alkylthio, alkylamino, dialkylamino, cycloalkyloxy, cycloalkylthio, cycloalkylamino, N-cycloalkyl-N-alkylamino, —N-(cycloalkyl)$_2$, phenoxy, phenylthio, phenylamino, N-alkyl-N-phenylamino, N-cycloalkyl-N-phenylamino, phenylalkyloxy, phenylalkylthio, phenylalkylamino, N-alkyl-N-phenylaminoalkyl, N-cycloalkyl-N-phenylalkylamino, heteroaryloxy, heteroarylthio, heteroarylamino, N-alkyl-N-heteroarylamino, N-cycloalkyl-N-heteroarylamino, heteroarylcarbonyl, heteroarylalkyloxy, heteroarylalkylthio, heteroarylalkylamino, N-alkyl-N-heteroarylaminoalkyl, N-cycloalkyl-N-heteroarylaminoalkyl, (the heteroaryl parts cited above being mono- or bicyclic), —NRaRb or —CO—NRaRb for which Ra and Rb are as defined above, or alternatively $R^{o}_{3}$ represents —CR'b═CR'c-R'a for which R'a represents phenyl, phenylalkyl, heteroaryl or heteroarylalkyl, phenoxyalkyl, phenylthioalkyl, phenylaminoalkyl, N-alkyl-N-phenylaminoalkyl, heteroaryloxyalkyl, heteroarylthioalkyl, heteroarylaminoalkyl, N-alkyl-N-heteroarylaminoalkyl, heteroarylthio, (the heteroaryl parts mentioned above being mono- or bicyclic), or phenylthio, and for which R'b and R'c represent hydrogen, alkyl or cycloalkyl, or alternatively $R^{o}_{3}$ represents a radical —C≡C-Rd for which Rd is alkyl, phenyl, phenylalkyl, phenoxyalkyl, phenylthioalkyl, N-alkyl-N-phenylaminoalkyl, heteroaryl, heteroarylalkyl, heteroaryloxyalkyl, heteroarylthioalkyl, heteroarylaminoalkyl, N-alkyl-N-heteroarylaminoalkyl, (the heteroaryl parts mentioned above being mono- or bicyclic), or alternatively $R^{o}_{3}$ represents a —CF$_2$-phenyl or mono- or bicyclic —CF$_2$-heteroaryl radical, it being understood that the phenyl, benzyl, benzoyl or heteroaryl radicals or portions mentioned above are optionally substituted as envisaged above, in their enantiomeric or diastereoisomeric forms or mixtures of these forms, and/or where appropriate in syn or anti form or mixtures thereof, and their salts, and more particularly those in which $X_1$, $X_2$, $X_3$, $X_4$ and $X_5$ represent >C—$R'_1$ to >C—$R'_5$ respectively,
$R_1$, $R'_1$, $R'_2$, $R'_3$, $R'_4$ and $R'_5$, which are identical or different, represent a hydrogen or halogen atom or an alkyl or alkyloxy radical, or a methylene radical substituted with alkyloxy;
Y represents a radical CH$_2$, CHOH, CHF, CHNH$_2$ or C═O;
m is equal to 1;
n is as defined above;

Z is a CH$_2$ group or an oxygen atom and in the latter case, n is equal to 2;

R$_2$ is as defined above, and

R$_3$ represents a radical alk-R°$_3$ for which alk is an alkylene radical and R°$_3$ represents cycloalkyloxy, cycloalkylthio, phenoxy, phenylthio, phenylalkyloxy, phenylalkylthio, heteroaryloxy, heteroarylthio, heteroarylalkyloxy, heteroarylalkylthio, (the heteroaryl parts mentioned above being mono- or bicyclic) or alternatively R$_3$ represents —CR'b=CR'c-R'a for which R'a represents phenyl, phenylalkyl, heteroaryl, heteroarylalkyl, phenoxyalkyl, phenylthioalkyl, heteroaryloxyalkyl, heteroarylthioalkyl, heteroarylthio (the heteroaryl parts mentioned above being mono- or bicyclic), or phenylthio, and for which R'b and R'c represent hydrogen, alkyl or cycloalkyl, or alternatively R°$_3$ represents a radical —C≡C-Rd for which Rd is alkyl, phenyl, phenylalkyl, phenoxyalkyl, phenylthioalkyl, N-alkyl-N-phenylaminoalkyl, mono- or bicyclic heteroaryl, heteroarylalkyl, heteroaryloxyalkyl, heteroarylthioalkyl, the heteroaryl parts mentioned above being mono- or bicyclic, it being understood that the phenyl, benzyl, benzoyl or heteroaryl radicals or portions mentioned above are optionally substituted as envisaged above, in their enantiomeric or diastereoisomeric forms or mixtures of these forms, and/or where appropriate in syn or anti form or mixtures thereof, and their salts.

Among the compounds of general formula (I), the subject of the invention is most particularly any one of those whose names follow:

1-[(2E)-3-(2,5-difluorophenyl)-2-propenyl]-3-[3-(3-fluoro-6-methoxyquinolin-4-yl)propyl]-3-pyrrolidinecarboxylic acid;

1-[(2E)-3-(2,5-difluorophenyl)-2-propenyl]-3-[3-hydroxy-(3-fluoro-6-methoxyquinolin-4-yl)propyl]-3-pyrrolidinecarboxylic acid;

1-[2-(2,5-difluorophenylsulfanyl)ethyl]-3-[3-(3-fluoro-6-methoxyquinolin-4-yl)propyl]-3-pyrrolidinecarboxylic acid;

1-[2-(2,5-difluorophenyloxy)ethyl]-3-[3-(3-fluoro-6-methoxyquinolin-4-yl)propyl]-3-pyrrolidinecarboxylic acid;

1-[2-(thiophen-2-ylsulfanyl)ethyl]-3-[3-(3-fluoro-6-methoxyquinolin-4-yl)propyl]-3-pyrrolidinecarboxylic acid;

1-[(2E)-3-(2,5-difluorophenyl)-2-propenyl]-3-[3-(3-fluoro-6-methoxyquinolin-4-yl)propyl]azetidine-3-carboxylic acid;

1-[(2E)-3-(2,5-difluorophenyl)-2-propenyl]-3-[3-hydroxy-(3-fluoro-6-methoxyquinolin-4-yl)propyl]azetidine-3-carboxylic acid;

1-[(2E)-3-(2,5-difluorophenyl)-2-propenyl]-3-[3-(3-chloro-6-methoxyquinolin-4-yl)propyl]-3-pyrrolidinecarboxylic acid;

1-[(2E)-3-(2,5-difluorophenyl)-2-propenyl]-3-[3-hydroxy-(3-chloro-6-methoxyquinolin-4-yl)propyl]-3-pyrrolidinecarboxylic acid;

1-[2-(2,5-difluorophenylsulfanyl)ethyl]-3-[3-(3-chloro-6-methoxyquinolin-4-yl)propyl]-3-pyrrolidinecarboxylic acid;

1-[2-(2,5-difluorophenyloxy)ethyl]-3-[3-(3-chloro-6-methoxyquinolin-4-yl)propyl]-3-pyrrolidinecarboxylic acid;

1-[2-(thiophen-2-ylsulfanyl)ethyl]-3-[3-(3-chloro-6-methoxyquinolin-4-yl)propyl]-3-pyrrolidinecarboxylic acid;

1-[(2E)-3-(2,5-difluorophenyl)-2-propenyl]-3-[3-(3-fluoro-6-methoxyquinolin-4-yl)-3-hydroxypropyl]-3-pyrrolidinecarboxylic acid;

3-[3-(3-chloro-6-methoxyquinolin-4-yl)]-3-hydroxypropyl]-1-[(2E)-3-(2,5-difluorophenyl)-2-propenyl]-3-pyrrolidinecarboxylic acid;

1-[3-(2,5-difluorophenyl)propyl]-3-[3-(3-fluoro-6-methoxyquinolin-4-yl)]-3-hydroxypropyl]-3-pyrrolidinecarboxylic acid;

1-[2-[(2,5-difluorophenyl)thio]ethyl]-3-[3-(3-fluoro-6-methoxyquinolin-4-yl)-3-hydroxypropyl]-3-pyrrolidinecarboxylic acid;

in its enantiomeric or diastereoisomeric forms or mixtures of these forms, and/or where appropriate in syn or anti form or mixtures thereof, and its salts.

According to the invention, the products of general formula (I) may be obtained by condensing the chain R$_3$ with the 4-substituted quinoline derivative of general formula:

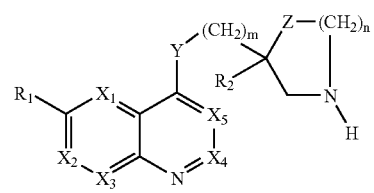

(II)

in which X$_1$, X$_2$, X$_3$, X$_4$, X$_5$, R$_1$, R$_2$, Y, Z, m and n are defined as above, R$_2$ being protected when it carries a carboxyl radical, followed where appropriate by the removal of the group protecting the carboxyl radical, optionally by the separation of the enantiomeric or diastereoisomeric forms and/or where appropriate of the syn or anti forms, and optionally by the conversion of the product obtained to a salt.

The condensation of the chain R$_3$ with the heterocyclic nitrogen is advantageously carried out by the action of a derivative of general formula:

(IIa)

in which R$_3$ is as defined above and X represents a halogen atom, a methylsulfonyl radical, a trifluoromethylsulfonyl or p-toluenesulfonyl radical, the procedure being carried out in an anhydrous, preferably inert, medium, in an organic solvent such as an amide (dimethylformamide for example), a ketone (acetone for example) or a nitrile (acetonitrile for example) in the presence of a base such as a nitrogenous organic base (for example triethylamine) or an inorganic base (alkali metal carbonate: potassium carbonate for example) at a temperature of between 20° C. and the reflux temperature of the solvent. The nitrogen atom of the pyrrolidine ring of the derivative of general formula (II) is optionally protected according to the customary methods compatible with the remainder of the molecule or the reaction; the protection is performed for example with a protecting radical chosen from t-butoxycarbonyl and benzyloxycarbonyl, and this nitrogen atom is released prior to the condensation with the derivative of formula (IIa), in particular by acid hydrolysis.

Preferably, a derivative of general formula (IIa) for which X is a chlorine, bromine or iodine atom is caused to act.

Conditions under which it is possible to carry out the condensation between the derivatives of general formulae (II) and (IIa) are also described in application WO 02/40474.

When $R_3$ is a radical -alk-$R^\circ_3$ in which $R^\circ_3$ is a group —C≡C-Rd, in which Rd is as defined above, an alkynyl halide of formula HC≡C-alk-X is intermediately condensed and then the suitable radical Rd is condensed with the alkyne thus obtained.

When $R_3$ represents a radical -alk-$R^\circ_3$ for which alk is an alkyl radical and $R^\circ_3$ represents a phenoxy, phenylthio, phenylamino, heteroaryloxy, heteroarylthio or heteroarylamino radical, it is also possible to construct the chain by first condensing a chain HO-alk-X for which X is a halogen atom, preferably iodine, under the conditions described above for the reaction of the product of general formula (IIa), and then, where appropriate, by converting the hydroxyalkyl chain to a haloalkyl, methanesulfonylalkyl or p-toluenesulfonylalkyl chain and finally by causing an aromatic derivative having the structure $R^\circ_3H$ or $R^\circ_3H_2$ to act in a basic medium.

The conversion of the hydroxylated chain to a haloalkyl or p-toluenesulfonyl chain is carried out according to the customary halogenation or sulfonylation methods, in particular a halogenating agent such as thionyl chloride, the halogenated derivatives of phosphorus (phosphorus trichloride or tribromide for example) or a sulfonylating agent such as for example methanesulfonyl chloride, p-toluenesulfonyl chloride or trifluoromethanesulfonic anhydride is caused to act. The reaction is carried out in an organic solvent such as a chlorinated solvent (dichloromethane or chloroform for example), at a temperature of between 0 and 60° C. In some cases, it may be advantageous to carry out the procedure in the presence of a base such as pyridine or triethylamine.

The reaction of the aromatic derivative $R_3H$ or $R_3H_2$ is advantageously carried out as described above for the action of the derivative of general formula (IIa), in an organic solvent such as an amide (dimethylformamide for example), a ketone (acetone for example), a nitrile (acetonitrile for example), in the presence of a base such as a nitrogenous organic base (for example triethylamine) or an inorganic base (alkali metal carbonate: potassium carbonate for example) at a temperature of between 20° C. and the reflux temperature of the reaction mixture. It may be advantageous to carry out the procedure in the presence of potassium iodide.

It is also possible to carry out the procedure in an ether (tetrahydrofuran for example) under dehydration conditions in the presence, for example, of diisopropylcarbodiimide and triphenylphosphine.

It is understood that if the radicals $R_3$ carry carboxyl or amino substitutes, the latter are protected beforehand, and then released after the reaction. The procedure is carried out according to methods well known to a person skilled in the art which do not adversely affect the remainder of the molecule, in particular according to the methods described by T. W. Greene and P. G. M. Wuts, Protective Groups in Organic Synthesis (2nd ed.), A. Wiley—Interscience Publication (1991), or by Mc Omie, Protective Groups in Organic Chemistry, Plenum Press (1973).

The protected carboxyl radical carried by $R_2$ may be chosen from easily hydrolyzable esters. By way of example, there may be mentioned methyl, benzyl or tert-butyl esters, or alternatively phenylpropyl or -2-propenyl esters. Optionally, the protection of the carboxyl radical is carried out simultaneously with the reaction.

Where appropriate, the protection of the amino radical is carried out by means of the customary protecting radicals mentioned in the above references.

The introduction and the removal of these protecting radicals are carried out according to methods known to a person skilled in the art. According to the invention, the derivatives of general formula (I) for which $R_2$ is hydroxymethyl or hydroxyethyl may be prepared by the action of an appropriate reducing agent on a derivative for which $R_2$ is carboxyl or carboxymethyl or protected carboxyl or protected carboxymethyl. A ketone functional group which may be present should then be intermediately protected. Also according to the invention, the products of general formula (I) for which $R_2$ is carboxymethyl or carboxyethyl may also be prepared from the derivatives for which $R_2$ is hydroxymethyl or hydroxyethyl, by the action on the latter of a halogenating or tosylating agent, and then of a cyanating agent and finally hydrolysis of the nitrile.

It is possible to carry out the reduction of the protected carboxyl according to the customary methods which do not adversely affect the remainder of the molecule, in particular by the action of a hydride (lithium aluminium hydride or diisobutyl aluminium hydride for example) in a solvent such as an ether (tetrahydrofuran for example) at a temperature of between 20 and 60° C. A ketone functional group which may be present is intermediately protected and then deprotected according to conventional methods known to a person skilled in the art, in particular via a cyclic or noncyclic acetal.

The reduction of the free carboxyl may be carried out according to methods which are also known to a person skilled in the art, for example by hydrogenation in the presence of a rhodium- or ruthenium-based catalyst, by the action of sodium borohydride in the presence of a Lewis acid or of lithium aluminum hydride in ether. Preferably, the ketone functional group is in this case also protected in an intermediate phase.

The conversion of the hydroxymethyl or hydroxyethyl radical to a carboxymethyl or carboxyethyl radical is carried out according to the customary methods which do not adversely affect the remainder of the molecule, in particular by the action of a halogenating agent such as for example thionyl chloride or phosphorus trichloride or phosphorus tribromide, or of a tosylating agent, followed by an alkali metal cyanide, for example potassium cyanide or sodium cyanide, in order to prepare the corresponding cyanomethyl derivative, followed by hydrolysis of the nitrile.

The halogenation may be carried out in a chlorinated solvent (dichloromethane or chloroform for example), at a temperature of between 0° C. and the reflux temperature of the solvent.

According to the invention, the preparation of the products of general formula (II) for which Y is a group CHR is carried out by condensation of a heteroaromatic derivative of general formula:

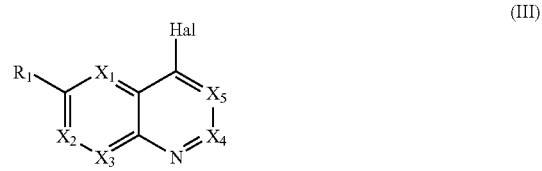

(III)

in which $R_1$, $X_1$, $X_2$, $X_3$, $X_4$ and $X_5$ are as defined above and Hal represents a halogen atom, with a derivative of general formula:

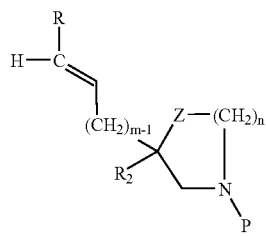
(IV)

in which P is a protecting group and R, Z, m, n and $R_2$ are as defined above or $R_2$ represents a protected radical if $R_2$ represents or carries a carboxylic acid functional group, followed by the removal of the protecting groups and/or followed by the conversion, by a subsequent operation, of the substituents of the aromatic bicycle of general formula (II) thus obtained, to give the expected derivative carrying the radical $R_1$, $R'_1$, $R'_2$, $R'_3$, $R'_4$, $R'_5$, and, where appropriate, removal of the protecting radical(s) still present in the molecule.

P may be any group protecting the nitrogen atom, which is compatible with the reaction (t-butyloxycarbonyl, benzyloxycarbonyl for example). The groups protecting the acid functional groups are chosen from the customary groups whose introduction and removal do not affect the remainder of the molecule, in particular those mentioned in the references cited above.

The reaction may be carried out in particular by the successive action, on the derivative of general formula (II), of an organoborane (9-borabicyclo[3.3.1]nonane for example) in a solvent such as an ether (tetrahydrofuran or dioxane for example) at a temperature of between −20 and 20° C. and then of the bicyclic derivative of general formula (III) for which Hal represents a chlorine atom or preferably a bromine or iodine atom, by analogy with the methods described by Suzuki et al. Pure and Appl. Chem., 57, 1749 (1985). The reaction is generally carried out in the presence of a palladium salt (diphenylphosphinoferrocenepalladium chloride for example) and of a base such as potassium phosphate at a temperature of between 20° C. and the reflux temperature of the solvent.

According to the invention, the products of general formula (II) for which Y represents a CROH group may be prepared by oxidation, in a basic medium, of the corresponding derivative for which Y is a group CHR. The oxidation is carried out by the action of oxygen, preferably in an inert solvent such as dimethyl sulfoxide, in the presence of tert-butanol and of a base such as potassium or sodium tert-butoxide at a temperature of between 0 and 100° C.

The derivatives of general formula (II) for which Y is a group CRF or $CF_2$ may be prepared by fluorination respectively from the derivative for which Y is a group CROH and that for which Y is a carbonyl group. The reaction is carried out in the presence of a sulfur fluoride [for example in the presence of aminosulfur trifluoride (diethylaminosulfur trifluoride (Tetrahedron, 44, 2875 (1988), bis(2-methoxyethyl) aminosulfur trifluoride (Deoxofluor®), morpholinosulfur trifluoride for example) or alternatively in the presence of sulfur tetrafluoride (J. Org. Chem., 40, 3808 (1975)]. The fluorination reacton may also be carried out using a fluorinating agent such as hexafluoropropyl diethylamine (JP 2 039 546) or N-(2-chloro-1,1,2-trifluoroethyl)diethylamine.

The procedure is carried out in an organic solvent such as a chlorinated solvent (for example dichloromethane, dichloroethane, chloroform) or in an ether (tetrahydrofuran, dioxane for example) at a temperature of between −78 and 40° C. (preferably between 0 and 30° C.). It is advantageous to carry out the procedure in an inert medium (argon or nitrogen in particular).

The derivatives of general formula (II) for which Y is a carbonyl group may be prepared by oxidation of the corresponding derivative of general formula (II) for which Y is a CHOH group. This oxidation is carried out for example using potassium permanganate, optionally in a sodium hydroxide solution (for example 3 N sodium hydroxide), at a temperature of between −20 and 20° C., or alternatively by the action of oxalyl chloride in the presence of dimethyl sulfoxide, followed by the addition of an amine such as triethylamine, in an inert solvent such as dichloromethane, dimethyl sulfoxide at a temperature of between −60 and 20° C. by analogy with the method described by D. SWERN et al., J. Org. Chem., 44, 4148 (1979).

These derivatives may also be prepared by condensation of the derivative containing lithium at the 4-position of the heteroaromatic derivative of general formula:

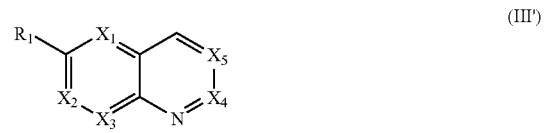
(III')

in which $R_1$, $X_1$, $X_2$, $X_3$, $X_4$ and $X_5$ are as defined above, with a derivative of general formula:

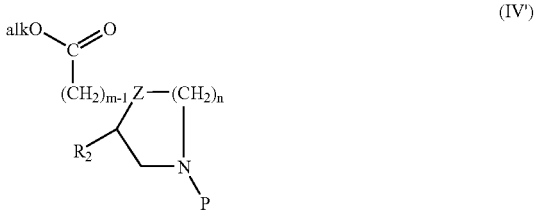
(IV')

in which P, $R_2$, m and n are as defined in formula (IV) and alk represents an alkyl radical containing from 1 to 4 carbon atoms, preferably methyl, followed by the removal of the protecting groups and/or followed by the conversion, by subsequent operations, of the substituents of the aromatic bicycle of general formula (II) thus obtained, to give the expected derivative carrying the radical $R_1$, $R'_1$, $R'_2$, $R'_3$, $R'_4$, $R'_5$, and where appropriate, removal of the protecting radical (s) still present in the molecule.

The formation of the derivative containing lithium at the 4-position of the derivative (III') is carried out with the aid of a strong lithium base such as butyllithium, sec-butyllithium, or preferably lithium diisopropylamide, in a solvent such as an ether, tetrahydrofuran for example, at a temperature of between −78° C. and −40° C. The condensation of this lithium-containing derivative with the ester (IV') is carried out in the same solvent, at a temperature of between −78° C. and 0° C.

The derivative of formula (III') may be prepared according to a method described in patent application WO 02/40474.

The derivative of general formula (II) for which Y is a group $CRNH_2$ may be prepared from the corresponding CHOH derivative which is converted to its tosylated derivative, with which ammonia is reacted. The procedure is carried out in an inert solvent such as N,N-dimethylformamide or dimethyl sulfoxide, and preferably under pressure (2 to 20 atmospheres) at a temperature of between 20 and 100° C.

The tosyloxy derivative is obtained from the product of general product (II) for which Y is CROH, by the action of tosyl chloride in pyridine, at a temperature of between −10 and 20° C.

Application WO 02/40474 provides methods for obtaining the different values of $R_1$, $X_1$, $X_2$, $X_3$, $X_4$ and $X_5$ in the derivatives of general formula (II) and (III) and of Hal in the derivatives of general formula (III).

The derivatives of general formula (IV) may be prepared by condensation with a derivative of general formula:

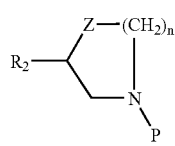  (V)

in which n and P are as defined above, and $R_2$ is as defined in general formula (IV) or (IV'), of a product of general formula

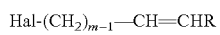 (VI)

in which Hal represents a halogen atom, preferably bromine and m and R are as defined above. The procedure is preferably carried out in the presence of a strong base, in particular an alkali metal amide, for example lithium bis(trimethylsilyl)amide, or a lithium compound, for example butyllithium, in an organic solvent which may be in particular an ether such as tetrahydrofuran or dioxane.

In the case where m=1, the procedure is preferably carried out by condensing a derivative of general formula (V) as defined above with a product of the dibromoethane type of general formula:

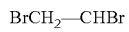 (VI')

in which R is as defined above, followed by hydrobromide removal from the product obtained by a method known to a person skilled in the art. Reference may be made for example to the method described by R. A. Bunce et al. Organic Preparations Procedure Internationale 1999-31 (1) p. 99–106.

Other methods which make it possible to prepare the derivatives of general formula (IV) are described in application WO 02/40474. The procedure is carried out starting with an appropriate nitrogenous heterocyclic derivative.

Examples are provided below in the experimental part.

The intermediate derivatives of general formulae (II) and (IV) obtained during the use of the method according to the invention are novel and, as such, form part of the invention.

The derivatives of formula (V) are in general known (there may be mentioned for example the references EP 405506 or WO 00/37458) and, for some, are commercially available. Preparations are presented below in the experimental part.

It is understood that the derivatives of general formula (I) and (II) can exist in enantiomeric or diastereoisomeric forms or in syn or anti form, which of course fall within the scope of the present invention. These forms may be separated according to the usual methods, known to persons skilled in the art, in particular by chiral chromatography or by High Performance Liquid Chromatography (HPLC).

The derivatives of general formula (I) can be purified, where appropriate, by physical methods such as crystallization or chromatography.

The derivatives of general formula (I) may be, where appropriate, converted to addition salts with acids or with bases by known methods. It is understood that these salts with acids or bases also fall within the scope of the present invention.

As examples of addition salts with pharmaceutically acceptable acids, there may be mentioned the salts formed with inorganic acids (for example hydrochlorides, hydrobromides, sulfates, nitrates or phosphates) or with organic acids (for example succinates, fumarates, tartrates, acetates, propionates, maleates, citrates, methanesulfonates, ethanesulfonates, phenylsufonates, p-toluenesulfonates, isethionates, naphthylsulfonates or camphorsulfonates) or with substitution derivatives of these acids.

The derivatives of general formula (I) carrying the carboxyl radical may be converted to metal salts or to addition salts with nitrogenous bases according to methods known per se. The salts may be obtained by the action of a metal (for example an alkali or alkaline-earth metal) base, of ammonia or of an amine, on a product according to the invention, in an appropriate solvent such as an alcohol, an ether or water, or by an exchange reaction with a salt of an organic acid. The salt formed precipitates after optional concentration of the solution, it is separated by filtration, decantation or lyophilization. As examples of pharmaceutically acceptable salts, there may be mentioned in particular the salts with alkali metals (sodium, potassium, lithium) or with alkaline earth metals (magnesium, calcium), ammonium salt, the salts of nitrogenous bases (ethanolamine, diethanolamine, trimethylamine, triethylamine, methylamine, propylamine, diisopropylamine, N,N-dimethylethanolamine, benzylamine, dicyclohexylamine, N-benzyl-β-phen-ethylamine, N,N'-dibenzylethylenediamine, diphenylenediamine, benzhydrylamine, quinine, choline, arginine, lysine, leucine, dibenzylamine).

The derivatives of general formula (I) according to the invention are particularly active antibacterial agents.

The study below demonstrates this.

a) Activity in vitro The method of dilutions in agar medium in agreement with the NCCLS recommendations is used for the determination of the minimum inhibitory concentrations (MIC) expressed in µg/ml.

The activities of the compounds of Examples 1 to 4 are grouped together in the following table:

| Gram-positive MIC µg/ml at 24 hours | |
|---|---|
| S. aureus IP8203 sensitive | <0.015–4 |
| S. aureus AS 5155 methicillin resistant | <0.015–4 |
| S. pneumoniae 6254-01 $MLS_B$ resistant | <0.015–4 |

| | |
|---|---|
| *E. faecalis* ATCC29212 vancomycin resistant | 0.25–32 |

Gram-negative MIC µg/ml at 48 hours

| | |
|---|---|
| *M. catarrhalis* IPA151 sensitive | <0.12–2 |
| *H. influenzae* 87169 sensitive | 1–>64 |

In vitro, the compounds of the invention therefore proved quite remarkable both on Gram-positive microorganisms and on Gram-negative microorganisms.

b) Activity in vivo

Some derivatives proved active on experimental infections of mice with *Staphylococcus aureus* IP8203 at doses of between 5 and 50 mg/kg by the subcutaneous route or by the oral route.

c) The products according to the invention are particularly advantageous because of their low toxicity. None of the products exhibited toxicity at the dose of 50 mg/kg by the subcutaneous route or by the oral route in mice (2 administrations/day).

These properties make said products, and their salts with pharmaceutically acceptable acids and bases, suitable for use as medicaments in the treatment of conditions caused by sensitive microorganisms brought about by Gram-positive bacteria and in particular in those caused *staphylococcus*, such as staphylococcal septicemia, facial or cutaneous malignant staphylococcia, pyoderma, septic or suppurant wounds, anthrax, phlegmons, erysipela, primitive or post-influenza acute staphylococcia, bronchopneumonia, pulmonary suppurations, and in those caused by streptococci or enterococci.

These products may also be used as medicaments in the treatment of upper and lower respiratory infections caused by Gram-negative bacteria such as Haemophilus influenzae and Moraxella catarrhalis.

The subject of the present invention is therefore also, as medicaments and in particular medicaments intended for the treatment of bacterial infections in humans or animals, the compounds of general formula (I) as defined above and their pharmaceutically acceptable salts, in particular the preferred compounds mentioned above.

The present invention also relates to the pharmaceutical compositions containing at least one 4-substituted quinoline derivative according to the invention, where appropriate in salt form, in the pure state or in the form of a combination with one or more compatible and pharmaceutically acceptable diluents or adjuvants.

The compositions according to the invention may be used by the oral, parenteral, topical or rectal route or as aerosols.

As solid compositions for oral administration, there may be used tablets, pills, gelatin capsules, powders or granules. In these compositions, the active product according to the invention is mixed with one or more inert diluents or adjuvants, such as sucrose, lactose or starch. These compositions may comprise substances other than diluents, for example a lubricant such as magnesium stearate or a coating intended for a controlled release.

As liquid compositions for oral administration, there may be used solutions which are pharmaceutically acceptable, suspensions, emulsions, syrups and elixirs containing inert diluents such as water or paraffin oil. These compositions may also comprise substances other than diluents, for example wetting products, sweeteners or flavorings.

The compositions for parenteral administration may be sterile solutions or emulsions. As a solvent or vehicle, it is possible to use water, propylene glycol, a polyethylene glycol, vegetable oils, in particular olive oil, organic esters for injection, for example ethyl oleate. These compositions may also contain adjuvants, in particular wetting, isotonizing, emulsifying, dispersing and stabilizing agents.

The sterilization may be carried out in several ways, for example using a bacteriological filter, by irradiation or by heating. They may also be prepared in the form of sterile solid compositions which may be dissolved at the time of use in sterile water or any other sterile medium for injection.

The compositions for topical administration may be for example creams, ointments, lotions or aerosols.

The compositions for rectal administration are suppositories or rectal capsules which contain, in addition to the active ingredient, excipients such as cocoa butter, semisynthetic glycerides or polyethylene glycols.

The compositions may also be aerosols. For use in the form of liquid aerosols, the compositions may be stable sterile solutions or solid compositions dissolved at the time of use in pyrogen-free sterile water, in saline or any other pharmaceutically acceptable vehicle. For use in the form of dry aerosols intended to be directly inhaled, the active ingredient is finely divided and combined with a water-soluble solid diluent or vehicle having a particle size of 30 to 80 µm, for example dextran, mannitol or lactose.

In human therapy, the novel 4-substituted quinoline derivatives according to the invention are particularly useful in the treatment of infections of bacterial origin. The doses depend on the desired effects and the duration of the treatment. The doctor will determine the dosage which he judges most appropriate according to the treatment, according to the age, the weight, the degree of the infection and the other factors specific to the subject to be treated. Generally, the doses are between 750 mg and 3 g of active product in 2 or 3 doses per day by the oral route or between 400 mg and 1.2 g by the intravenous route for an adult.

The following examples illustrate compositions according to the invention.

a) A liquid composition intended for parenteral use is prepared according to the usual technique, comprising:

| | |
|---|---|
| (±)-1-[(2E)-3-(2,5-difluoro-phenyl)-2-propenyl]-3-[3-(3-fluoro-6-methoxy-quinolin-4-yl)-propyl]pyrrolidine-3-carboxylic acid | 1 g |
| Glucose | qs 2.5% |
| Sodium hydroxide | qs pH = 4–4.5 |
| Water for injection | qs 20 ml | b) A liquid composition intended for parenteral use is prepared according to the usual technique, comprising:

| | |
|---|---|
| 2-[3-(3-fluoro-6-methoxyquinolin-4-yl)propyl]-4-[2-(2,5-difluorophenyl-sulfanyl)ethyl]morpholine-2-carboxylic acid | 500 mg |
| Glucose | qs 5% |
| Sodium hydroxide | qs pH = 4–4.5 |
| Water for injection | qs 50 ml |

The following examples illustrate the invention.

EXAMPLE 1

(±)-1-[(2E)-3-(2,5-difluorophenyl)-2-propenyl]-3-[3-(3-fluoro-6-methoxyquinolin-4-yl)propyl]-3-pyrrolidinecarboxylic acid:

14.2 cm$^3$ of a 5 N aqueous sodium hydroxide solution are added at a temperature in the region of 20° C. to 1.25 g (2.336 mmol) of methyl (±)-1-[(2E)-3-(2,5-difluorophenyl)-2-propenyl]-3-[3-(3-fluoro-6-methoxyquinolin-4-yl)propyl]-3-pyrrolidinecarboxylate in solution in 25 cm$^3$ of dioxane. After stirring under reflux for 16 hours, the reaction medium is concentrated to dryness under reduced pressure (2.7 kPa) to give a residue which is taken up in 40 cm$^3$ of acetonitrile. After stirring for 0.5 hour at a temperature in the region of 0° C., the orange solid in suspension is filtered, rinsed with twice 7 cm$^3$ of acetonitrile and then dissolved in 55 cm$^3$ of water. The aqueous phase is then acidified with 1 N hydrochloric acid to a pH value in the region of 6–7 and then extracted with twice 20 cm$^3$ of dichloromethane. The organic phases are combined, washed with twice 10 cm$^3$ of water, dried over anhydrous magnesium sulfate, filtered and concentrated to dryness under reduced pressure (2.7 kPa) to give 0.55 g of (±)-1-[(2E)-3-(2,5-difluorophenyl)-2-propenyl]-3-[3-(3-fluoro-6-methoxyquinolin-4-yl)propyl]-3-pyrrolidinecarboxylic acid, in the form of a yellow solid melting at 77° C.

$^1$H NMR (300 MHz, (CD$_3$)$_2$SO d6, δ in ppm): 1.59 (mt: 4H); 1.81 (mt: 2H); 2.25 (mt: 1H); 2.38 (broad d, J=9 Hz: 1H); 2.57 (mt: 1H); 2.96 (broad d, J=9 Hz: 1H); 3.07 (broad t, J=7.5 Hz: 2H); 3.21 (broad d, J=6 Hz: 2H); 3.94 (s: 3H); 6.47 (dt, J=16 and 6 Hz: 1H); 6.61 (broad d, J=16 Hz: 1H); 7.12 (mt: 1H); 7.24 (split t, J=9.5 and 4.5 Hz: 1H); 7.35 (d, J=3 Hz: 1H); 7.39 (dd, J=9 and 3 Hz: 1H); 7.50 (mt: 1H); 7.96 (d, J=9 Hz: 1H); 8.68 (broad s: 1H). CI m/z=485 (MH$^+$).

Methyl (±)-1-[(2E)-3-(2,5-difluorophenyl)-2-propenyl]-3-[3-(3-fluoro-6-methox-4-quinolin-4-yl)propyl]-3-pyrrolidinecarboxylate may be prepared as described in Example 2.

EXAMPLE 2

Methyl (±)-1-[(2E)-3-(2,5-difluorophenyl)-2-propenyl]-3-[3-(3-fluoro-6-methoxyquinolin-4-yl)propyl]-3-pyrrolidinecarboxylate may be prepared as described later in Example 2.

3.92 g of potassium carbonate, 1.03 g of potassium iodide and then a freshly prepared solution of 2-[(1E)-3-chloro-1-propenyl]-1,4-difluorobenzene (7.34 mmol) in dichloromethane are added at a temperature in the region of 20° C. under an argon atmosphere to 2.171 g (5.67 mmol) of methyl (±)-3-[3-(3-fluoro-6-methoxyquinolin-4-yl)propyl]-3-pyrrolidinecarboxylate dihydrochloride in solution in 150 cm$^3$ of acetonitrile. After stirring under reflux for 20 hours, the reaction mixture is concentrated to dryness under reduced pressure (2.7 kPa) to give a residue which is taken up in 200 cm$^3$ of dichloromethane, washed with 3 times 100 cm$^3$ of water and then with 75 cm$^3$ of a saturated aqueous sodium chloride solution. The organic phase is dried over anhydrous magnesium sulfate, filtered and concentrated to dryness under reduced pressure (2.7 kPa) to give 2.6 g of an orange oil which is purified by flash chromatography [eluent: cyclohexane/ethyl acetate (1/1 by volume)]. After concentrating the fractions under reduced pressure, 1.45 g of methyl (±)-1-[(2E)-3-(2,5-difluorophenyl)-2-propenyl]-3-[3-(3-fluoro-6-methoxyquinolin-4-yl)propyl]-3-pyrrolidinecarboxylate are obtained in the form of a yellow oil;

$^1$H NMR (300 MHz, (CD$_3$)$_2$SO d6, δ in ppm): from 1.40 to 1.70 (mt: 3H); 1.81 (mt: 2H); 2.26 (mt: 1H); 2.36 (d, J=9.5 Hz: 1H); from 2.40 to 2.65 (mt: 2H); 2.95 (d, J=9.5 Hz: 1H); 3.06 (broad t, J=7.5 Hz: 2h); 3.18 (d, J=6 Hz: 2H); 3.53 (s: 3H); 3.95 (s: 3H); 6.45 (dt, J=16.5 and 6 Hz: 1H); 6.60 (broad d, J=16.5 Hz: 1H); 7.12 (mt: 1H); 7.23 (split t, J=9.5 and 4.5 Hz: 1H); 7.34 (d, J=3 Hz: 1H); 7.39 (dd, J=9 and 3 Hz: 1H); 7.49 (ddd, J=9.5–6 and 3 Hz: 1H); 7.96 (d, J=9 Hz: 1H); 8.68 (broad s: 1H). EI m/z=498 (M$^+$), 439 (M–CO$_2$CH$_3^+$), 153 (C$_9$H$_7$F$_2^+$).

The solution of 2-[(1E)-3-chloro-1-propenyl]-1,4-difluorobenzene (7.34 mmol) in dichloromethane may be prepared in the following manner:

A solution of 0.66 cm$^3$ (9.07 mmol) of thionyl chloride and 1.08 g (9.07 mmol) of benzotriazole in 70 cm$^3$ of dichloromethane are added at a temperature in the region of 20° C., under an argon atmosphere, to 1.25 g (7.34 mmol) of 2,5-difluorocinnamyl alcohol in solution in 130 cm$^3$ of dichloromethane. After stirring for 10 minutes, the reaction mixture is filtered on No. 3 sintered glass and the solid residue rinsed with twice 20 cm$^3$ of dichloromethane. The filtrate is washed with 3 times 75 cm$^3$ of water. The organic phase is dried over anhydrous magnesium sulfate and filtered to give a solution of 2-[(1E)-3-chloro-1-propenyl]-1,4-difluorobenzene (7.34 mmol) which is immediately used as it is in the next step.

Methyl (±)-3-[3-(3-fluoro-6-methoxyquinolin-4-yl)propyl]-3-pyrrolidinecarboxylate dihydrochloride may be prepared in the following manner:

8.117 cm$^3$ of a 4 N hydrochloric acid solution in dioxane are added at a temperature in the region of 20° C. to 2.9 g (6.495 mmol) of 1-(1,1-dimethylethyl) and 3-methyl (±)-3-[3-(3-fluoro-6-methoxyquinolin-4-yl)propyl]-1,3-pyrrolidinedicarboxylate in solution in 20 cm$^3$ of methanol. After stirring for 4 hours at a temperature in the region of 20° C., the reaction mixture is concentrated to dryness under reduced pressure (2.7 kPa) to give 2.38 g of methyl (±)-3-[3-(3-fluoro-6-methoxyquinolin-4-yl)propyl]-3-pyrrolidinecarboxylate dihydrochloride, in the form of a yellow solid. EI m/z=346 (M$^+$), 315 (M–OCH$_3^+$), 304 (M–C$_2$H$_4$N$^+$), 204 (C$_{12}$H$_{11}$ONF$^+$).

1-(1,1-dimethylethyl) and 3-methyl (±)-3-[3-(3-fluoro-6-methoxyquinolin-4-yl)propyl]-1,3-pyrrolidinedicarboxylate may be prepared in the following manner:

A solution of 2.23 g (8.279 mmol) of 1-(1,1-dimethylethyl) and 3-methyl (±)-3-(2-propenyl)-1,3-pyrrolidinedicarboxylate in 30 cm$^3$ of tetrahydrofuran is added at a temperature in the region of 0° C., under an argon atmosphere, to 24.84 cm$^3$ (12.42 mmol) of a 0.5 M solution of 9-BBN (9-borabicyclo[3.3.1]nonane/THF. After heating the reaction mixture to a temperature in the region of 20° C. and then stirring for 3 hours at a temperature in the region of 20° C., 2.509 g (8.279 mmol) of 3-fluoro-4-iodo-6-methoxyquinoline in suspension in 70 cm$^3$ of tetrahydrofuran and then 5.27 g (24.84 mmol) of potassium phosphate and 0.182 g (0.248 mmol) of PdCl$_2$dppf (1,1'-bis(diphenylphosphino)ferrocenepalladium dichloride) are added successively. After stirring for 16 hours at the reflux temperature, the reaction mixture is cooled and then filtered on Celite®. The Celite® is rinsed with 3 times 25 cm$^3$ of tetrahydrofuran. The filtrate is then concentrated to dryness under reduced pressure (2.7 kPa). The residue is taken up with 100 cm$^3$ of dichloromethane, washed with 3 times 40 cm$^3$ of water and then with 50 cm$^3$ of a saturated aqueous sodium chloride solution. The organic phase is dried over anhydrous magnesium sulfate, filtered and concentrated to dryness under reduced pressure (2.7 kPa) to give 5.7 g of an orange oil which is purified by flash chromatography [eluent: cyclohexane/ethyl acetate (7/3 by volume)]. After concentrating the fractions under reduced pressure, 2.9 g of 1-(1,1-dimethylethyl) and 3-methyl (±)-3-[3-(3-fluoro-6-methoxyquinolin-4-yl)propyl]-1,3-pyrrolidinedicarboxylate are obtained in the form of a yellow oil.

EI m/z=446 (M$^+$), 390 (M–C$_4$H$_8{}^+$), 345 (390–CO$_2$H$^+$), 204 (C$_{12}$H$_{11}$ONF$^+$).

3-Fluoro-4-iodo-6-methoxyquinoline may be prepared according to the method described in patent application WO 02/40474.

1-(1,1-Dimethylethyl) and 3-methyl (±)-3-(2-propenyl)-1,3-pyrrolidinedicarboxylate may be prepared in the following manner:

12.23 cm$^3$ (12.23 mmol) of lithium bis(trimethylsilyl)amide as a 1 M solution in tetrahydrofuran are added dropwise at a temperature in the region of –78° C., under an argon atmosphere, to 2.55 g (11.12 mmol) of 1-(1,1-dimethylethyl) and 3-methyl 1,3-pyrrolidinedicarboxylate in solution in 30 cm$^3$ of tetrahydrofuran. After stirring for 0.25 hour at a temperature in the region of –78° C., 1.486 cm$^3$ (16.68 mmol) of -2-propenyl bromide are added and then the temperature is allowed to change from –78° C. to a temperature in the region of 20° C. over 1.5 hours. The reaction medium is then hydrolyzed with 10 cm$^3$ of a 1 N aqueous hydrochloric acid solution and then concentrated to three quarters under reduced pressure (2.7 kPa). The concentrate is taken up in 50 cm$^3$ of ethyl acetate. The organic phase is separated by decantation, successively washed with 15 cm$^3$ of a 1 N aqueous hydrochloric acid solution, 20 cm$^3$ of water and twice 20 cm$^3$ of a saturated aqueous sodium bicarbonate solution, dried over anhydrous magnesium sulfate, filtered and then concentrated to dryness under reduced pressure (2.7 kPa) to give 2.5 g of yellow oil which is purified by flash chromatography [eluent: cyclohexane/ethyl acetate (7/3 by volume)]. After concentrating the fractions under reduced pressure, 2.23 g of 1-(1,1-dimethylethyl) and 3-methyl (±)-3-(2-propenyl)-1,3-pyrrolidinedicarboxylate are obtained in the form of a colorless oil.

CI m/z 287 (MNH$_4{}^+$), 270 (MH$^+$), 231 (MNH$_4{}^+$–C$_4$H$_8$).

1-(1,1-Dimethylethyl) and 3-methyl 1,3-pyrrolidinedicarboxylate may be prepared in the following manner:

3 cm$^3$ of triethylamine and then 4.649 g of di-tert-butyl dicarbonate in solution in 30 cm$^3$ of dichloromethane are successively added at a temperature in the region of 20° C., under an argon atmosphere, to 2.5 g (19.36 mmol) of methyl (±)-3-pyrrolidinecarboxylate in solution in 50 cm$^3$ of dichloromethane. After stirring for 20 hours at a temperature in the region of 20° C., the reaction mixture is successively washed with 3 times 50 cm$^3$ of water and 50 cm$^3$ of a saturated aqueous sodium chloride solution. The organic phase is dried over anhydrous magnesium sulfate, filtered and then concentrated to dryness under reduced pressure (2.7 kPa) to give 3.08 g of a colorless oil which is purified by flash chromatography [eluent: cyclohexane/ethyl acetate (6/4 by volume)]. After concentrating the fractions under reduced pressure, 2.55 g of 1-(1,1-dimethylethyl) and 3-methyl 1,3-pyrrolidinedicarboxylate are obtained in the form of a colorless oil.

CI m/z 247 (MNH$_4{}^+$), 230 (MH$^+$), 191 (MNH$_4{}^+$–C$_4$H$_8$), 174 (MH$^+$—C$_4$H$_8$).

Methyl (±)-3-pyrrolidinecarboxylate may be prepared in the following manner:

0.704 g of 10% palladium on carbon (Pd/C) and then 11.5 g of ammonium formate are successively added at a temperature in the region of 20° C., under an argon atmosphere, to 5 g (22.8 mmol) of methyl (±)-1-(phenylmethyl)-3-pyrrolidinecarboxylate in solution in 100 cm$^3$ of methanol. After stirring for 3 hours at the reflux temperature, the reaction mixture is filtered on Celite®. The Celite® is rinsed with 3 times 20 cm$^3$ of methanol. The filtrate is then concentrated to dryness under reduced pressure (2.7 kPa) to give 2.5 g of methyl (±)-3-pyrrolidinecarboxylate in the form of a colorless oil.

CI m/z 130 (MH$^+$).

Methyl (±)-1-(phenylmethyl)-3-pyrrolidinecarboxylate may be prepared in the following manner:

0.213 cm$^3$ (2.758 mmol) of trifluoroacetic acid is added dropwise at a temperature in the region of 20° C., under an argon atmosphere, to 9.496 g (110.3 mmol) of methyl acrylate and 32.37 g (115.8 mmol) of N-butoxymethyl-N-trimethysilylmethylbenzylamine (Ashiwa's dipole) in solution in 350 cm$^3$ of dichloromethane. The reaction is very exothermic; after stirring for 4 hours at a temperature in the region of 20° C., 15 g of potassium carbonate are added. After stirring for 15 minutes at a temperature in the region of 20° C., the reaction mixture is successively washed with 3 times 150 cm$^3$ of water and 150 cm$^3$ of a saturated aqueous sodium chloride solution. The organic phase is dried over anhydrous magnesium sulfate, filtered and then concentrated to dryness under reduced pressure (2.7 kPa) to give 26 g of a yellow oil which is purified by flash chromatography [eluant: cyclohexane/ethyl acetate (gradient from 7/3 to 6/4 by volume)]. After concentrating the fractions under reduced pressure, 24.5 g of methyl (±)-1-(phenylmethyl)-3-pyrrolidinecarboxylate are obtained in the form of a yellow oil.

EI m/z 219 (M$^+$), 188 (M–CH$_3$O$^+$), 142 (M–C$_6$H$_5{}^+$), 128 (M–C$_7$H$_7{}^+$).

N-Butoxymethyl-N-trimethylsilylmethylbenzylamine (Ashiwa's dipole) may be prepared according to the method described by Terao, Y., Kotaki, H., Imai, N., Achiwa, K. *Chem. Pharm. Bull.* 1985, 33, 896.

EXAMPLE 3

Enantiomer A of 1-[(2E)-3-(2,5-difluorophenyl)-2-propenyl]-3-[3-(3-fluoro-6-methoxyquinolin-4-yl)propyl]-3-pyrrolidinecarboxylic acid 1.17 cm$^3$ of a 5 N aqueous sodium hydroxide solution are added at a temperature in the region of 20° C. to 0.0693 g (0.139 mmol) of the enantiomer A (levorotatory) of methyl 1-[(2E)-3-(2,5-difluorophenyl)-2-propenyl]-3-[3-(3-fluoro-6-methoxyquinolin-4-yl)propyl]-3-pyrrolidinecarboxylate in solution in 3 cm$^3$ of dioxane. After stirring under reflux for 48 hours, the reaction medium is concentrated to dryness under reduced pressure (2.7 kPa) to give a residue which is taken up in 5 cm$^3$ of water and 5 cm$^3$ of dichloromethane. The aqueous phase is acidified with 5 N and then 1 N hydrochloric acid to a pH value in the region of 7. The organic phase is separated by decantation and then the aqueous phase is concentrated to dryness under reduced pressure (2.7 kPa) to give 0.067 g of residue which is purified by flash chromatography [eluent: dichloromethane-/methanol/acetonitrile (60/20/20 by volume)]. After concentrating the fractions under reduced pressure, 0.059 g of a beige solid is obtained which is taken up in 5 cm$^3$ of water and 5 cm$^3$ of dichloromethane. The pH of the aqueous phase is adjusted to 7 with a 0.01 N aqueous sodium hydroxide solution. The aqueous phase is extracted with twice 5 cm$^3$ of dichloromethane. The organic phases are combined, washed with 5 cm³ of water, dried over anhydrous magnesium sulfate, filtered and concentrated to dryness under reduced pressure (2.7 kPa) to give 0.04 g of the enantiomer A of 1-[(2E)-3-(2,5-difluorophenyl)-2-propenyl]-3-[3-(3-fluoro-6-methoxyquinolin-4-yl)propyl]-3-pyrrolidinecarboxylic acid (absolute configuration not determined) in the form of a beige solid melting at 76–80° C.

$[\alpha]_D^{20}$+7.3+/−0.4 [dichloromethane (c=0.5), 589 nm];

¹H NMR (300 MHz, $(CD_3)_2SO$ d6, δ in ppm): 1.66 (mt: 4H); 1.79 (mt: 2H); 2.24 (mt: 1H); 2.35 (d, J=9 Hz: 1H); from 2.40 to 2.60 (mt: 1H); 2.94 (d, J=9 Hz: 1H); 3.06 (broad t, J=7 Hz: 2H); 3.19 (d, J=6 Hz: 2H); 3.95 (s: 3H); 6.48 (dt, J=16 and 6 Hz: 1H); 6.61 (broad d, J=16 Hz: 1H); 7.14 (mt: 1H); 7.25 (split t, J=9.5 and 5 Hz: 1H); from 7.30 to 7.45 (mt: 2H); 7.51 (ddd, J=9.5–6 and 3 Hz: 1H); 7.96 (d, J=9 Hz: 1H); 8.69(s: 1H). EI m/z 484 (M⁺), 439 (M−CO₂H⁺), 153 ($C_9H_7F_2^+$).

The enantiomer A (levorotatory) of methyl 1-[(2E)-3-(2,5-difluorophenyl)-2-propenyl]-3-[3-(3-fluoro-6-methoxyquinolin-4-yl)propyl]-3-pyrrolidinecarboxylate may be prepared as described later in Examples 5 and 6.

EXAMPLE 4

Enantiomer B of 1-[(2E)-3-(2,5-difluorophenyl)-2-propenyl]-3-[3-(3-fluoro-6-methoxyquinolin-4-yl)propyl]-3-pyrrolidinecarboxylic acid 1.137 cm³ of a 5 N aqueous sodium hydroxide solution are added at a temperature in the region of 20° C. to 0.0675 g (0.135 mmol) of the enantiomer B (dextrorotatory) of methyl 1-[(2E)-3-(2,5-difluorophenyl)-2-propenyl]-3-[3-(3-fluoro-6-methoxyquinolin-4-yl)propyl]-3-pyrrolidinecarboxylate in solution in 3 cm³ of dioxane. After stirring under reflux for 48 hours, the reaction medium is concentrated to dryness under reduced pressure (2.7 kPa) to give a residue which is taken up in 2 cm³ of water and 5 cm³ of dichloromethane. The aqueous phase is acidified with 1 N and then 0.1 N hydrochloric acid to a pH value of 7. The aqueous phase is extracted with twice 5 cm³ of dichloromethane. The organic phases are combined, washed with 5 cm³ of water, dried over anhydrous magnesium sulfate, filtered and concentrated to dryness under reduced pressure (2.7 kPa) to give 0.035 g of the enantiomer B of 1-[(2E)-3-(2,5-difluorophenyl)-2-propenyl]-3-[3-(3-fluoro-6-methoxyquinolin-4-yl)propyl]-3-pyrrolidinecarboxylic acid (absolute configuration not determined) in the form of a beige solid melting at 80–84° C.

$[\alpha]_D^{20}$−7.7+/−0.4 [dichloromethane (c=0.5), 589 nm].

¹H NMR (300 MHz, $(CD_3)_2SO$ d6, δ in ppm): 1.58 (mt: 4H); 1.80 (mt: 2H); 2.25 (mt: 1H); 2.36 (broad d, J=9 Hz: 1H); from 2.45 to 2.65 (mt: 1H); 2.93 (broad d, J=9 Hz: 1H); 3.07 (broad t, J=7 Hz: 2H); 3.18 (d, J=6 Hz: 2H); 3.94 (s: 3H); 6.47 (dt, J=16 and 6 Hz: 1H); 6.61 (broad d, J=16 Hz: 1H); 7.12 (mt: 1H); 7.24 (split t, J=9.5 and 4.5 Hz: 1H); 7.35 (mt: 1H); 7.38 (dd, J=9 and 3 Hz: 1H); 7.50 (ddd, J=9.5–6 and 3 Hz: 1H); 7.96 (d, J=9 Hz: 1H); 8.69 (broad s: 1H). EI mz 484 (M⁺), 439 (M−CO₂H⁺), 153 ($C_9H_7F_2^+$).

The enantiomer B (dextrorotatory) of methyl 1-[(2E)-3-(2,5-difluorophenyl)-2-propenyl]-3-[3-(3-fluoro-6-methoxyquinolin-4-yl)propyl]-3-pyrrolidinecarboxylate may be prepared as described in Examples 5 and 6.

EXAMPLES 5 AND 6

Enantiomers A (levorotatory) and B (dextrorotatory) of methyl 1-[(2E)-3-(2,5-difluorophenyl)-2-propenyl]-3-[3-(3-fluoro-6-methoxyquinolin-4-yl) propyl]-3-pyrrolidinecarboxylate Methyl (±)-1-[(2E)-3-(2,5-difluorophenyl)-2-propenyl]-3-[3-(3-fluoro-6-methoxyquinolin-4-yl)propyl]-3-pyrrolidinecarboxylate (0.155 g) is injected into a column 80 cm in diameter and 35 cm in length containing 1200 g of chiral stationary phase: Chiralpak AD TM having a particle size of 20 μm. The elution is carried out with a mobile phase [heptane/2-propanol/methanol (92/5/3 by volume)] at a flow rate of 120 ml/min, the detection is performed by UV at 254 nm. The enantiomer A (levorotatory), having an undetermined absolute configuration, which was eluted in the first position, is recovered and then concentrated under vacuum to give 0.069 g of a colorless oil.

EI mz 498 (M⁺), 439 (M−CO₂CH₃⁺), 153 ($C_9H_7F_2^+$).

$[\alpha]_D^{20}$−11.6+/−0.4 [methanol (c=0.5), 589 nm].

The enantiomer B (dextrorotatory), having an undetermined absolute configuration, eluted in the second position, is recovered and then concentrated under vacuum to give 0.067 g of a colorless oil.

EI mz 498 (M⁺), 439 (M−CO₂CH₃⁺), 153 ($C_9H_7F_2^+$).

$[\alpha]_D^{20}$−11.5+/−0.4 [methanol (c=0.5), 589 nm].

Methyl (±)-1-[(2E)-3-(2,5-difluorophenyl)-2-propenyl]-3-[3-(3-fluoro-6-methoxyquinolin-4-yl)propyl]-3-pyrrolidinecarboxylate may be prepared as described in Example 2.

EXAMPLE 7

Enantiomer A of 4-[2-[(2,5-difluorophenyl)thio]ethyl]-2-[3-(3-fluoro-6-methoxyquinolin-4-yl)propyl]-2-morpholinecarboxylic acid (undetermined absolute configuration)

A solution of 0.21 g of enantiomer A of methyl 4-[2-[2,5-difluorophenyl)thio]ethyl]-2-[3-(3-fluoro-6-methoxy-4-quinolin-4-yl)propyl]-2-morpholinecarboxylate in a mixture of 10 cm³ of 1,4-dioxane, 10 cm³ of methanol and 1.18 cm³ of 5 N sodium hydroxide is heated at a temperature in the region of 80° C., with stirring and under an inert atmosphere, for 12 hours. After cooling to about 20° C., the reaction medium is evaporated under reduced pressure (2 kPa; 45° C.) to give a whitish crust. The residue is taken up in 25 cm³ of dichloromethane and 10 cm³ of distilled water and then neutralized with 1.2 cm³ of 5 N hydrochloric acid. The organic phase is dried over magnesium sulfate, filtered and then evaporated to dryness under reduced pressure (2 kPa) at a temperature in the region of 30° C. The residue obtained is purified by chromatography on a silica gel column (particle size 70–200 μm, diameter 2 cm), eluting with a chloroform-methanol-aqueous ammonia (28%) (12/3/0.5 by volume) mixture and collecting 10 cm³ fractions. The fractions containing the expected product are combined and then evaporated according to the conditions described above. 0.18 g of the enantiomer A of 4-[2-[(2,5-difluorophenyl)thio]ethyl]-2-[3-(3-fluoro-6-methoxyquinolin-4-yl)propyl]-2-morpholinecarboxylic acid in the form of a white solid.

¹H NMR spectrum (300 MHz, $(CD_3)_2SO$ d6 with addition of a few drops of $CD_3COOD$ d4, δ in ppm): from 1.45 to 1.90 (mt: 4H); 2.04 (d, J=11 Hz: 1H); 2.12 (broad t, J=11 Hz: 1H); from 2.40 to 2.60 (mt: 2H); 2.63 (broad d, J=11 Hz: 1H); from 2.95 to 3.05 (mt: 2H); 3.04 (t, J=7.5 Hz: 2H); 3.12 (d, J=11 Hz: 1H); 3.52 (very broad d, J=11 Hz: 1H); 3.77

(broad t, J=11 Hz: 1H); 3.85 (s: 3H); 7.20 (mt: 1H); from 7.30 to 7.50 (mt: 2H); from 7.50 to 7.60 (mt: 2H); 8.08 (d, J=9 Hz: 1H); 8.73 (broad s: 1H).

$\alpha_D^{20}$=−12.7°+/−0.6 in methanol at 0.5%.

EXAMPLE 8

Enantiomer B of 4-[2-[(2,5-difluorophenyl)thio]ethyl]-2-[3-(3-fluoro-6-methoxyquinolin-4-yl)propyl]-2-morpholinecarboxylic acid (undermined absolute configuration)

A solution of 0.22 g of the enantiomer B of methyl 4-[2-[(2,5-difluorophenyl)thio]ethyl]-2-[3-(3-fluoro-6-methoxyquinolin-4-yl)propyl]-2-morpholinecarboxylate in a mixture of 10 cm³ of 1,4-dioxane, 10 cm³ of methanol and 1.23 cm³ of 5 N sodium hydroxide is heated at a temperature in the region of 80° C. with stirring and under an inert atmosphere for 12 hours. After cooling to about 20° C., the reaction medium is evaporated under reduced pressure (2 kPa; 45° C.) to give a whitish crust. The residue is taken up in 25 cm³ of dichloromethane and 10 cm³ of distilled water and then neutralized with 1.2 cm³ of 5 N hydrochloric acid and extracted with 25 cm³ of diethyl ether. The organic phase is dried over magnesium sulfate, filtered and then evaporated to dryness under reduced pressure (2 kPa) at a temperature in the region of 30° C. The residue obtained is purified by chromatography on a silica gel column (particle size 70–200 μm; diameter 2 cm), eluting with a chloroform-methanol-aqueous ammonia (28%) (12/3/0.5 by volume) mixture and collecting 10 cm³ fractions. The fractions containing the expected product are combined and then evaporated according to the conditions described above. 0.2 g of the enantiomer B of 4-[2-[(2,5-difluorophenyl)thio]ethyl]-2-[3-(3-fluoro-6-methoxyquinolin-4-yl)propyl]-2-morpholinecarboxylic acid is obtained in the form of a white solid.

¹H NMR spectrum (300 MHz, (CD₃)₂SO d6, δ in ppm): from 1.50 to 1.85 (mt: 4H); 1.96 (d, J=11 Hz: 1H); 2.08 (broad t, J=11 Hz: 1H); from 2.45 to 2.55 (mt: 2H); 2.60 (broad d, J=11 Hz: 1H); 3.07 (mt: 2H); 3.10 (t, J=7.5 Hz: 2H); from 3.10 to 3.20 (mt: 2H); 3.54 (very broad d, J=11 Hz: 1H); 3.91 (broad t, J=11 Hz: 1H); 3.98 (s: 3H); 7.07 (mt: 1H); from 7.20 to 7.35 (mt: 2H); from 7.35 to 7.45 (mt: 2H); 7.96 (d, J=9 Hz: 1H); 8.68 (s: 1H).

$\alpha_D^{20}$=+16.0°+/−0.5 in methanol at 0.5%.

Preparation of the enantiomers A and B of methyl 4-[2-[(2,5-difluorophenyl)thio]ethyl]-2-[3-(3-fluoro-6-methoxyquinolin-4-yl)propyl]-2-morpholinecarboxylate:

A mixture of 0.7 g of methyl (±)-2-[3-(3-fluoro-6-methoxyquinolin-4-yl)propyl]-2-morpholinecarboxylate (racemic mixture of the enantiomers A and B), 0.59 g of 2-(2-bromoethyl)thio]-1,4-difluorobenzene, 0.32 g of potassium iodide and 1.33 g of potassium carbonate in 45 cm³ of acetonitrile is heated, with stirring and under an inert atmosphere, for 20 hours at a temperature in the region of 75° C. After cooling to a temperature in the region of 20° C., the reaction medium is filtered and the insoluble matter is washed with twice 10 cm³ of acetonitrile. The filtrate is evaporated under reduced pressure (2 kPa) at a temperature in the region of 40° C. The evaporation residue is taken up in 50 cm³ of distilled water and 100 cm³ of ethyl acetate. The organic phase is washed with 3 times 30 cm³ of distilled water and twice 50 cm³ of a saturated aqueous sodium chloride solution, dried over magnesium sulfate and evaporated according to the conditions described above. The oil obtained is purified by chromatography on a silica gel column (particle size 70–200 μm; diameter 2.5 cm), eluting with a mixture of dichloromethane-ethyl acetate (90/10 by volume) and collecting 10 cm³ fractions. The fractions containing the expected product are combined and then evaporated under reduced pressure (2 kPa) at a temperature in the region of 40° C. 0.52 g of methyl (±)-4-[2-(2,5-difluorophenyl)thio]ethyl]-2-[3-(3-fluoro-6-methoxyquinolin-4-yl)propyl]-2-morpholinecarboxylate is obtained in the form of a colorless thick oil (racemic mixture of the enantiomers A and B).

¹H NMR spectrum (300 MHz, (CD₃)₂SO d6, δ in ppm): from 1.40 to 1.60 (mt: 1); 1.73 (mt: 3H); 2.01 (d, J=11 Hz: 1H); 2.12 (split t, J=11 and 3.5 Hz: 1H); from 2.50 to 2.60 (mt: 2H); 2.64 (broad d, J=11 Hz: 1H); 3.06 (mt: 2H); 3.10 (t, J=7 Hz: 2H); 3.17 (broad d, J=11 Hz: 1H); 3.59 (s: 3H); 3.64 (very broad d, J=7 Hz: 1H); 3.81 (split t, J=11 and 3 Hz: 1H); 3.97 (s: 3H); 7.65 (mt: 1H); from 7.20 to 7.35 (mt: 2H); 7.36 (d, J=3 Hz: 1H); 7.40 (dd, J=9 and 3 Hz: 1H); 7.96 (d, J=9 Hz: 1H); 8.68 (broad s: 1H).

1-[(2-Bromoethyl)thio]-(2,5-difluoro)benzene is prepared according to the method described in patent application WO 02/40474.

Starting with the racemic mixture of the enantiomers A and B obtained above, the separation of each enantiomer is carried out by HPLC.

The separation of the 2 enantiomers A and B is carried out on a stationary phase Chiracel OD TM C18 starting with 0.52 g of the mixture A, B described above, particle size 20 μm; diameter 80 mm and having a length of 350 mm; mass of the stationary phase 1200 g), the mobile phase is composed of a mixture of heptane/ethanol/triethylamine (95/05/0.05 by volume) having a flow rate of 110 cm³ per minute and the wavelength of the UV detector is set at 265 nm.

The fractions containing the first enantiomer (enantiomer A) eluted in the first position, the levorotatory, are combined and evaporated under reduced pressure (2 kPa) at a temperature in the region of 40° C. to give 0.224 g of a colorless oil. The fractions containing the second enantiomer (enantiomer B) eluted in the second position, the dextrorotatory, are combined and evaporated under reduced pressure (2 kPa) at a temperature in the region of 40° C. to give 0.236 g of a colorless oil.

Enantiomer A

¹H NMR spectrum (300 MHz, (CD₃)₂SO d6, δ in ppm): from 1.40 to 1.60 (mt: 1H); 1.73 (mt: 3H); 2.01 (d, J=11 Hz: 1H); 2.12 (split t, J=11 and 3.5 Hz: 1H); from 2.50 to 2.60 (mt: 2H); 2.64 (broad d, J=11 Hz: 1H); 3.05 (mt: 2H); 3.10 (t, J=7 Hz: 2H); 3.17 (broad d, J=11 Hz: 1H); 3.59 (s: 3H); 3.64 (very broad d, J=11 Hz: 1H); 3.81 (split t, J=11 and 3 Hz: 1H); 3.97 (s: 3H); 7.05 (mt: 1H); from 7.20 to 7.35 (mt: 2H); 7.36 (d, J=3 Hz: 1H); 7.40 (dd, J=9 and 3 Hz: 1H); 7.96 (d, J=9 Hz: 1H); 8.68 (broad s: 1H).

$\alpha_D^{20}$=−17.5°+/− in DMSO at 0.6%.

Enantiomer B

¹H NMR spectrum (300 MHz, (CD₃)₂SO d6, δ in ppm): from 1.40 to 1.60 (mt: 1H); 1.73 (mt: 3H); 2.01 (d, J=11 Hz: 1H); 2.12 (split t, J=11 and 3.5 Hz: 1H); from 2.50 to 2.60 (mt: 2H); 2.64 (broad d, J=11 Hz: 1H); 3.06 (mt: 2H); 3.10 (t, J=7 Hz: 2H); 3.17 (broad d, J=11 Hz: 1H); 3.59 (s: 3H); 3.64 (very broad d, J=11 Hz: 1H); 3.81 (split t, J=11 and 3 Hz: 1H); 3.97 (s: 3H); 7.05 (mt: 1H); from 7.20 to 7.35 (mt: 2H); 7.36 (d, J=3 Hz: 1H); 7.40 (dd, J=9 and 3 Hz: 1H); 7.96 (d, J=9 Hz: 1H); 8.68 (broad s: 1H).

$\alpha_D^{20}$=+24.1°+/−0.9% in DMSO at 0.5%.

Methyl (±)-2-[3-(3-fluoro-6-methoxyquinolin-4-yl)propyl]-2-morpholinecarboxylate 17.3 cm³ of 4 N hydrochloric dioxane are added to a solution of 3.2 g of 4-(1,1-dimethylethyl) and 2-methyl (±)-2-[3-(3-fluoro-6-methoxyquinolin-4-yl)propyl]-2,4-morpholinedicarboxylate in 70 cm³ of dioxane, and then the medium is stirred at 20° C. for 16 hours. The reaction medium is then evaporated under reduced pressure (45° C.; 5 kPa). The residue is taken up in 30 cm³ of ethyl acetate and 20 cm³ of distilled water and then neutralized with a saturated sodium bicarbonate solution. The organic phase is dried over magnesium sulfate, filtered and then evaporated to dryness under reduced pressure (2 kPa) at a temperature in the region of 40° C. The residue obtained is purified by chromatography on a silica gel column (particle size 70–200 μm; diameter 2.5 cm), eluting with a mixture of dichloromethane-methanol (95/5 by volume) and collecting 10 cm³ fractions. The fractions containing the expected product are combined and then evaporated according to the conditions described above. 1.8 g of methyl (±)-2-[3-(3-fluoro-6-methoxyquinolin-4-yl)propyl]-2-morpholinecarboxylate are obtained in the form of a thick brown oil.

¹H NMR spectrum (300 MHz, $(CD_3)_2SO$ d6, δ in ppm): from 1.35 to 1.60 (mt: 1H; 1.69 (mt: 3H); from 2.55 to 2.70 (mt: 1H); 3.04 (mt: 2H); 3.19 (mt: 2H); from 3.30 to 3.35 (mt: 1H); 3.55 (very broad d, J=11 Hz: 1H); 3.60 (s: 3H); 3.70 (mt: 1H); 3.97 (s: 3H); 7.36 (d, J=3 Hz: 1H); 7.40 (dd, J=9 and 3 Hz: 1H); 7.96 (d, J=9 Hz: 1H); 8.68 (broad s: 1H).

4-(1,1-dimethylethyl) and 2-methyl (±)-2-[3-(3-fluoro-6-methoxyquinolin-4-yl)-propyl]-2,4-morpholinedicarboxylate 32 cm³ of a 0.5 M solution of 9-borabicyclo[3.3.1]nonane in tetrahydrofuran are added dropwise to a solution of 3.9 g of 4-(1,1-dimethylethyl) and 2-methyl (±)-2-(2-propenyl)-2,4-morpholinedicarboxylate in 40 cm³ of tetrahydrofuran with stirring and under an inert atmosphere and after cooling to −10° C. The mixture is then brought to a temperature in the region of 20° C. while the stirring is continued for another 4 hours. 4.35 g of 4-iodo-3-chloro-6-methoxyquinoline in solution in 30 cm³ of tetrahydrofuran are added over 45 minutes, followed by 260 mg of diphenylphosphinoferrocenepalladium chloride and finally 7.54 g of tribasic potassium phosphate. The reaction mixture is heated under reflux for 15 hours and then filtered in the hot state on sintered glass. The filtrate is taken up in 4 times 20 cm³ of ethyl acetate and concentrated to dryness under reduced pressure (40° C.; 5 kPa). The residue is taken up in 250 cm³ of ethyl acetate and 200 cm³ of water. The organic phase is separated by decantation, washed with 3 times 50 cm³ of distilled water and with twice 100 cm³ of a saturated aqueous sodium chloride solution, dried over magnesium sulfate, filtered and then concentrated under reduced pressure (45° C.; 5 kPa). The residue is purified by chromatography on a silica gel column (particle size 70–200 μm; diameter 2.8 cm), eluting with dichloromethane and then with a mixture of dichloromethane-ethyl acetate (90/10 by volume) and collecting 200 cm³ fractions. The fractions containing the product are combined and then concentrated under reduced pressure (40° C.; 5 kPa). 3.22 g of 4-(1,1-dimethylethyl) and 2-methyl (±)-2-[3-(3-fluoro-6-methoxyquinolin-4-yl)propyl]-2,4-morpholinedicarboxylate are obtained in the form of a yellow viscous oil.

¹H-NMR spectrum (300 MHz, $(CD_3)_2SO$ d6, δ in ppm): from 1.35 to 1.85 (mt: 4H); 1.38 (s: 9H); from 2.85 to 3.05 (mt: 1H); 3.07 (mt: 2H); 3.61 (s: 3H); 3.67 (mt: 4H); 3.97 (s: 3H); 4.17 (d, J=13.5 Hz: 1H); from 7.35 to 7.45 (mt: 2H); 7.97 (d, J=9 Hz: 1H); 8.69 (broad s: 1H).

4-(1,1-Dimethylethyl) and 2-methyl (±)-2-(2-propenyl)-2,4-morpholinedicarboxylate (racemate)

15 cm³ of a 1.6 M solution of butyllithium in hexane are added dropwise to a solution of 3.7 cm³ of diisopropylamine in 50 cm³ of tetrahydrofuran with stirring and under an inert atmosphere and after cooling to −70° C. The mixture is stirred at this temperature for 70 minutes. 5 g of 4-(1,1-dimethylethyl) and 2-methyl 2,4-morpholinedicarboxylate in solution in 40 cm³ of tetrahydrofuran are added dropwise over 40 minutes. The mixture is stirred at this same temperature for 40 minutes. 3.2 g of -2-propenyl bromide in solution in 10 cm³ of THF are added dropwise over 25 minutes. The mixture is stirred at this same temperature for 70 minutes. The mixture is then brought to a temperature in the region of 20° C. while the stirring is continued for another 2 hours. 15 cm³ of a saturated ammonium chloride solution are added dropwise. The temperature rises to 25° C. The organic phase is separated by decantation, washed with once 50 cm³ of distilled water and with twice 100 cm³ of a saturated aqueous sodium chloride solution, dried over magnesium sulfate, filtered and then concentrated under reduced pressure (45° C.; 5 kPa). The residue is purified by chromatography on a silica gel column (particle size 70–200 μm; diameter 2.8 cm), eluting with dichloromethane and collecting 50 cm³ fractions. The fractions containing the product are combined and then concentrated under reduced pressure (45° C.; 5 kPa). 3.5 g of 4-(1,1-dimethylethyl) and 2-methyl (±)-2-(2-propenyl)-2,4-morpholinedicarboxylate are obtained in the form of a colorless oil.

¹H NMR spectrum (300 MHz, $(CD_3)_2SO$ d6, δ in ppm): 1.40 (s: 9H); 2.38 (d, J=7.5 Hz: 2H); from 2.80 to 3.05 (mt: 2H); from 3.55 to 3.80 (mt: 3H); 3.66 (s: 3H); 4.20 (d, J=13 Hz: 1H); from 5.00 to 5.20 (mt: 2H); 5.70 (mt: 1H).

4-(1,1-Dimethylethyl) and 2-methyl (±)-2,4-morpholinedicarboxylate 13.5 cm³ of iodomethane and then 7 g of cesium carbonate are added to a solution of 10 g of 4-(1,1-dimethylethyl) 2,4-morpholinedicarboxylate in 200 cm³ of acetonitrile with stirring and under an inert atmosphere, at a temperature in the region of 20° C. The mixture is stirred at this same temperature for 24 hours. The mixture is then filtered on Celite and the filtrate is concentrated to dryness under reduced pressure (45° C.; 5 kPa). The residue is taken up in 250 cm³ of dichloromethane and 200 cm³ of water. The organic phase is separated by decantation, washed with 3 times 50 cm³ of distilled water and with twice 100 cm³ of a saturated aqueous sodium chloride solution, dried over magnesium sulfate, filtered and then concentrated under reduced pressure (35° C.; 5 kPa). 5 g of 4-(1,1-dimethylethyl) and 2-methyl 2,4-morpholinedicarboxylate are obtained in the form of a yellow viscous oil which crystallizes slowly. Melting point is 68° C.

¹H NMR spectrum (400 MHz, $(CD_3)_2SO$ d6 at a temperature of 373K, δ in ppm): 1.45 (s: 9H); 3.18 (split dd, J=13.5–9 and 3 Hz: 1H); 3.28 (dd, J=13.5 and 8 Hz: 1H); 3.53 (mt: 2H); 3.71 (s: 3H); 3.80 (dd, J=13.5 and 3 Hz: 1H); 3.89 (dt, J=11 and 4 Hz: 1H); 4.17 (dd, J=8 and 3 Hz: 1H).

EXAMPLE 9

Enantiomer A of 4-[3-(2,5-difluorophenyl)-2-propenyl]-2-[3-(3-fluoro-6-methoxyquinolin-4-yl)propyl]-2-morpholinecarboxylic acid (undetermined absolute configuration)

A solution of 0.21 g of the enantiomer A of methyl 4-[3-(2,5-difluorophenyl)-2-propenyl]-2-[3-(3-fluoro-6- methoxyquinolin-4-yl)propyl]-2-morpholinecarboxylate in a mixture of 10 cm³ of 1,4-dioxane, 10 cm³ of methanol and 1.22 cm³ of 5 N sodium hydroxide is heated at a temperature in the region of 80° C. with stirring and under an inert atmosphere for 12 hours. After cooling to about 20° C., the reaction medium is evaporated under reduced pressure (2 kPa; 45° C.) to give a whitish crust. The residue is taken up in 25 cm³ of dichloromethane and then 10 cm³ of distilled water and then neutralized with 1.23 cm³ of 5 N hydrochloric acid. The organic phase is dried over magnesium sulfate, filtered and then evaporated to dryness under reduced pressure (2 kPa) at a temperature in the region of 30° C. The residue obtained is purified by chromatography on a silica gel column (particle size 70–200 µm; diameter 2 cm), eluting with a mixture of chloroform-methanol-aqueous ammonia (28%) (12/3/0.5 by volume) and collecting 10 cm³ fractions. The fractions containing the expected product are combined and then evaporated according to the conditions described above. 0.13 g of the enantiomer A of 4-[3-(2,5-difluorophenyl)-2-propenyl]-2-[3-(3-fluoro-6-methoxyquinolin-4-yl)propyl]-2-morpholinecarboxylic acid is obtained in the form of a yellow glaze.

$^1$H NMR spectrum (300 MHz, (CD$_3$)$_2$SO d6, δ in ppm): from 1.45 to 1.60 (mt: 1H); from 1.65 to 1.90 (mt: 3H); 1.95 (d, J=11 Hz: 1H); 2.09 (split t, J=11 and 3.5 Hz: 1H); 2.63 (broad d, J=11 Hz: 1H); from 2.95 to 3.15 (mt: 4H); 3.17 (broad d, J=11 Hz: 1H); 3.63 (very broad d, J=11 Hz: 1H); 3.90 (very broad t, J=11 Hz: 1H); 3.96 (s: 3H); 6.41 (dt, J=7 and 16.5 Hz: 1H); 6.62 (broad d, J=16.5 Hz: 1H); 7.13 (mt: 1H); 7.24 (split t, J=10 and 4.5 Hz: 1H); 7.39 (mt: 2H); 7.48 (mt: 1H); 7.96 (d, J=10 Hz: 1H); 8.68 (s: 1H).

$α_D^{20}$=−12.6°+/−0.7 in methanol at 0.5%.

EXAMPLE 10

Enantiomer B of 4-[3-(2,5-difluorophenyl)-2-propenyl]-2-[3-(3-fluoro-6-methoxyquinolin-4-yl)propyl]-2-morpholinecarboxylic acid (undetermined absolute configureation)

A solution of 0.21 g of the enantiomer B of methyl 4-[3-(2,5-difluorophenyl)-2-propenyl]-2-[3-(3-fluoro-6-methoxyquinolin-4-yl)propyl]-2-morpholine-carboxylate in a mixture of 10 cm³ of 1,4-dioxane, 10 cm³ of methanol and 1.22 cm³ of 5 N sodium hydroxide is heated at a temperature in the region of 80° C. with stirring and under an inert atmosphere for 12 hours. After cooling to about 20° C., the reaction medium is evaporated under reduced pressure (2 kPa; 45° C.) to give a whitish crust. The residue is taken up in 25 cm³ of dichloromethane and 10 cm³ of distilled water and then neutralized with 1.2 cm³ of 5 N hydrochloric acid. The organic phase is dried over magnesium sulfate, filtered and then evaporated to dryness under reduced pressure (2 kPa) at a temperature in the region of 30° C. The residue obtained is purified by chromatography on a silica gel column (particle size 70–200 µm; diameter 2 cm), eluting with a mixture of chloroform-methanol-aqueous ammonia (28%) (12/3/0.5 by volume) and collecting 10 cm³ fractions. The fractions containing the expected product are combined and then evaporated according to the conditions described above. 0.14 g of the enantiomer B of 4-[3-(2,5-difluorophenyl)-2-propenyl]-2-[3-(3-fluoro-6-methoxyquinolin-4-yl)propyl]-2-morpholinecarboxylic acid is obtained in the form of a thick orange oil.

$^1$H NMR spectrum (300 MHz, (CD$_3$)$_2$SO d6, δ in ppm): from 1.45 to 1.60 (mt: 1H); from 1.65 to 1.85 (mt: 3H); 1.95 (d, J=11 Hz: 1H); 2.09 (split t, J=11 and 2.5 Hz: 1H); 2.62 (broad d, J=11 Hz: 1H); from 2.95 from 3.15 (mt: 4H); 3.17 (broad d, J=11 Hz: 1H); 3.62 (broad d, J=11 Hz: 1H); 3.91 (very broad t, J=11 Hz: 1H); 3.96 (s: 3H); 6.40 (dt, J=16 and 7 Hz: 1H); 6.62 (broad d, J=16 Hz: 1H); 7.13 (mt: 1H); 7.24 (split t, J=10 and 5 Hz: 1H); 7.39 (mt: 2H); 7.48 (mt: 1H); 7.96 (d, J=10 Hz: 1H); 8.68 (broad s: 1H).

$α_D^{20}$=+12.4°+/−0.6 in methanol at 0.5%.

Preparation of the enantiomers A and B of methyl 4-[3-(2,5-difluorophenyl)-2-propenyl]-2-[3-(3-fluoro-6-methoxyquinolin-4-yl)propyl]-2-morpholine-carboxylate:

A solution of 0.62 g of benzotriazole and 0.62 g of thionyl chloride in solution in 30 cm³ of chloroform is added dropwise to 0.7 g of 2,5-difluorocinnamyl alcohol solubilized in 90 cm³ of chloroform, with stirring and under an inert atmosphere, at a temperature in the region of 23° C. The mixture is then stirred at this same temperature for 2 hours. The reaction mixture is taken up in 75 cm³ of a saturated sodium bicarbonate solution, and then with 75 cm³ of distilled water and finally dried over magnesium sulfate to give a yellow solution S. This solution S is added to a mixture of 1.1 g of methyl 2-[3-(3-fluoro-6-methoxyquinolin-4-yl)propyl]-2-morpholinecarboxylate, 0.5 g of potassium iodide and 2.1 g of potassium carbonate in 150 cm³ of acetonitrile and then the whole is heated with stirring and under an inert atmosphere for 20 hours at a temperature in the region of 75° C. After cooling to a temperature in the region of 20° C., the reaction medium is filtered and the insoluble matter is washed with twice 10 cm³ of acetonitrile. The filtrate is evaporated under reduced pressure (2 kPa) at a temperature in the region of 40° C. The evaporation residue is taken up in 50 cm³ of distilled water and 100 cm³ of ethyl acetate. The organic phase is washed with 3 times 30 cm³ of distilled water and twice 50 cm³ of a saturated aqueous sodium chloride solution, dried over magnesium sulfate and evaporated according to the conditions described above. The oil obtained is purified by chromatography on a silica gel column (particle size 70–200 µm; diameter 2.5 cm), eluting with a mixture of dichloromethane-ethyl acetate (80/20 by volume) and collecting 10 cm³ fractions. The fractions containing the expected product are combined and then evaporated under reduced pressure (2 kPa) at a temperature in the region of 40° C. 0.48 g of methyl 4-[3-(2, 5-difluorophenyl)-2-propenyl]-2-[3-(3-fluoro-6-methoxyquinolin-4-yl)propyl]-2-morpholinecarboxylate is obtained in the form of a brown gum (racemic mixture of the enantiomers A and B).

$^1$H NMR spectrum (300 MHz, (CD$_3$)$_2$SO d6, δ in ppm): from 1.40 to 1.60 (mt: 1H); 1.73 (mt: 3H); 1.99 (d, J=11 Hz: 1H); 2.12 (split t, J=11 and 3.5 Hz: 1H); 2.64 (broad d, J=11 Hz: 1H); 3.05 (mt: 2H); from 3.05 to 3.15 (mt: 2H); 3.18 (broad d, J=11 Hz: 1H); 3.61 (s: 3H); 3.67 (very broad d, J=11 Hz: 1H); 3.83 (split t, J=11 and 2.5 Hz: 1H); 3.96 (s: 3H); 6.39 (dt, J=16.5 and 7 Hz: 1H); 6.61 (broad d, J=16.5 Hz: 1H); 7.13 (mt: 1H); 7.24 (split t, J=10 and 5 Hz: 1H); 7.36 (d, J=3 Hz: 1H); 7.40 (dd, J=9 and 3 Hz: 1H); 7.49 (mt: 1H); 7.96 (d, J=9 Hz: 1H); 8.68 (broad s: 1H).

Starting with the racemic mixture of the enantiomers A and B obtained above, the separation of each enantiomer is carried out by HPLC.

The separation of the 2 enantiomers A and B is carried out on a stationary phase Chiracel OD TM C18 starting with 0.52 g of the mixture A, B described above, particle size 20 µm; diameter 80 mm and having a length of 350 mm; mass of the stationary phase 1200 g, the mobile phase is composed of a mixture of heptane/methanol/propanol (95/01/04 by volume) having a flow rate of 100 cm³ per minute and the UV detector wavelength is set at 254 nm.

The fractions containing the first enantiomer eluted in the first position (called enantiomer A), the levorotatory, are combined and evaporated under reduced pressure (2 kPa) at a temperature in the region of 40° C. to give 0.217 g of a colorless oil.

The fractions containing the second enantiomer eluted in the second position (called enantiomer B), the dextrorotatory, are combined and evaporated under reduced pressure (2 kPa) at a temperature in the region of 40° C. to give 0.212 g of a colorless oil.

Enantiomer A $^1$H NMR spectrum (300 MHz, (CD$_3$)$_2$SO d6, δ in ppm): from 1.40 to 1.60 (mt: 1H); 1.73 (mt: 3H); 1.99 (d, J=11 Hz: 1H); 2.12 (split t, J=11 and 3.5 Hz: 1H); 2.64 (broad d, J=11 Hz: 1H); 3.05 (mt: 2H); from 3.05 to 3.15 (mt: 2H); 3.18 (d, J=11 Hz: 1H); 3.61 (s: 3H); 3.67 (very broad d, J=11 Hz: 1H); 3.83 (split t, J=11 and 2.5 Hz: 1H); 3.96 (s: 3H); 6.39 (dt, J=16 and 6.5 Hz: 1H); 6.61 (broad d, J=16 Hz: 1H); 7.13 (mt: 1H); 7.24 (split t, J=10 and 4.5 Hz: 1H); 7.36 (d, J=3 Hz: 1H); 7.40 (dd, J=9 and 3 Hz: 1H); 7.49 (mt: 1H); 7.96 (d, J=9 Hz: 1H); 8.68 (s: 1H).

Enantiomer B $^1$H NMR spectrum (300 MHz, (CD$_3$)$_2$SO d6, δ in ppm): from 1.40 to 1.60 (mt: 1H); 1.73 (mt: 3H); 1.99 (d, J=11 Hz: 1H); 2.12 (split t, J=11 and 3.5 Hz: 1H); 2.64 (broad d, J=11 Hz: 1H); 3.05 (mt: 2H); from 3.05 to 3.15 (mt: 2H); 3.18 (broad d, J=11 Hz: 1H); 3.61 (s: 3H); 3.67 (very broad d, J=11 Hz: 1H); 3.83 (split t, J=11 and 2.5 Hz: 1H); 3.96 (s: 3H); 6.39 (dt, J=16 and 7 Hz: 1H); 6.61 (broad d, J=16 Hz: 1H); 7.13 (mt: 1H); 7.24 (split t, J=10 and 5 Hz: 1H); 7.36 (d, J=3 Hz: 1H); 7.40 (dd, J=9 and 3 Hz: 1H); 7.49 (mt: 1H); 7.96 (d, J=9 Hz: 1H); 8.68 (s: 1H).

EXAMPLE 11

1-[(2E)-3-(2,5-difluorophenyl)-2-propenyl]-3-[3-(3-fluoro-6-methoxyquinolin-4-yl)propyl]-3-azetidinecarboxylic acid 5 cm$^3$ of a 5 N aqueous sodium hydroxide solution are added at a temperature in the region of 20° C. to 614 mg (1.267 mmol) of methyl 1-[(2E)-3-(2,5-difluorophenyl)-2-propenyl]-3-[3-(3-fluoro-6-methoxyquinolin-4-yl)propyl]azetidine-3-carboxylate in solution in 20 cm$^3$ of dioxane. After stirring under reflux for 1.5 hours, 6 cm$^3$ of a 5 N aqueous sodium hydroxide solution are again added, and the medium is kept under reflux for another 3 hours; the reaction medium is cooled and supplemented with 4.5 cm$^3$ of hydrochloric acid at 37%, and then concentrated to dryness under reduced pressure (2.7 kPa) to give a residue which is flash-chromatographed on a 200 cm$^3$ column of fine silica [eluent: solvent gradient (dichloromethane-methanol-aqueous ammonia at 28%) (from 100-0-0 to 72-24-4 by volume)]. The fractions containing the product are combined and evaporated to dryness (2.7 kPa). The residue (530 mg) is taken up in 10 cm$^3$ of dichloromethane, diluted with 25 cm$^3$ of diethyl ether to give 445 mg of 1-[(2E)-3-(2,5-difluorophenyl)-2-propenyl]-3-[3-(3-fluoro-6-methoxyquinolin-4-yl)propyl]-3-azetidinecarboxylic acid in the form of a slightly pink solid melting at 211° C.

$^1$H NMR spectrum (300 MHz, (CD$_3$)$_2$SO d6, δ in ppm): 1.60 (mt: 2H); 1.99 (mt: 2H); from 2.95 to 3.55 (mt: 2H); 3.09 (d, J=7 Hz: 2H); 3.19 (broad d, J=5.5 Hz: 2H); 3.37 (d, J=7 Hz: 2H); 3.96 (s: 3H); 6.35 (dt, J=16.5 and 5.5 Hz: 1H); 6.57 (broad d, J=16.5 Hz: 1H); 7.13 (mt: 1H); 7.25 (split t, J=9.5 and 5 Hz: 1H); from 7.35 to 7.45 (mt: 2H); 7.49 (ddd, J=9.5–6 and 3 Hz: 1H); 7.96 (d, J=9 Hz: 1H); 8.70 (broad s: 1H).

CI mass spectrum: m/z 471 (M+H)$^+$ (base peak).

Methyl 1-[(2E)-3-(2,5-difluorophenyl)-2-propenyl]-3-[3-(3-fluoro-6-methoxyquinolin-4-yl)propyl]-3-azetidinecarboxylate may be prepared as described in Example 12.

EXAMPLE 12

Methyl 1-[(2E)-3-(2,5-difluorophenyl)-2-propenyl]-3-[3-(3-fluoro-6-methoxyquinolin-4-yl)propyl]-3-azetidinecarboxylate 2 g of potassium carbonate, 0.531 g of potassium iodide and then a freshly prepared solution of 2-[(1E)-3-chloropropenyl]-1,4-difluorobenzene (3.8 mmol) in solution in 70 cm$^3$ of acetonitrile are added at a temperature in the region of 20° C. under an argon atmosphere to 1.18 g (2.91 mmol) of methyl 3-[3-(3-fluoro-6-methoxyquinolin-4-yl)propyl]-3-azetidinecarboxylate dihydrochloride. After stirring under reflux for 3 hours, the reaction mixture is concentrated to dryness under reduced pressure (2.7 kPa) to give a residue which is taken up in 100 cm$^3$ of water, extracted with 6 times 100 cm$^3$ of dichloromethane which is concentrated to dryness under reduced pressure (2.7 kPa) to give 1.546 g of a brown oil which is purified by flash chromatography on 240 ml of fine silica [eluent: gradient of cyclohexane/ethyl acetate (from 50-50 to 40-60 by volume)]. After concentrating the fractions under reduced pressure, 0.799 g of methyl 1-[(2E)-3-(2,5-difluorophenyl)-2-propenyl]-3-[3-(3-fluoro-6-methoxyquinolin-4-yl)propyl]azetidine-3-carboxylate is obtained in the form of a yellow oil.

$^1$H NMR spectrum (300 MHz, (CD$_3$)$_2$SO d6, δ in ppm): 1.57 (mt: 2H); 2.00 (mt: 2H); from 3.00 to 3.15 (mt: 2H); 3.10 (d, J=7.5 Hz: 2H); 3.17 (broad d, J=6 Hz: 2H); 3.38 (d, J=6 Hz: 2H); 3.60 (s: 3H); 3.96 (s: 3H); 6.35 (dt, J=16.5 Hz: 1H); 6.55 (broad d, J=16.5 Hz: 1H); 7.12 (mt: 1H); 7.24 (split t, J=9.5 and 5 Hz: 1H); from 7.30 to 7.45 (mt: 2H); 7.48 (ddd, J=9.5–6 and 3 Hz: 1H); 7.96 (d, J=9 Hz: 1H); 8.70 (d, J=1Hz: 1H).

EI mass spectrum: m/z 484 (M$^+$) m/z 191 (base peak).

The solution of 2-[(1E)-3-chloro-1-propenyl]-1,4-difluorobenzene (3.8 mmol) in acetonitrile may be prepared in the following manner:

A solution of 0.34 cm$^3$ (4.66 mmol) of thionyl chloride and 0.555 g (4.66 mmol) of benzotriazole in 40 cm$^3$ of dichloromethane is added at a temperature in the region of 20° C. under an argon atmosphere to 0.646 g (3.8 mmol) of 2,5-difluorocinnamyl alcohol in solution in 40 cm$^3$ of dichloromethane. After stirring for 10 minutes, the reaction mixture is filtered on No. 3 sintered glass and the solid residue rinsed with twice 10 cm$^3$ of dichloromethane. The filtrate is washed 3 times with 30 cm$^3$ of water. The organic phase is dried over magnesium sulfate and filtered to give a solution of 2-[(1E)-3-chloro-1-propenyl]-1,4-difluorobenzene (3.8 mmol) which is then concentrated to dryness under reduced pressure (2.7 kPa) at a temperature in the region of 20° C., before dissolution in acetonitrile.

Methyl 3-[3-(3-fluoro-6-methoxyquinolin-4-yl)propyl]-3-azetidinecarboxylate dihydrochloride may be prepared in the following manner:

10 cm$^3$ of a 4 N hydrochloric acid solution in dioxane are added at a temperature in the region of 20° C. to 1.325 g (3.06 mmol) of 1-(1,1-dimethylethyl) and 3-methyl 3-[3-(3-fluoro-6-methoxyquinolin-4-yl)propyl]1,3-azetidinedicarboxylate in solution in 10 cm$^3$ of methanol. After stirring for 4 hours at a temperature in the region of 20° C., the reaction mixture is concentrated to dryness under reduced pressure (2.7 kPa) to give 1.19 g of methyl 3-[3-(3-fluoro-6-methoxyquinolin-4-yl)propyl]-3-azetidinecarboxylate dihydrochloride in the form of a pale yellow foam.

EI mass spectrum: m/z 332 (M+), m/z 304, 204 (base peak), and 191.

1-(1,1-Dimethylethyl) and 3-methyl 3-[3-(3-fluoro-6-methoxyquinolin-4-yl)propyl]-1,3-azetidinedicarboxylate may be prepared in the following manner:

A solution of 1.021 g (4 mmol) of 1-(1,1-dimethylethyl) and 3-methyl 3-(2-propenyl)-1,3-azetidinedicarboxylate in 15 cm³ of tetrahydrofuran is added at a temperature in the region of 3° C., under an argon atmosphere, to 12 cm³ (6 mmol) of a 0.5 M solution of 9-BBN (9-borabicyclo[3.3.1] nonane)/THF. After heating the reaction mixture to a temperature in the region of 20° C. and then stirring for 3 hours at a temperature in the region of 20° C., 2.34 g (4.4 mmol) of 3-fluoro-4-iodo-6-methoxyquinoline in suspension in 35 cm³ of tetrahydrofuran and then 2.55 g (12 mmol) of potassium phosphate and 0.09 g (0.123 mmol) of PdCl$_2$dppf (1,1'-bis(diphenylphosphino)ferrocenepalladium dichloride) are successively added. After stirring for 19 hours at the reflux temperature, the reaction mixture is cooled and then filtered on sintered glass which is abundantly rinsed with tetrahydrofuran and ethyl acetate. The filtrate is then concentrated to dryness under reduced pressure (2.7 kPa) to give 3.09 g of a black oil which is purified by flash chromatography on 300 cm³ of fine silica [eluent: gradient of cyclohexane/ethyl acetate (from 75-25 to 60-40 by volume)]. After concentrating the fraction under reduced pressure, 1.334 g of 1-(1,1-dimethylethyl) and 3-methyl 3-[3-(3-fluoro-6-methoxyquinolin-4-yl)propyl]-1,3-azetidinedicarboxylate are obtained in the form of a yellow oil.

CI mass spectrum: m/z 433 (M+H)+ (base peak).

1-(1,1-Dimethylethyl) and 3-methyl 3-(2-propenyl)-1,3-azetidinedicarboxylate may be prepared in the following manner:

20 cm³ (20 mmol) of lithium bis(trimethylsilyl)amide as a 1 M solution in tetrahydrofuran are added dropwise at a temperature in the region of −78° C., under an argon atmosphere, to 3.601 g (16.73 mmol) of 1-(1,1-dimethylethyl) and 3-methyl 1,3-azetidinedicarboxylate in solution in 40 cm³ of tetrahydrofuran. After stirring for 10 minutes at a temperature in the region of −78° C., 2.2 cm³ (25.4 mmol) of -2-propenyl bromide are added and then the temperature is allowed to rise from −78° C. to a temperature in the region of 20° C., at which temperature the medium is stirred for another 17 hours. The reaction medium is then concentrated to dryness under reduced pressure (2.7 kPa). The residue is taken up in 50 cm³ of water and extracted with 3 times 50 cm³ of ethyl acetate, dried over anhydrous magnesium sulfate, filtered and then concentrated to dryness under reduced pressure (2.7 kPa) to give 3.525 g of a yellow oil which is purified by flash chromatography [eluent: gradient of cyclohexane/ethyl acetate (from 90-10 to 80-20 by volume)]. After concentrating the fractions under reduced pressure, 2.75 g of 1-(1,1-dimethylethyl) and 3-methyl 3-(2-propenyl)-1,3-azetidinedicarboxylate are obtained in the form of a colorless oil.

CI mass spectrum: m/z 256 (M+H)+, m/z 273 (M+NH$_4$)+ (base peak).

1-(1,1-Dimethylethyl) and 3-methyl 1,3-azetidinedicarboxylate may be prepared in the following manner:

0.9 cm³ (0.9 mmol) of a molar solution of tetrabutylammonium fluoride is added to a solution of 3.513 g (17.46 mmol) of 1-(1,1-dimethylethyl) 1,3-azetidinedicarboxylate in solution in 30 cm³ of methanol; the medium is cooled to a temperature in the region of 5° C., and then 10 cm³ (20 mmol) of a 2 M solution of trimethylsilyldiazomethane in hexane are then poured in over five minutes, and then after thirty minutes, another 15 cm³ (30 mmol) of a 2 M solution of trimethylsilyldiazomethane in hexane. After decolorization, the solvents are evaporated under reduced pressure (2.7 kPa) to give 4.205 g of a brown liquid which is purified by flash chromatography on 320 ml of fine silica [eluent: cyclohexane/ethyl acetate (80/20 by volume)]. After concentrating the fractions under reduced pressure, 3.456 g of 1-(1,1-dimethylethyl) and 3-methyl 1,3-azetidinedicarboxylate are obtained in the form of a colorless liquid.

CI mass spectrum: m/z 216 (M+H)+, m/z 233 (M+NH$_4$)+ (base peak).

EXAMPLE 13

Sodium salt of 3-[3-(3-fluoro-6-methoxyquinolin-4-yl) propyl]-1-[2-(2-thienylthio)ethyl]-3-azetidinecarboxylic acid The procedure is carried out as in Example 11, but starting with 512.4 mg (1.08 mmol) of methyl 3-[3-(3-fluoro-6-methoxyquinolin-4-yl)propyl]-1-[2-(2-thienylthio)ethyl] azetidine-3-carboxylate, 20 cm³ of dioxane and 10 cm³ of a 5 N aqueous sodium hydroxide solution, 1.5 hours under reflux. The medium is cooled and then 5 cm³ of hydrochloric acid are added, followed by an aqueous ammonia solution so as to reach a pH>8. The solvents are then evaporated under reduced pressure (2.7 kPa), without reaching dryness. The medium is taken up in 20 cm³ of water and allowed to stand, before filtering, washing with water and with diethyl ether. 473 mg of the sodium salt of 3-[3-(3-fluoro-6-methoxyquinolin-4-yl)propyl]-1-[2-(2-thienylthio)ethyl]-3-azetidinecarboxylic acid are thus obtained in the form of a white powder melting at around 67° C.

$^1$H NMR spectrum (300 MHz, (CD$_3$)$_2$SO d6, δ in ppm): 1.57 (mt: 2H); 1.96 (mt: 2H); 2.57 (broad t, J=7 Hz: 2H); 2.74 (broad t, J=7 Hz: 2H); from 2.95 to 3.10 (mt: 2H); 3.05 (broad d, J=7 Hz: 2H); 3.32 (broad d, J=7 Hz: 2H); 3.97 (s: 3H); 7.04 (dd, J=5.5 and 3.5 Hz: 1H); 7.17 (broad d, J=3.5 Hz: 1H); 7.38 (mt: 1H); 7.40 (dd, J=9 and 3 Hz: 1H); 7.60 (broad d, J=5.5 Hz: 1H); 7.97 (d, J=9 Hz: 1H); 8.70 (broad s: 1H).

EI mass spectrum: m/z 460 (M+), m/z 331 (base peak).

EXAMPLE 14

Methyl 3-[3-(3-fluoro-6-methoxyquinolin-4-yl)propyl]-1-[2-(2-thienylthio)ethyl]-3-azetidinecarboxylate A solution of 0.53 cm³ (2.7 mmol) of diisopropylcarbodiimide in 5 cm³ of tetrahydrofuran is added at a temperature in the region of 20° C. to a solution of 508 mg (1.35 mmol) of methyl 3-[3-(3-fluoro-6-methoxyquinolin-4-yl)propyl]-1-(2-hydroxyethyl)-3-azetidinecarboxylate, 314 mg (2.7 mmol) of 2-thiophenethiol and 708 mg (2.7 mmol) of triphenylphosphine in 5 cm³ of tetrahydrofuran and the medium is stirred for 22 hours at a temperature in the region of 20° C.

30 cm³ of diethyl ether are then added to the reaction medium, and the medium is extracted twice with 30 cm³ of water supplemented with 0.5 cm³ of concentrated methanesulfonic acid, and then with twice 30 cm³ of water. These acidic aqueous phases, after being combined, are washed with 30 cm³ of diethyl ether, and then alkalinized to pH>11; the medium is extracted 5 times with 50 cm³ of dichloromethane, before evaporating to dryness under reduced pressure (2.7 kPa). The residue (693 mg) is purified by flash chromatography on 150 cm³ of fine silica [eluent: cyclohexane/ethyl acetate (1/1 by volume)]. After concentrating the fractions under reduced pressure, 340 mg of methyl 3-[3-(3-fluoro-6-methoxyquinolin-4-yl)propyl]-1-[2-(2-thienylthio)ethyl]-3-azetidinecarboxylate are obtained in the form of an almost colorless oil.

$^1$H NMR spectrum (300 MHz, (CD$_3$)$_2$SO d6, δ in ppm): 1.53 (mt: 2H); 1.97 (mt: 2H); 2.56 (t, J=7 Hz: 2H); 2.74 (t, J=7 Hz: 2H); from 3.00 to 3.15 (mt: 2H); 3.06 (d, J=7 Hz: 2H); 3.33 (d, J=7 Hz: 2H); 3.59 (s: 3H); 3.97 (s: 3H); 7.04 (dd, J=5.5 and 3.5 Hz: 1H); 7.17 (dd, J=3.5 and 1 Hz: 1H); 7.37 (broad d, J=3 Hz: 1H); 7.41 (broad dd, J=9 and 3 Hz: 1H); 7.60 (dd, J=5.5 and 1 Hz: 1H); 7.97 (d, J=9 Hz: 1H); 8.70 (d, J=1 Hz: 1H).

EI mass spectrum: m/z 474 (M$^+$), m/z 345 (base peak).

Methyl 3-[3-(3-fluoro-6-methoxyquinolin-4-yl)propyl]-1-(2-hydroxyethyl)-3-azetidinecarboxylate may be prepared in the following manner:

3.51 g of potassium carbonate (24.4 mmol) are added to a solution of 2.57 g (6.347 mmol) of methyl 3-[3-(3-fluoro-6-methoxyquinolin-4-yl)propyl]-3-azetidine-carboxylate dihyhdrochloride and 0.75 cm³ (9.6 mmol) of 2-iodoethanol in 100 cm³ of acetonitrile, and the medium is stirred for 20 hours at a temperature in the region of 20° C., before heating for 1.25 hours under reflux and evaporating the solvents under reduced pressure. The residue is taken up in 100 cm³ of water and extracted with 3 times 100 cm³ of dichloromethane which is evaporated under reduced pressure (2.7 kPa). 2.88 g of a pink oil is obtained, which oil is purified by flash chromatography on 300 ml of fine silica [eluent: gradient of dichloromethane/methanol/aqueous ammonia solution at 28% (from 100-0-0 to 86-12-2 by volume)]. After concentrating the fractions under reduced pressure, 1.748 g of methyl 3-[3-(3-fluoro-6-methoxyquinolin-4-yl)propyl]-1-(2-hydroxyethyl)-3-azetidinecarboxylate are obtained in the form of a pink oil.

EI mass spectrum: m/z 376 (M$^+$), m/z 345 (base peak).

EXAMPLE 15

Sodium salt of (±)-3-[3-(3-chloro-6-methoxyquinolin-4-yl)propyl]-1-[(2E)-3-(2,5-difluorophenyl)-2-propenyl]-3-pyrrolidinecarboxylic acid By carrying out the procedure according to the method described in Example 1, but starting with 4-bromo-3-chloro-6-methoxyquinoline (which may be prepared according to the method described in patent WO200240474-A2), the sodium salt of (±)-3-[3-(3-chloro-6-methoxyquinolin-4-yl)propyl]-1-[(2E)-3-(2,5-difluorophenyl)-2-propenyl]-3-pyrrolidinecarboxylic acid is obtained in the form of a solid melting at 77° C.

EI mass spectrum: m/z=500 M$^+$; m/z=153 C$_9$H$_7$F$_2$$^+$ base peak.

Infrared spectrum KBr: 2936; 1621; 1504; 1491; 1230; 1117; 831; 743 and 728 cm$^{-1}$.

EXAMPLE 16

Sodium salt of (±)-1-[(2E)-3-(2,5-difluorophenyl)-2-propenyl]-3-[3-(6-methoxyquinolin-4-yl)propyl]-3-pyrrolidinecarboxylic acid By carrying out the procedure according to the method described in Example 1, but starting with 4-bromo-6-methoxyquinoline, the sodium salt of (±)-1-[(2E)-3-(2,5-difluorophenyl)-2-propenyl]-3-[3-(6-methoxyquinolin-4-yl)propyl]-3-pyrrolidinecarboxylic acid is obtained in the form of a solid melting at around 109–112° C.

CI mass spectrum m/z=467 MH$^+$ base peak.

Infrared spectrum KBr: 2941; 1621; 1591; 1509; 1490; 1242; 1228; 1031; 845 and 728 cm$^{-1}$.

EXAMPLE 17

Enantiomer A (levorotatory) of 3-[3-(3-fluoro-6-methoxyquinolin-4-yl)propyl]-1-[2-(2-thienylthio)ethyl]-3-pyrrolidinecarboxylic acid (undetermined absolute configuration)

By carrying out the procedure according to the method described in Example 3, but starting with methyl (±)-3-[3-(3-fluoro-6-methoxyquinolin-4-yl)propyl]-1-[2-(2-thienylthio)ethyl]-3-pyrrolidinecarboxylate, the enantiomer A (levorotatory) of 3-[3-(3-fluoro-6-methoxyquinolin-4-yl)propyl]-1-[2-(2-thienylthio)ethyl]-3-pyrrolidinecarboxylic acid (undetermined absolute configuration) is obtained in the form of a white solid melting at 160° C.

$[\alpha]_D^{20}$=−36.3+/−0.8 [dichloromethane (c=0.5), 589 nm].

IR spectrum (KBr) 2937; 1620; 1508; 1228; 1031; 847; 832; 809; 785; 708 and 452 cm$^{-1}$.

EI mass spectrum: m/z=474 (M+); 345 (M−C$_5$H$_5$S$_2$ )+ base peak.

Methyl (±)-3-[3-(3-fluoro-6-methoxyquinolin-4-yl)propyl]-1-[2-(2-thienylthio)ethyl]-3-pyrrolidinecarboxylate may be prepared as described in Example 2, but starting with 2-[(2-bromoethyl)thio]thiophene. A yellow oil is obtained.

EI mass spectrum: m/z 488 (M+).

2-[(2-Bromoethyl)thio]thiophene may be prepared according to the method described in patent WO200240474-A2.

EXAMPLE 18

Enantiomer B (dextrorotatory) of 3-[3-(3-fluoro-6-methoxyquinolin-4-yl)propyl]-1-[2-(2-thienylthio)ethyl]-3-pyrrolidinecarboxylic acid (undetermined absolute configuration)

By carrying out the procedure according to the method described in Example 3, but starting with methyl (±)-3-[3-(3-fluoro-6-methoxyquinolin-4-yl)propyl]-1-[2-(2-thienylthio)ethyl]-3-pyrrolidinecarboxylate, the enantiomer B (dextrorotatory) of 3-[3-(3-fluoro-6-methoxyquinolin-4-yl)propyl]-1-[2-(2-thienylthio)ethyl]-pyrrolidinecarboxylic acid (undetermined absolute configuration) is obtained in the form of a white solid melting at 172° C.

$[\alpha]_D^{20}$=+36.3+/−0.8 [dichloromethane (c=0.5), 589 nm].

IR spectrum (KBr) 2937; 1620; 1508; 1228; 1031; 847; 832; 809; 785; 708 and 452 cm$^{-1}$.

EI mass spectrum: m/z=474 (M+); 345 (M−C$_5$H$_5$S$_2$ )+ base peak.

EXAMPLE 19

Enantiomer A (dextrorotatory) of the sodium salt of 1-[2-[(2,5-difluorophenyl)thio]ethyl]-3-[3-(3-fluoro-6-methoxyquinolin-4-yl)propyl]-3-pyrrolidinecarboxylic acid (undetermined absolute configuration)

By carrying out the procedure according to the method described in Example 3, but starting with methyl (±)-1-[2-[(2,5-difluorophenyl)thio]ethyl]-3-[3-(3-fluoro-6-methoxyquinolin-4-yl)propyl]-3-pyrrolidinecarboxylate, the enantiomer A (dextrorotatory) of the sodium salt of 1-[2-[(2,5-difluorophenyl)thio]ethyl]-3-[3-(3-fluoro-6-methoxyquinolin-4-yl)propyl]-3-pyrrolidinecarboxylic acid (undetermined absolute configuration) is obtained in the form of a white solid.

[α]$_D^{20}$=+15.3+/−0.8 [dichloromethane (c=0.5), 589 nm].

IR spectrum (KBr) 2934; 1620; 1509; 1483; 1361; 1230; 1187; 1030; 909; 831 and 757 cm⁻.

CI mass spectrum m/z=505 (MH)+ base peak.

Methyl (±)-1-[2-[(2,5-difluorophenyl)thio]ethyl]-3-[3-(3-fluoro-6-methoxyquinolin-4-yl)propyl]-3-pyrrolidinecarboxylate may be prepared as described in Example 2, starting with 2-[(2-bromoethyl)thio]-1,4-difluorobenzene. A pale yellow oil is obtained.

EI mass spectrum: m/z 518 (M+).

2-[(2-Bromoethyl)thio]-1,4-difluorobenzene may be prepared according to the method described in patent W0200240474-A2.

EXAMPLE 20

Enantiomer B (levorotatory) of the sodium salt of 1-[2-[(2,5-difluorophenyl)thio]ethyl]-3-[3-(3-fluoro-6-methoxyquinolin-4-yl)propyl]-3-pyrrolidinecarboxylic acid (undetermined absolute configuration)

By carrying out the procedure according to the method described in Example 3, but starting with methyl (±)-1-[2-[(2,5-difluorophenyl)thio]ethyl]-3-[3-(3-fluoro-6-methoxyquinolin-4-yl)propyl]-3-pyrrolidinecarboxylate, the enantiomer B (levorotatory) of the sodium salt of 1-[2-[(2,5-difluorophenyl)thio]ethyl]-3-[3-(3-fluoro-6-methoxyquinolin-4-yl)propyl]-3-pyrrolidinecarboxylic acid (undetermined absolute configuration) is obtained in the form of a white solid.

[α]$_D^{20}$=−17.5+/−0.7 [dichloromethane (c =0.5), 589 nm].

IR spectrum (KBr) 2934; 1620; 1509; 1483; 1361; 1230; 1187; 1030; 909; 831 and 757 cm⁻.

CI mass spectrum m/z=505 (MH)+ base peak.

EXAMPLE 21

Enantiomer A (levorotatory) of 1-[2-(2,6-difluorophenoxy)ethyl]-3-[3-(3-fluoro-6-methoxyquinolin-4-yl)propyl]-3-pyrrolidinecarboxylic acid (undetermined absolute configuration)

By carrying out the procedure according to the method described in Example 3, but starting with methyl (±)-1-[2-(2,6-difluorophenoxy)ethyl]-3-[3-(3-fluoro-6-methoxyquinolin-4-yl)propyl]-3-pyrrolidinecarboxylate, the enantiomer A (levorotatory) of 1-[2-(2,6-difluorophenoxy)ethyl]-3-[3-(3-fluoro-6-methoxyquinolin-4-yl)propyl]-3-pyrrolidinecarboxylic acid (undetermined absolute configuration) is obtained in the form of a white lacquer.

[α]$_D^{20}$=−18.9+/−0.7 [methanol (c=0.5), 589 nm].

IR spectrum (CCl4) cm−12929; 1621; 1507; 1499; 1477; 1292; 1231; 1031; 1008; 908 and 832 cm⁻¹.

CI mass spectrum m/z=489 (MH)+ base peak.

Methyl (±)-1-[2-(2,6-difluorophenoxy)ethyl]-3-[3-(3-fluoro-6-methoxyquinolin-4-yl)propyl]-3-pyrrolidinecarboxylate may be prepared as described in Example 2, but starting with 2-(2-bromoethoxy)-1,3-difluorobenzene. A yellow oil is obtained.

EI mass spectrum: m/z 502 (M+).

2-(2-Bromoethoxy)-1,3-difluorobenzene may be described according to the method described in patent W0200240474-A2.

EXAMPLE 22

Enantiomer B (dextrorotatory) of 1-[2-(2,6-difluorophenoxy)ethyl]-3-[3-(3-fluoro-6-methoxyquinolin-4-yl)propyl]-3-pyrrolidinecarboxylic acid (undetermined absolute configuration)

By carrying out the procedure according to the method described in Example 3, but starting with methyl (±)-1-[2-(2,6-difluorophenoxy)ethyl]-3-[3-(3-fluoro-6-methoxyquinolin-4-yl)propyl]-3-pyrrolidinecarboxylate, the enantiomer B (dextrorotatory) of 1-[2-(2,6-difluorophenoxy)ethyl]-3-[3-(3-fluoro-6-methoxyquinolin-4-yl)propyl]-3-pyrrolidinecarboxylic acid (undetermined absolute configuration) is obtained in the form of a white lacquer.

[α]$_D^{20}$=+18.3+/−0.7 [methanol (c=0.5), 589 nm].

IR spectrum (CCl4) cm⁻¹ 2929; 1621; 1507; 1499; 1477; 1292; 1231; 1031; 1008; 908 and 832 cm⁻¹.

CI mass spectrum m/z=489 (MH)+ base peak.

EXAMPLE 23

Enantiomer A of 1-[3-(2,5-difluorophenyl)-2-propynyl]-3-[3-(3-fluoro-6-methoxyquinolin-4-yl)propyl]-3-pyrrolidinecarboxylic acid (undetermined absolute configuration)

8.3 cm³ of a 5 N aqueous sodium hydroxide solution is added at a temperature in the region of 20° C. to 0.49 g (0.987 mmol) of the enantiomer A of methyl 1-[3-(2,5-difluorophenyl)-2-propynyl]-3-[3-(3-fluoro-6-methoxyquinolin-4-yl)propyl]-3-pyrrolidinecarboxylate in solution in 30 cm³ of dioxane. After stirring under reflux for 16 hours, the reaction medium is concentrated under reduced pressure (2.7 kPa), and then taken up in 75 cm³ of distilled water. The clear yellow solution is then acidified to pH 5 with 20 cm³ of a 2 N aqueous hydrochloric acid solution, and then extracted with 75 cm³ of dichloromethane, and then twice 50 cm³ of dichloromethane. The organic phases are separated by decantation, dried over magnesium sulfate and then concentrated to dryness under reduced pressure (2.7 kPa) to give 0.29 g of a residue which is triturated in 5 cm³ of diisopropyl ether, and then dried. This operation is repeated twice. 0.28 g of the enantiomer A of 1-[3-(2,5-difluorophenyl)-2-propynyl]-3-[3-(3-fluoro-6-methoxyquinolin-4-yl)propyl]-3-pyrrolidinecarboxylic acid (undetermined absolute configuration) is obtained in the form of a cream-colored solid.

EI mass spectrum: m/z=482 M+.; m/z=151 $C_9H_5F_2$+ base peak.

Infrared spectrum KBr: 2943; 1621; 1509; 1496; 1231; 1170; 1031; 830; 767 and 595 cm⁻¹.

[α]$_D^{20}$=−37.5+/−1 [dichloromethane, (c=0.3), 589 nm].

The enantiomer A of methyl 1-[3-(2,5-difluorophenyl)-2-propynyl]-3-[3-(3-fluoro-6-methoxyquinolin-4-yl)propyl]-3-pyrrolidinecarboxylate may be prepared in the following manner:

A solution of 1.68 g of methyl (±)-1-(2-propynyl)-3-[3-(3-fluoro-6-methoxyquinolin-4-yl)propyl]-3-pyrrolidinecarboxylate (racemic), 75 mg of copper diiodide, 0.67 g of 2,5-difluorobromobenzene and 0.24 g of tetrakistriphenylphosphine in 17 cm³ of triethylamine is heated at 80° C. for one hour, and then stirred at room temperature for 16 hours. The reaction mixture is diluted with 100 cm³ of ethyl acetate and then filtered, the organic phase is washed three times with 50 cm³ of distilled water, and then extracted with 100 cm³ of a 2 N hydrochloric acid solution. The aqueous phase is brought to pH 8–9 by addition of potassium carbonate, and then extracted three times with 100 cm³ of ethyl acetate. The organic phases are combined, washed with 50 cm³ of distilled water, dried over magnesium sulfate and then concentrated to dryness under reduced pressure (2.7 kPa) to give 1.83 g of a thick brown oil, which oil is purified by flash chromatography [eluent: cyclohexane/ethyl acetate (1/1 by volume)]. After concentrating the fractions under reduced pressure, 1.46 g of a thick pale yellow oil are obtained.

The separation by chiral HPLC of the two enantiomers A and B of methyl 1-[3-(2,5-difluorophenyl)-2-propynyl]-3-[3-(3-fluoro-6-methoxyquinolin-4-yl)propyl]-3-pyrrolidinecarboxylate is carried out according to the method described in Examples 5 and 6.

For the enantiomer A [□]D20=−21.4+/−0.5 [methanol (c=0.5), 589 nm]; EI mass spectrum m/z=496 (M+).

For the enantiomer B [□]D20=+19.2+/−0.7 [methanol (c=0.5), 589 nm)]; EI mass spectrum ml/z=496 (M+).

Methyl (±)-1-(2-propynyl)-3-[3-(3-fluoro-6-methoxyquinolin-4-yl)propyl]-3-pyrrolidinecarboxylate (racemic) may be prepared in the following manner:

6.7 cm³ of triethylamine are added dropwise at room temperature to a solution of 6.23 g of methyl (±)-3-[3-(3-fluoro-6-methoxyquinolin-4-yl)propyl]-3-pyrrolidinecarboxylate dihydrochloride in 62 cm³ of dimethylformamide, followed dropwise by 2.4 cm³ of propargyl bromide. The solution is stirred at room temperature for 1 h, and then the reaction mixture is poured over 180 g of crushed ice and 350 cm³ of distilled water. The aqueous phase is extracted three times with 350 cm³ of ethyl ether, the organic phases are combined, washed with 350 cm³ of distilled water, dried over magnesium sulfate and then concentrated to dryness under reduced pressure (2.7 kPa) to give 3.2 g of an orange oil.

EI mass spectrum: m/z=384 (M+).

EXAMPLE 24

Enantiomer B of 1-[3-(2,5-difluorophenyl)-2-propynyl]-3-[3-(3-fluoro-6-methoxyquinolin-4-yl)propyl]-3-pyrrolidinecarboxylic acid (undetermined absolute configuration)

By carrying out the procedure according to the method described in Example 23, but starting with the enantiomer B of methyl 1-[3-(2,5-difluorophenyl)-2-propynyl]-3-[3-(3-fluoro-6-methoxyquinolin-4-yl)propyl]-3-pyrrolidinecarboxylate, the enantiomer B of 1-[3-(2,5-difluorophenyl)-2-propynyl]-3-[3-(3-fluoro-6-methoxyquinolin-4-yl)propyl]-3-pyrrolidinecarboxylic acid (undetermined absolute configuration) is obtained in the form of a solid.

EI mass spectrum: m/z=482 M+; m/z=151 $C_9H_5F_2$+ base peak.

Infrared spectrum KBr: 2943; 1621; 1509; 1496; 1231; 1170; 1031; 830; 767 and 595 cm$^{-1}$.

$[\alpha]_D^{20}$=+24.7+/0.7 [methanol, (c=0.3), 589 nm].

EXAMPLE 25

Enantiomer A of 3-[3-(3-chloro-6-methoxyquinolin-4-yl)propyl]-1-[(2E)-3-(2,5-difluorophenyl)-2-propenyl]-3-pyrrolidinecarboxylic acid (undetermined absolute configuration)

By carrying out the procedure according to the method described in Example 3, but with methyl (±)-3-[3-(3-chloro-6-methoxyquinolin-4-yl)propyl]-1-[(2E)-3-(2,5-difluorophenyl)-2-propenyl]-3-pyrrolidinecarboxylate, the enantiomer A of 3-[3-(3-chloro-6-methoxyquinolin-4-yl)propyl]-1-[(2E)-3-(2,5-difluorophenyl)-2-propenyl]-3-pyrrolidinecarboxylic acid is obtained in the form of a solid.

EI mass spectrum: m/z=500 M+.;m/z=153 $C_9H_7F_2$+ base peak.

Infrared spectrum KBr: 2965; 2936; 1621; 1591; 1504; 1491; 1423; 1230; 1117; 831; 743 and 728 cm$^{-1}$.

$[\alpha]_D^{20}$=−7.4+/−0.6 [dichloromethane, (c=0.5), 589 nm].

Methyl (±)-3-[3-(3-chloro-6-methoxyquinolin-4-yl)propyl]-1-[(2E)-3-(2,5-difluorophenyl)-2-propenyl]-3-pyrrolidinecarboxylate is prepared according to the method described in Example 1 but starting with 4-bromo-3-chloro-6-methoxyquinoline.

EI mass spectrum: m/z=515 (M+).

EXAMPLE 26

Enantiomer B of 3-[3-(3-chloro-6-methoxyquinolin-4-yl)propyl]-1-[(2E)-3-(2,5-difluorophenyl)-2-propenyl]-3-pyrrolidinecarboxylic acid (undetermined absolute configuration)

By carrying out the procedure according to the method described in Example 3, but starting with methyl (±)-3-[3-(3-chloro-6-methoxyquinolin-4-yl)propyl]-1-[(2E)-3-(2,5-difluorophenyl)-2-propenyl]-3-pyrrolidinecarboxylate, the enantiomer B of 3-[3-(3-chloro-6-methoxyquinolin-4-yl)propyl]-1-[(2E)-3-(2,5-difluorophenyl)-2-propenyl]-3-pyrrolidinecarboxylic acid is obtained in the form of a solid.

EI mass spectrum: m/z=500 M+; m/z=153 $C_9H_7F_2$+ base peak.

Infrared spectrum KBr: 2965; 2936; 1621; 1591; 1504; 1491; 1423; 1230; 1117; 831; 743 and 728 cm$^{-1}$.

$[\alpha]_D^{20}$=+5.5+/−0.5 [dichloromethane, (c=0.5), 589 nm]

EXAMPLE 27

Enantiomer A of 1-[3-(2,6-difluorophenyl)-2-propynyl]-3-[3-(3-fluoro-6-methoxyquinolin-4-yl)propyl]-3-pyrrolidinecarboxylic acid (undetermined absolute configuration)

By carrying out the procedure according to the method described in Example 23, but starting with 2,6-difluorobromobenzene, the enantiomer A of 1-[3-(2,6-difluorophenyl)-2-propynyl]-3-[3-(3-fluoro-6-methoxyquinolin-4-yl)propyl]-3-pyrrolidinecarboxylic acid (undetermined absolute configuration) is obtained in the form of a solid.

EI mass spectrum: m/z=482 M+; m/z=151 $C_9H_5F_2$+ base peak.

Infrared spectrum KBr: 2941; 1707; 1622; 1509; 1469; 1231; 1145; 1030; 1004; 830; 785 and 719 cm$^{-1}$.

$[\alpha]_D^{20}$=−31+/−0.7 [methanol, (c=0.5), 589 nm].

EXAMPLE 28

Enantiomer B of 1-[3-(2,6-difluorophenyl)-2-propynyl]-3-[3-(3-fluoro-6-methoxyquinolin-4-yl)propyl]-3-pyrrolidinecarboxylic acid (undetermined absolute configuration)

By carrying out the procedure according to the method described in Example 23, but starting with 2,6-difluorobromobenzene, the enantiomer B of 1-[3-(2,6-difluorophenyl)-2-propynyl]-3-[3-(3-fluoro-6-methoxyquinolin-4-yl)propyl]-3-pyrrolidinecarboxylic acid (undetermined absolute configuration) is obtained in the form of a solid.

EI mass spectrum: m/z=482 M+; m/z=151 $C_9H_5F_2$+ base peak.

Infrared spectrum KBr: 2941; 1707; 1622; 1509; 1469; 1231; 1145; 1030; 1004; 830; 785 and 719 $cm^{-1}$.

$[\alpha]_D^{20}$=+31.7+/−0.9 [methanol, (c=0.5), 589 nm].

EXAMPLE 29

Enantiomer A (levorotatory) of 1-[2-(2,5-difluorophenoxy)ethyl]-3-[3-(3-fluoro-6-methoxyquinolin-4-yl)propyl]-3-pyrrolidinecarboxylic acid (undetermined absolute configuration)

By carrying out the procedure according to the method described in Example 3, but starting with methyl (±)-1-[2-(2,5-difluorophenoxy)ethyl]-3-[3-(3-fluoro-6-methoxyquinolin-4-yl)propyl]-3-pyrrolidinecarboxylate, the enantiomer A (levorotatory) of 1-[2-(2,5-difluorophenoxy)ethyl]-3-[3-(3-fluoro-6-methoxyquinolin-4-yl)propyl]-3-pyrrolidinecarboxylic acid (undetermined absolute configuration) is obtained in the form of a white foam.

$[\alpha]_D^{20}$=−17.5+/−0.7 [methanol (c=0.5), 589 nm].

IR spectrum (KBr) cm−1 2930; 1709; 1622; 1514; 1231; 1205; 1159; 1029; 832 and 793 $cm^{-1}$.

CI mass spectrum m/z=489 (MH)+ base peak.

Methyl (±)-1-[2-(2,5-difluorophenoxy)ethyl]-3-[3-(3-fluoro-6-methoxyquinolin-4-yl)propyl]-3-pyrrolidinecarboxylate may be prepared as described in Example 2, but starting with 2-(2-bromoethoxy)-1,4-difluorobenzene. A yellow oil is obtained.

EI mass spectrum: m/z 502 (M+).

2-(2-Bromoethoxy)-1,4-difluorobenzene may be prepared according to the method described in patent WO200240474-A2.

EXAMPLE 30

Enantiomer B (dextrorotatory) of 1-[2-(2,5-difluorophenoxy)ethyl]-3-[3-(3-fluoro-6-methoxyquinolin-4-yl)propyl]-3-pyrrolidinecarboxylic acid (undetermined absolute configuration)

By carrying out the procedure according to the method described in Example 3, but starting with methyl (±)-1-[2-(2,5-difluorophenoxy)ethyl]-3-[3-(3-fluoro-6-methoxyquinolin-4-yl)propyl]-3-pyrrolidinecarboxylate, the enantiomer B (dextrorotatory) of 1-[2-(2,5-difluorophenoxy)ethyl]-3-[3-(3-fluoro-6-methoxyquinolin-4-yl)propyl]-3-pyrrolidinecarboxylic acid (undetermined absolute configuration) is obtained in the form of a white solid melting at 157° C.

$[\alpha]_D^{20}$=+22.6+/−0.7 [methanol (c=0.5), 589 nm].

IR spectrum (KBr) $cm^{-1}$ 2930; 1709; 1622; 1514; 1231; 1205; 1159; 1029; 832 and 793 $cm^{-1}$.

EI mass spectrum: m/z=488 (M+); 345 (M−$C_7H_5OF_2$)+ base peak.

EXAMPLE 31

Enantiomer A (dextrorotatory) of the sodium salt of 3-[3-(3-chloro-6-methoxyquinolin-4-yl)propyl]-1-[2-(2-thienylthio)ethyl]-3-pyrrolidinecarboxylic acid (undetermined absolute configuration)

By carrying out the procedure according to the method described in Example 3, but starting with methyl (±)-3-[3-(3-chloro-6-methoxyquinolin-4-yl)propyl]-1-[2-(2-thienylthio)ethyl]-3-pyrrolidinecarboxylate, the enantiomer A (dextrorotatory) of the sodium salt of 3-[3-(3-chloro-6-methoxyquinolin-4-yl)propyl]-1-[2-(2-thienylthio)ethyl]-3-pyrrolidinecarboxylic acid (undetermined absolute configuration) is obtained in the form of a white solid melting between 265° C. and 270° C.

$[\alpha]_D^{20}$=+7.1+/−0.6 [methanol (c=0.5), 589 nm].

IR spectrum (KBr) $cm^{-1}$ 2952; 2815; 1621; 1558; 1506; 1412; 1229; 1125; 1028; 828; 744 and 705 $cm^{-1}$.

ES mass spectrum: m/z=491 (MH)+ base peak.

Methyl (±)-3-[3-(3-chloro-6-methoxyquinolin-4-yl)propyl]-1-[2-(2-thienylthio)ethyl]-3-pyrrolidinecarboxylate may be prepared as described in Example 2, but starting with 3-chloro-4-bromo-6-methoxyquinoline and 2-[(2-bromoethyl)thio]thiophene. A colorless oil is obtained.

EI mass spectrum: m/z 504 (M+).

3-Chloro-4-bromo-6-methoxyquinoline may be prepared as described in patent WO200240474-A2.

EXAMPLE 32

Enantiomer B (levorotatory) of the sodium salt of 3-[3-(3-chloro-6-methoxyquinolin-4-yl)propyl]-1-[2-(2-thienylthio)ethyl]-3-pyrrolidinecarboxylic acid (undetermined absolute configuration)

By carrying out the procedure according to the method described in Example 3, but starting with methyl (±)-3-[3-(3-chloro-6-methoxyquinolin-4-yl)propyl]-1-[2-(2-thienylthio)ethyl]-3-pyrrolidinecarboxylate, the enantiomer B (levorotatory) of the sodium salt of 3-[3-(3-chloro-6-methoxyquinolin-4-yl)propyl]-1-[2-(2-thienylthio)ethyl]-3-pyrrolidinecarboxylic acid (undetermined absolute configuration) is obtained in the form of a white solid melting between 269° C. and 271° C.

$[\alpha]_D^{20}$=−3.3+/−0.5 [methanol (c=0.5), 589 nm].

IR spectrum (KBr) $cm^{-1}$ 2952; 2815; 1621; 1558; 1506; 1412; 1229; 1125; 1028; 828; 744 and 705 $cm^{-1}$.

ES mass spectrum: m/z=491 (MH)+ base peak.

EXAMPLE 33

Enantiomer A (dextrorotatory) of 3-[3-(3-chloro-6-methoxyquinolin-4-yl)propyl]-1-[2-[(2,5-difluorophenyl)thio]ethyl]-3-pyrrolidinecarboxylic acid (undetermined absolute configuration)

By carrying out the procedure according to the method described in Example 3, but starting with methyl (±)-3-[3-(3-chloro-6-methoxyquinolin-4-yl)propyl]-1-[2-[(2,5-difluorophenyl)thio]ethyl]-3-pyrrolidinecarboxylate, the enantiomer A (dextrorotatory) of 3-[3-(3-chloro-6-methoxyquinolin-4-yl)propyl]-1-[2-[(2,5-difluorophenyl)

thio]ethyl]-3-pyrrolidinecarboxylic acid (undetermined absolute configuration) is obtained in the form of a white solid melting at 146° C.

$[\alpha]_D^{20}$=+25.8+/−0.8 [methanol (c=0.5), 589 nm].

IR spectrum (CH$_2$C$_{12}$) cm$^{-1}$ 2940; 1732; 1622; 1504; 1484; 1230; 1188; 1119 and 834 cm$^{-1}$.

CI mass spectrum m/z=521 (MH)+ base peak.

Methyl (±)-3-[3-(3-chloro-6-methoxyquinolin-4-yl)propyl]-1-[2-[(2,5-difluorophenyl)thio]ethyl]-3-pyrrolidinecarboxylate may be prepared as described in Example 2, but starting with 3-chloro-4-bromo-6-methoxyquinoline and 2-[(2-bromoethyl)thio]-1,4-difluoro-benzene. An ochre oil is obtained.

EI mass spectrum: m/z 534 (M+).

EXAMPLE 34

Enantiomer B (levorotatory) of 3-[3-(3-chloro-6-methoxyquinolin-4-yl)propyl]-1-[2-[(2,5-difluorophenyl)thio]ethyl]-3-pyrrolidinecarboxylic acid (undetermined absolute configuration)

By carrying out the procedure according to the method described in Example 3, but starting with methyl (±)-3-[3-(3-chloro-6-methoxyquinolin-4-yl)propyl]-1-[2-[(2,5-difluorophenyl)thio]ethyl]-3-pyrrolidinecarboxylate, the enantiomer B (levorotatory) of 3-[3-(3-chloro-6-methoxyquinolin-4-yl)propyl]-1-[2-[(2,5-difluorophenyl)thio]ethyl]-3-pyrrolidinecarboxylic acid (undetermined absolute configuration) is obtained in the form of a white solid melting at 146° C.

$[\alpha]_D^{20}$=−20.4+/−0.8 [methanol (c=0.5), 589 nm].

IR spectrum (KBr) cm$^{-1}$ 2953; 1707; 1620; 1504; 1483; 1231; 1188; 1118; 829 and 744 cm$^{-1}$.

CI mass spectrum m/z=521 (MH)+ base peak.

EXAMPLE 35

Enantiomer A of 1-[(2E)-3-(2,5-dichlorophenyl)-2-propenyl]-3-[3-(3-fluoro-6-methoxyquinolin-4-yl) propyl]-3-pyrrolidinecarboxylic acid (undetermined absolute configuration)

By carrying out the procedure according to the method described in Example 3, but starting with 2-((2E)-3-chloro-2-propenyl)-1,4-dichlorobenzene, the enantiomer A of 1-[(2E)-3-(2,5-dichlorophenyl)-2-propenyl]-3-[3-(3-fluoro-6-methoxyquinolin-4-yl)propyl]-3-pyrrolidinecarboxylic acid (undetermined absolute configuration) is obtained in the form of a solid.

EI mass spectrum: m/z=516 M+.; m/z=481 (M−Cl)+ base peak.

Infrared spectrum KBr: 2938; 1709; 1621; 1508; 1464; 1360; 1230; 1097; 1030; 969; 830; 811 and 785 cm$^{-1}$ $[\alpha]_D^{20}$=−21.2+/−0.6 [methanol, (c=0.5), 589 nm].

EXAMPLE 36

Enantiomer B of 1-[(2E)-3-(2,5-dichlorophenyl)-2-propenyl]-3-[3-(3-fluoro-6-methoxyquinolin-4-yl) propyl]-3-pyrrolidinecarboxylic acid (undetermined absolute configuration)

By carrying out the procedure according to the method described in Example 3, but starting with 2-((2E)-3-chloro-2-propenyl)-1,4-dichlorobenzene, the enantiomer B of 1-[(2E)-3-(2,5-dichlorophenyl)-2-propenyl]-3-[3-(3-fluoro-6-methoxyquinolin-4-yl)propyl]-3-pyrrolidinecarboxylic acid (undetermined absolute configuration) is obtained in the form of a solid melting at 102° C.

EI mass spectrum: m/z=516 M+.; m/z=481 (M−Cl)+ base peak.

Infrared spectrum KBr: 2938; 1709; 1621; 1508; 1464; 1360; 1230; 1097; 1030; 969; 830; 811 and 785 cm$^{-1}$.

$[\alpha]_D^{20}$=+22 [methanol, (c=0.5), 589 nm].

EXAMPLE 37

Enantiomer A of the sodium salt of 1-[(2E)-3-(3,5-difluorophenyl)-2-propenyl]-3-[3-(3-fluoro-6-methoxyquinolin-4-yl)propyl]-3-pyrrolidinecarboxylic acid (undetermined absolute configuration)

By carrying out the procedure according to the method described in Example 3, but starting with 2-((2E)-3-chloro-2-propenyl)-3,5-difluorobenzene, the sodium salt of the enantiomer A of the sodium salt of 1-[(2E)-3-(3,5-difluorophenyl)-2-propenyl]-3-[3-(3-fluoro-6-methoxyquinolin-4-yl)propyl]-3-pyrrolidinecarboxylic acid (undetermined absolute configuration) is obtained in the form of a solid.

EI mass spectrum: m/z=484 M+.; m/z=153 C$_9$H$_7$F$_2$+ base peak.

Infrared spectrum KBr: 2928; 1706; 1621; 1591; 1509; 1469; 1322; 1231; 1119; 1030; 984 and 831 cm$^{-1}$.

$[\alpha]_D^{20}$=−25.6+/−0.8 [methanol, (c=0,5), 589 nm]

EXAMPLE 38

Enantiomer B of 1-[(2E)-3-(3,5-difluorophenyl)-2-propenyl]-3-[3-(3-fluoro-6-methoxyquinolin-4-yl) propyl]-3-pyrrolidinecarboxylic acid (undetermined absolute configuration)

By carrying out the procedure according to the method described in Example 3, but starting with 2-((2E)-3-chloro-2-propenyl)-3,5-difluorobenzene, the enantiomer B of 1-[(2E)-3-(3,5-difluorophenyl)-2-propenyl]-3-[3-(3-fluoro-6-methoxyquinolin-4-yl)propyl]-3-pyrrolidinecarboxylic acid (undetermined absolute configuration) is obtained in the form of a solid.

EI mass spectrum: m/z=484 M+.; m/z=153 C$_9$H$_7$F$_2$+ base peak.

Infrared spectrum KBr: 2928; 1706; 1621; 1591; 1509; 1469; 1322; 1231; 1119; 1030; 984 and 831 cm$^{-1}$.

$[\alpha]_D^{20}$=+28.2+/−0.8 [methanol, (c=0.5), 589 nm].

EXAMPLE 39

Enantiomer A of 1-[3-(5-chloro-2-fluoro-phenyl)-2-propynyl]-3-[3-(3-fluoro-6-methoxyquinolin-4-yl) propyl]-3-pyrrolidinecarboxylic acid (undetermined absolute configuration)

By carrying out the procedure according to the method described in Example 23, but starting with 2-fluoro-5-chloro-bromobenzene, the enantiomer A of 1-[3-(5-chloro-2-fluoro-phenyl)-2-propynyl]-3-[3-(3-fluoro-6-methoxyquinolin-4-yl)propyl]-3-pyrrolidinecarboxylic acid (undetermined absolute configuration) is obtained in the form of a solid.

CI mass spectrum m/z=499 MH+ base peak.

Infrared spectrum CCl$_4$: 2936; 1704; 1622; 1508; 1487; 1469; 1259; 1232; 1218 and 832 cm$^{-1}$.

$[\alpha]_D^{20}$=−27.3+/−0.9 [methanol, (c=0.5), 589 nm].

EXAMPLE 40

Enantiomer B of 1-[3-(5-chloro-2-fluoro-phenyl)-2-propynyl]-3-[3-(3-fluoro-6-methoxyquinolin-4-yl)propyl]-3-pyrrolidinecarboxylic acid (undetermined absolute configuration)

By carrying out the procedure according to the method described in Example 23, but starting with 2-fluoro-5-chloro-bromobenzene, the enantiomer B of 1-[3-(5-chloro-2-fluoro-phenyl)-2-propynyl]-3-[3-(3-fluoro-6-methoxyquinolin-4-yl)propyl]-3-pyrrolidinecarboxylic acid (undetermined absolute configuration) is obtained in the form of a solid.

CI mass spectrum m/z=499 MH+ base peak.
Infrared spectrum KBr: 2942; 1707; 1621; 1509; 1486; 1469; 1260; 1231; 1145; 1085; 1030 and 830 cm$^{-1}$.
$[\alpha]_D^{20}$=+29.6+/−1 [methanol, (c=0.5), 589 nm].

EXAMPLE 41

Enantiomer A of the hydrochloride of 3-[3-(3-fluoro-6-methoxyquinolin-4-yl)propyl]-1-[(2E)-3-(2,6-difluorophenyl)-2-propenyl]-3-pyrrolidinecarboxylic acid (undetermined absolute configuration)

By carrying out the procedure according to the method described in Example 3, but starting with 2-((2E)-3-chloro-2-propenyl)-2,6-difluorobenzene the enantiomer A of the hydrochloride of 3-[3-(3-fluoro-6-methoxyquinolin-4-yl)propyl]-1-[(2E)-3-(2,6-difluorophenyl)-2-propenyl]-3-pyrrolidinecarboxylic acid (undetermined absolute configuration) is obtained in the form of a solid melting at 96° C.

EI mass spectrum: m/z=484 M+.; m/z=153 C$_9$H$_7$F$_2$+ base peak.
Infrared spectrum KBr: 2942; 2459; 1715; 1621; 1509; 1468; 1361; 1266; 1232; 990; 830 and 782 cm$^{-1}$.
$[\alpha]_D^{20}$=−22.3+/−0.8 [methanol, (c=0.5), 589 nm].

EXAMPLE 42

Enantiomer B of 3-[3-(3-fluoro-6-methoxyquinolin-4-yl)propyl]-1-[(2E)-3-(2,6-difluorophenyl)-2-propenyl]-3-pyrrolidinecarboxylic acid (undetermined absolute configuration)

By carrying out the procedure according to the method described in Example 3, but starting with 2-((2E)-3-chloro-2-propenyl)-2,6-difluorobenzene, the enantiomer B of 3-[3-(3-fluoro-6-methoxyquinolin-4-yl)propyl]-1-[(2E)-3-(2,6-difluorophenyl)-2-propenyl]-3-pyrrolidinecarboxylic acid (undetermined absolute configuration) is obtained in the form of a solid melting at 88° C.

CI mass spectrum m/z=485 MH+ base peak.
Infrared spectrum KBr: 2941; 1710; 1621; 1508; 1467; 1360; 1266; 1231; 1144; 989; 830 and 782 cm$^{-1}$.
$[\alpha]_D^{20}$=+23.7+/−0.7 [methanol, (c=0.5), 589 nm].

EXAMPLE 43

Enantiomer A of 3-[3-(3-fluoro-6-methoxyquinolin-4-yl)propyl]-1-[3-(3,4,5-trifluorophenyl)-2-propynyl]-3-pyrrolidinecarboxylic acid (undetermined absolute configuration)

By carrying out the procedure according to the method described in Example 23, but starting with 3,4,5-trifluoro-bromobenzene, the enantiomer A of 3-[3-(3-fluoro-6-methoxyquinolin-4-yl)propyl]-1-[3-(3,4,5-trifluorophenyl)-2-propynyl]-3-pyrrolidinecarboxylic acid (undetermined absolute configuration) is obtained in the form of a solid.

EI mass spectrum: m/z=500 M+.; m/z=169 C$_9$H$_4$F$_3$+ base peak.
Infrared spectrum KBr: 2944; 1709; 1621; 1612; 1528; 1429; 1232; 1048; 858 and 830 cm$^{-1}$.
$[\alpha]_D^{20}$=−17.5+/−0.5 [methanol, (c=0.5), 589 nm].

EXAMPLE 44

Enantiomer B of 3-[3-(3-fluoro-6-methoxyquinolin-4-yl)propyl]-1-[3-(3,4,5-trifluorophenyl)-2-propynyl]-3-pyrrolidinecarboxylic acid (undetermined absolute configuration)

By carrying out the procedure according to the method described in Example 23, but starting with 3,4,5-trifluoro-bromobenzene, the enantiomer B of 3-[3-(3-fluoro-6-methoxyquinolin-4-yl)propyl]-1-[3-(3,4,5-trifluorophenyl)-2-propynyl]-3-pyrrolidinecarboxylic acid (undetermined absolute configuration) is obtained in the form of a solid.

EI mass spectrum: m/z=500 M+.; m/z=169 C$_9$H$_4$F$_3$+ base peak.
Infrared spectrum KBr: 2944; 1709; 1621; 1612; 1528; 1429; 1232; 1048; 858 and 830 cm$^{-1}$.
$[\alpha]_D^{20}$=+16.8+/−0.6 [methanol, (c=0.5), 589 nm].

EXAMPLE 45

Enantiomer A of 1-[(2E)-3-(5-chloro-2-fluoro-phenyl)-2-propenyl]-3-[3-(3-fluoro-6-methoxyquinolin-4-yl)propyl]-3-pyrrolidinecarboxylic acid (undetermined absolute configuration)

By carrying out the procedure according to the method described in Example 3, but starting with 2-((2E)-3-chloro-2-propenyl)-2-fluoro-5-chlorobenzene, the enantiomer A of 1-[(2E)-3-(5-chloro-2-fluoro-phenyl)-2-propenyl]-3-[3-(3-fluoro-6-methoxyquinolin-4-yl)propyl]-3-pyrrolidinecarboxylic acid (undetermined absolute configuration) is obtained in the form of a solid.

CI mass spectrum: m/z=501 MH+ base peak.
Infrared spectrum KBrCCl$_4$: 2936; 1707; 1621; 1508; 1482; 1231; 1033; 972; 832 and 649 cm$^{-1}$.
$[\alpha]_D^{20}$=−17.4+/−0.6 [methanol, (c=0.5), 589 nm].

EXAMPLE 46

Enantiomer B of 1-[(2E)3-(5-chloro-2-fluoro-phenyl)-2-propenyl]-3-[3-(3-fluoro-6-methoxyquinolin-4-yl)propyl]-3-pyrrolidinecarboxylic acid (undetermined absolute configuration)

By carrying out the procedure according to the method described in Example 3, but starting with 2-((2E)-3-chloro-2-propenyl)-2-fluoro-5-chloro-benzene, the enantiomer B of 1-[(2E)3-(5-chloro-2-fluoro-phenyl)-2-propenyl]-3-[3-(3-fluoro-6-methoxyquinolin-4-yl)propyl]-3-pyrrolidinecarboxylic acid (undetermined absolute configuration) is obtained in the form of a solid.

EI mass spectrum: m/z=500 M+.; m/z=169 C$_9$H$_7$ClF+ base peak.
Infrared spectrum CCl$_4$: 2936; 1707; 1621; 1508; 1482; 1231; 1033; 972; 832 and 649 cm$^{-1}$.
$[\alpha]_D^{20}$=+18.3+/−0.6 [methanol, (c=0.5), 589 nm].

EXAMPLE 47

Enantiomer A of 1-[(2E)3-(2,3-difluoro-phenyl)-2-propenyl]-3-[3-(3-fluoro-6-methoxyquinolin-4-yl)propyl]-3-pyrrolidinecarboxylic acid (undetermined absolute configuration)

By carrying out the procedure according to the method described in Example 3, but starting with 2-((2E)-3-chloro-2-propenyl)-2,3-difluorobenzene, the enantiomer A of 1-[(2E)3-(2,3-difluoro-phenyl)-2-propenyl]-3-[3-(3-fluoro-6-methoxyquinolin-4-yl)propyl]-3-pyrrolidinecarboxylic acid (undetermined absolute configuration) is obtained in the form of a solid.

CI mass spectrum: m/z=485 MH+ base peak.

Infrared spectrum $CCl_4$: 2936; 1706; 1622; 1508; 1484; 1264; 1231; 1032; 973; 832 and 713 $cm^{-1}$.

$[\alpha]_D^{20}$=−21.1+/−0.6 [methanol, (c=0.5), 589 nm].

EXAMPLE 48

Enantiomer B of 1-[(2E)3-(2,3-difluoro-phenyl)-2-propenyl]-3-[3-(3-fluoro-6-methoxyquinolin-4-yl)propyl]-3-pyrrolidinecarboxylic acid (undetermined absolute configuration)

By carrying out the procedure according to the method described in Example 3, but starting with 2-((2E)-3-chloro-2-propenyl)-2,3-difluorobenzene, the enantiomer B of 1-[(2E)3-(2,3-difluoro-phenyl)-2-propenyl]-3-[3-(3-fluoro-6-methoxyquinolin-4-yl)propyl]-3-pyrrolidinecarboxylic acid (undetermined absolute configuration) is obtained in the form of a solid.

EI mass spectrum: m/z=484 M+. base peak; m/z=153 $C_9H_7F_2$+

Infrared spectrum $CCl_4$: 2936; 1706; 1622; 1508; 1484; 1264; 1231; 1032; 973; 832 and 713 $cm^{31\ 1}$.

$[\alpha]_D^{20}$=+21.5+/−0.7 [methanol, (c=0.5), 589 nm].

EXAMPLE 49

Enantiomer A of 3-[3-(3-fluoro-6-methoxyquinolin-4-yl)propyl]-1-[(2E)-3-(3,4,5-trifluorophenyl)-2-propenyl]-3-pyrrolidinecarboxylic acid (undetermined absolute configuration)

By carrying out the procedure according to the method described in Example 3, but starting with 2-((2E)-3-chloro-2-propenyl)-3,4,5-trifluorobenzene, the enantiomer A of 3-[3-(3-fluoro-6-methoxyquinolin-4-yl)propyl]-1-[(2E)-3-(3,4,5-trifluorophenyl)-2-propenyl]-3-pyrrolidinecarboxylic acid (undetermined absolute configuration) is obtained in the form of a solid melting at 110° C.

EI mass spectrum: m/z=502 M+.; m/z=171 $C_9H_6F_3$+ base peak.

Infrared spectrum KBr: 2940; 1620; 1529; 1509; 1442; 1359; 1232; 1042; 970; 831 and 790 $cm^{-1}$.

$[\alpha]_D^{20}$=+28.1+/−0.8 [methanol, (c=0.5), 589 nm].

EXAMPLE 50

Enantiomer B of 3-[3-(3-fluoro-6-methoxyquinolin-4-yl)propyl]-1-[(2E)-3-(3,4,5-trifluorophenyl)-2-propenyl]-3-pyrrolidinecarboxylic acid (undetermined absolute configuration)

By carrying out the procedure according to the method described in Example 3, but starting with 2-((2E)-3-chloro-2-propenyl)-3,4,5-trifluorobenzene, the enantiomer B of 3-[3-(3-fluoro-6-methoxyquinolin-4-yl)propyl]-1-[(2E)-3-(3,4,5-trifluorophenyl)-2-propenyl]-3-pyrrolidinecarboxylic acid (undetermined absolute configuration) is obtained in the form of a solid melting at 148° C.

EI mass spectrum: m/z=502 M+.; m/z=171 $C_9H_6F_3$+ base peak.

Infrared spectrum KBr: 2940; 1620; 1529; 1509; 1442; 1359; 1232; 1042; 970; 831 and 790 $cm^{-1}$.

$[\alpha]_D^{20}$=−19.4+/−0.6 [methanol, (c=0.5), 589 nm].

EXAMPLE 51

Enantiomer A of 1-[3-(2,3-difluorophenyl)-2-propynyl]-3-[3-(3-fluoro-6-methoxyquinolin-4-yl)propyl]-3-pyrrolidinecarboxylic acid (undetermined absolute configuration)

By carrying out the procedure according to the method described in Example 23, but starting with 2,3-difluorobromobenzene, the enantiomer A of 1-[3-(2,3-difluorophenyl)-2-propynyl]-3-[3-(3-fluoro-6-methoxyquinolin-4-yl)propyl]-3-pyrrolidinecarboxylic acid (undetermined absolute configuration) is obtained in the form of a solid.

CI mass spectrum: m/z=483 MH+ base peak.

Infrared spectrum KBr: 2941; 1706; 1621; 1584; 1509; 1489; 1473; 1231; 1146; 1030; 831; 784 and 716 $cm^{-1}$.

$[\alpha]_D^{20}$=−25.1+/−0.8 [methanol, (c=0.5), 589 nm].

EXAMPLE 52

Enantiomer B of 1-[3-(2,3-difluorophenyl)-2-propynyl]-3-[3-(3-fluoro-6-methoxyquinolin-4-yl)propyl]-3-pyrrolidinecarboxylic acid (undetermined absolute configuration)

By carrying out the procedure according to the method described in Example 23, but starting with 2,3-difluorobromobenzene, the enantiomer B of 1-[3-(2,3-difluorophenyl)-2-propynyl]-3-[3-(3-fluoro-6-methoxyquinolin-4-yl)propyl]-3-pyrrolidinecarboxylic acid (undetermined absolute configuration) is obtained in the form of a solid.

EI mass spectrum: m/z=482 M+.; m/z=151 $C_9H_5F_2$+ base peak.

Infrared spectrum KBr: 2941; 1706; 1621; 1584; 1509; 1489; 1473; 1231; 1146; 1030; 831; 784 and 716 $cm^{-1}$.

$[\alpha]_D^{20}$=+27.2+/−0.9 [methanol, (c=0.5), 589 nm].

EXAMPLE 53

Enantiomer A of 1-[3-(3,5-difluorophenyl)-2-propynyl]-3-[3-(3-fluoro-6-methoxyquinolin-4-yl)propyl]-3-pyrrolidinecarboxylic acid (undetermined absolute configuration)

By carrying out the procedure according to the method described in Example 23, but starting with 3,5-difluorobromobenzene, the enantiomer A of 1-[3-(3,5-difluorophenyl)-

2-propynyl]-3-[3-(3-fluoro-6-methoxyquinolin-4-yl)propyl]-3-pyrrolidinecarboxylic acid (undetermined absolute configuration) is obtained in the form of a solid.

EI mass spectrum: m/z=482 M+.; m/z=151 $C_9H_5F_2$+ base peak.

Infrared spectrum KBr: 2937; 1708; 1619; 1586; 1509; 1470; 1430; 1231; 1122; 1030; 990; 857; 831 and 672 cm$^{-1}$.

$[\alpha]_D^{20}$=−19.4+/−0.7 [methanol, (c=0.5), 589 mn].

EXAMPLE 54

Enantiomer B of 1-[3-(3,5-difluorophenyl)-2-propynyl]-3-[3-(3-fluoro-6-methoxyquinolin-4-yl)propyl]-3-pyrrolidinecarboxylic acid (undetermined absolute configuration)

By carrying out the procedure according to the method described in Example 23, but starting with 3,5-difluorobromobenzene, the enantiomer B of 1-[3-(3,5-difluorophenyl)-2-propynyl]-3-[3-(3-fluoro-6-methoxyquinolin-4-yl)propyl]-3-pyrrolidinecarboxylic acid (undetermined absolute configuration) is obtained in the form of a solid.

EI mass spectrum: m/z=482 M+.; m/z=151 $C_9H_5F_2$+ base peak.

Infrared spectrum KBr: 2937; 1708; 1619; 1586; 1509; 1470; 1430; 1231; 1122; 1030; 990; 857; 831 and 672 cm$^{-1}$.

$[\alpha]_D^{20}$=+27.7+/−1 [methanol, (c=0.5), 589 nm].

EXAMPLE 55

Enantiomer A of 1-[3-(2,5-difluorophenyl)-2-propynyl]-3-[3-(3-fluoro-6-methoxyquinolin-4-yl)propyl]-3-pyrrolidinecarboxylic acid (undetermined absolute configuration)

By carrying out the procedure according to the method described in Example 23, but starting with 2,5-dichlorobromobenzene, the enantiomer A of 1-[3-(2,5-difluorophenyl)-2-propynyl]-3-[3-(3-fluoro-6-methoxyquinolin-4-yl)propyl]-3-pyrrolidinecarboxylic acid (undetermined absolute configuration) is obtained in the form of a solid.

CI mass spectrum: m/z=515 MH+ base peak.

Infrared spectrum KBr: 2928; 1709; 1621; 1509; 1468; 1231; 1096; 1031; 830; 786 and 600 cm$^{-1}$.

$[\alpha]_D^{20}$=−22.5+/−0.9 [methanol, (c=0.5), 589 nm].

EXAMPLE 56

Enantiomer B of 1-[3-(2,5-dichlorophenyl)-2-propynyl]-3-[3-(3-fluoro-6-methoxyquinolin-4-yl)propyl]-3-pyrrolidinecarboxylic acid (undetermined absolute configuration)

By carrying out the procedure according to the method described in Example 23, but starting with 2,5-dichlorobromobenzene, the enantiomer B of 1-[3-(2,5-dichlorophenyl)-2-propynyl]-3-[3-(3-fluoro-6-methoxyquinolin-4-yl)propyl]-3-pyrrolidinecarboxylic acid (undetermined absolute configuration) is obtained in the form of a solid.

CI mass spectrum: m/z=515 MH+; m/z=287 $C_{17}H_{20}N_2OF$+ base peak.

Infrared spectrum KBr: 2928; 1709; 1621; 1509; 1468; 1231; 1096; 1031; 830; 786 and 600 cm$^{-1}$.

$[\alpha]_D^{20}$=+27.5+/−0.9 [methanol, (c=0.5), 589 nm]

EXAMPLE 57

Enantiomer A (dextrorotatory) of 1-[2-[(2,6-difluorophenyl)thio]ethyl]-3-[3-(3-fluoro-6-methoxyquinolin-4-yl)propyl]-3-pyrrolidinecarboxylic acid (undetermined absolute configuration)

By carrying out the procedure according to the method described in Example 3, but starting with methyl (±)-1-[2-[(2,6-difluorophenyl)thio]ethyl]-3-[3-(3-fluoro-6-methoxyquinolin-4-yl)propyl]-3-pyrrolidinecarboxylate, the enantiomer A (dextrorotatory) of 1-[2-[(2,6-difluorophenyl)thio]ethyl]-3-[3-(3-fluoro-6-methoxyquinolin-4-yl)propyl]-3-pyrrolidinecarboxylic acid (undetermined absolute configuration) is obtained in the form of a white solid melting at 106° C.

$[\alpha]_D^{20}$=+29.1+/−0.7 [methanol (c=0.5), 589 nm].

IR spectrum (KBr) cm−1 2940; 1704; 1621; 1606; 1509; 1463; 1233; 1144; 990; 830 and 785 cm$^{-1}$.

EI mass spectrum: m/z=504 (M+); 345 (M−$C_7H_5F_2S$)+ base peak.

Methyl (±)-1-[2-[(2,6-difluorophenyl)thio]ethyl]-3-[3-(3-fluoro-6-methoxyquinolin-4-yl)propyl]-3-pyrrolidinecarboxylate may be prepared as described in Example 2, but starting with 2-[(2-bromoethyl)thio]-1,3-difluorobenzene. A pale yellow oil is obtained.

EI mass spectrum: m/z 518 (M+).

2-[(2-Bromoethyl)thio]-1,3-difluoro-benzene may be prepared according to the method described in patent WO200240474-A2.

EXAMPLE 58

Enantiomer B (levorotatory) of 1-[2-[(2,6-difluorophenyl)thio]ethyl]-3-[3-(3-fluoro-6-methoxyquinolin-4-yl)propyl]-3-pyrrolidinecarboxylic acid (undetermined absolute configuration)

By carrying out the procedure according to the method described in Example 3, but starting with methyl (±)-1-[2-[(2,6-difluorophenyl)thio]ethyl]-3-[3-(3-fluoro-6-methoxyquinolin-4-yl)propyl]-3-pyrrolidinecarboxylate, the enantiomer B (levorotatory) of 1-[2-[(2,6-difluorophenyl)thio]ethyl]-3-[3-(3-fluoro-6-methoxyquinolin-4-yl)propyl]-3-pyrrolidinecarboxylic acid (undetermined absolute configuration) is obtained in the form of a white solid melting at 86° C.

$[\alpha]_D^{20}$=−29.3+/−0.8 [methanol (c=0.5), 589 nm].

IR spectrum (KBr) cm$^{-1}$ 2940; 1704; 1621; 1606; 1509; 1463; 1233; 1144; 990; and 785 cm$^{-1}$.

CI mass spectrum m/z=505 (MH+) base peak.

EXAMPLE 59

Enantiomer A (dextrorotatory) of 1-[2-[(2,5-dichlorophenyl)thio]ethyl]-3-[3-(3-fluoro-6-methoxyquinolin-4-yl)propyl]-3-pyrrolidinecarboxylic acid (undetermined absolute configuration)

By carrying out the procedure according to the method described in Example 3, but starting with methyl (±)-1-[2-[(2,5-dichlorophenyl)thio]ethyl]-3-[3-(3-fluoro-6-methoxyquinolin-4-yl)propyl]-3-pyrrolidinecarboxylate, the enantiomer A (dextrorotatory) of 1-[2-[(2,5-dichlorophenyl)thio]ethyl]-3-[3-(3-fluoro-6-methoxyquinolin-4-yl)propyl]-3- pyrrolidinecarboxylic acid (undetermined absolute configuration) is obtained in the form of a white solid melting at 79° C.

[α]$_D^{20}$=+22.3+/−0.7 [methanol (c=0.5), 589 nm)].

IR spectrum (KBr) cm$^{-1}$ 2939; 1706; 1621; 1569; 1509; 1450; 1362; 1230; 1141; 1095; 1034; 830; 806 and 575 cm$^{-1}$.

ES mass spectrum: m/z=537 (MH+) base peak.

Methyl (±)-1-[2-[(2,5-dichlorophenyl)thio]ethyl]-3-[3-(3-fluoro-6-methoxyquinolin-4-yl)propyl]-3-pyrrolidinecarboxylate may be prepared as described in Example 2, but starting with 2-[(2-bromo-ethyl)thio]-1,4-dichlorobenzene. A pale yellow oil is obtained.

EI mass spectrum: m/z 550 (M+).

2-[(2-Bromoethyl)thio]-1,4-dichlorobenzene may be prepared according to the method described in patent WO200240474-A2.

EXAMPLE 60

Enantiomer B (levorotatory) of 1-[2-[(2,5-dichlorophenyl)thio]ethyl]-3-[3-(3-fluoro-6-methoxyquinolin-4-yl)propyl]-3-pyrrolidinecarboxylic acid (undetermined absolute configuration)

By carrying out the procedure according to the method described in Example 3, but starting with methyl (±)-1-[2-[(2,5-dichlorophenyl)thio]ethyl]-3-[3-(3-fluoro-6-methoxyquinolin-4-yl)propyl]-3-pyrrolidinecarboxylate, the enantiomer B (levorotatory) of 1-[2-[(2,5-dichlorophenyl)thio]ethyl]-3-[3-(3-fluoro-6-methoxyquinolin-4-yl)propyl]-3-pyrrolidinecarboxylic acid (undetermined absolute configuration) is obtained in the form of a white solid melting at 67° C.

[α]$_D^{20}$=−22.6+/−0.7 [methanol (c=0.5), 589 nm)].

IR spectrum (KBr) cm$^{-1}$ 2939; 1706; 1621; 1569; 1509; 1450; 1362; 1230; 1141; 1095; 1034; 830; 806; and 575 cm$^{-1}$.

CI mass spectrum: m/z=537 (MH+) base peak.

EXAMPLES 61 AND 62

Diastereoisomers A (dextrorotatory) and C (levorotatory) of the sodium salt of 1-[(2E)-3-(2,5-difluorophenyl)-2-propenyl]-3-[3-(3-fluoro-6-methoxyquinolin-4-3-hydroxypropyl]-3-pyrrolidinecarboxylic acid (undetermined absolute configuration)

1-[(2E)-3-(2,5-Difluorophenyl)-2-propenyl]-3-[3-(3-fluoro-6-methoxyquinolin-4-yl)-3-hydroxypropyl]-3-pyrrolidinecarboxylic acid (mixture of the 2 diastereoisomers A and C of undetermined absolute configuration) (0.370 g) is injected into a column 6 cm in diameter and 30 cm in length containing 600 g of chiral stationary phase: CHIROBIOTIC TM having a particle size of 10 μm. The elution is carried out with a mobile phase [H$_2$O/THF/TEA/acetic acid (80/15/0.15/0.05 by volume)] at a flow rate of 100 ml/min, the detection is performed by UV at 254 nm.

The diastereoisomer A (dextrorotatory), having an undetermined absolute configuration, which was eluted in the first position, is recovered and then concentrated under vacuum to give 0.150 g of a white powder. This powder is then purified on the same column, eluting with a mobile phase [methanol/TEA/acetic acid (100/0.05/0.05 by volume)] at a flow rate of 100 ml/min. The diastereoisomer A (dextrorotatory), having an undetermined absolute configuration, which was eluted in the first position, is recovered and then concentrated under vacuum to give 0.060 g of a white foam.

[α]$_D^{20}$=+54.5+/−1.2 [methanol, (c=0.5), 589 nm].

IR spectrum (KBr) 3428; 2959; 1622; 1591; 1509; 1491; 1429; 1355; 1231; 1148; 1029; 975; 830 and 728 cm$^{-1}$.

ES mass spectrum: m/z=501 (MH)+.

The diastereoisomer C (levorotatory), having an undetermined absolute configuration, which was eluted in the second position, is recovered and then concentrated under vacuum to give 0.080 g of a white foam.

[α]$_D^{20}$=−24.6+/−0.8 [methanol, (c=0.5), 589 nm].

IR spectrum (KBr) 3415; 2955; 1622; 1591; 1509; 1491; 1429; 1355; 1231; 1199; 1030; 975; 830 and 728 cm$^{-1}$.

ES mass spectrum: m/z=501 (MH)+.

1-[(2E)-3-(2,5-Difluorophenyl)-2-propenyl]-3-[3-(3-fluoro-6-methoxyquinolin-4-yl)-3-hydroxypropyl]-3-pyrrolidinecarboxylic acid (mixture of the 2 diastereoisomers A and C having an undetermined absolute configuration) may be prepared as described in Examples 64 and 65, but starting with the enantiomer A of 1-(1,1-dimethylethyl) and methyl 3-[3-(3-fluoro-6-methoxyquinolin-4-yl)propyl]-1,3-pyrrolidinedicarboxylate (of undetermined absolute configuration), a yellow oil is obtained.

EI mass spectrum: m/z=500 (M+).

EXAMPLES 63 AND 64

Diastereoisomers B (levorotatory) and D (dextrorotatory) of the sodium salt of 1-[(2E)-3-(2,5-difluorophenyl)-2-propenyl]-3-[3-(3-fluoro-6-methoxyquinolin-4-yl)-3-hydroxypropyl]-3-pyrrolidinecarboxylic acid (undetermined absolute configuration)

By carrying out the procedure according to the method described in Examples 62 and 63, but starting with the sodium salt of 1-[(2E)-3-(2,5-difluorophenyl)-2-propenyl]-3-[3-(3-fluoro-6-methoxyquinolin-4-yl)-3-hydroxypropyl]-3-pyrrolidinecarboxylic acid (mixture of the 2 diastereoisomers A and C of undetermined absolute configuration):

The diastereoisomer B (levorotatory), having an undetermined absolute configuration, which was eluted in the first position, is recovered and then concentrated under vacuum to give 0.130 g of a white foam.

[α]$_D^{20}$=−53.1+/−1.0 [methanol, (c=0.5), 589 nm].

IR spectrum (KBr): 3414; 2938; 1622; 1591; 1509; 1491; 1429; 1354; 1230; 1198; 1029; 974; 830 and 728 cm$^{-1}$.

ES mass spectrum: m/z=501 (MH)+.

The diastereoisomer D (dextrorotatory), having an undetermined absolute configuration, which was eluted in the second position, is recovered and then concentrated under vacuum to give 0.100 g of a white foam.

[α]$_D^{20}$=+24.8+/−0.7 [methanol, (c=0.5), 589 nm].

IR spectrum (KBr): 3397; 2958; 1622; 1591; 1509; 1491; 1429; 1355; 1230: 1199; 1029; 975; 831 and 728 cm$^{-1}$.

ES mass spectrum: m/z=501 (MH)+.

The sodium salt of 1-[(2E)-3-(2,5-difluorophenyl)-2-propenyl]-3-[3-(3-fluoro-6-methoxyquinolin-4-yl)-3-hydroxypropyl]-3-pyrrolidinecarboxylic acid (mixture of the 2 diastereoisomers A and C of undetermined absolute configuration) may be prepared in the following manner:

9.14 cm$^3$ of a 5 N aqueous sodium hydroxide solution is added at a temperature in the region of 20° C. to 0.56 g (1.088 mmol) of methyl 1-[(2E)-3-(2,5-difluorophenyl)-2-propenyl]-3-[3-(3-fluoro-6-methoxyquinolin-4-yl)-3-hydroxypropyl]-3-pyrrolidinecarboxylate (mixture of the 2 diastereoisomers A and C of undetermined absolute configuration) in solution in 120 cm³ of dioxane. After stirring under reflux for 16 hours, the reaction mixture is cooled and then concentrated to dryness under reduced pressure (2.7 kPa) to give a residue which is taken up in 50 cm³ of water. The pH is adjusted to a value in the region of 7 by addition of a 1 N aqueous hydrochloric acid solution. The aqueous phase is concentrated to dryness under reduced pressure (2.7 kPa) to give 7 g of a residue which is taken up in 50 cm³ of methanol. The NaCl in suspension is removed by filtration. The filtrate is concentrated to dryness under reduced pressure (2.7 kPa) to give 1.2 g of a pale yellow solid which is purified by flash chromatography [eluent: dichloromethane/methanol (80/20 by volume)+0.5% of $NH_4OH$]. After concentrating the fractions under reduced pressure, 0.464 g of the sodium salt of 1-[(2E)-3-(2,5-difluorophenyl)-2-propenyl]-3-[3-(3-fluoro-6-methoxyquinolin-4-yl)-3-hydroxypropyl]-3-pyrrolidinecarboxylic acid (mixture of the 2 diastereoisomers A and C of undetermined absolute configuration) is obtained in the form of a pale yellow foam.

EI mass spectrum: m/z=522 (M+).

Methyl 1-[(2E)-3-(2,5-difluorophenyl)-2-propenyl]-3-[3-(3-fluoro-6-methoxyquinolin-4-yl)-3-hydroxypropyl]-3-pyrrolidinecarboxylate (mixture of the 2 diastereoisomers A and C of undetermined absolute configuration) may be prepared as described in Examples 71 and 72, but starting with the enantiomer B of 1-(1,1-dimethylethyl) and methyl 3-[3-(3-fluoro-6-methoxyquinolin-4-yl)propyl]-1,3-pyrrolidinedicarboxylate (of undetermined absolute configuration), a yellow oil is obtained which solidifies.

EI mass spectrum: m/z=500 (M+).

The enantiomers A and B of 1-(1,1-dimethylethyl) and methyl 3-[3-(3-fluoro-6-methoxyquinolin-4-yl)propyl]-1,3-pyrrolidinedicarboxylate (of undetermined absolute configuration) may be prepared in the following manner:

1-(1,1-Dimethylethyl) and methyl (±)-3-[3-(3-fluoro-6-methoxyquinolin-4-yl)propyl]-1,3-pyrrolidinedicarboxylate (2.55 g) is injected into a column 8 cm in diameter and 30 cm in length containing 1200 g of chiral stationary phase: WHELK OI,SS TM having a particle size of 10 µm. The elution is carried out with a mobile phase [heptane/Mtbe/methanol/ethanol/TEA (76/20/2/2/0.1 by volume)] at a flow rate of 140 ml/min, the detection is performed by UV at 254 nm.

The enantiomer A (dextrorotatory), having an undetermined absolute configuration, which was eluted in the first position, is recovered and then concentrated under vacuum to give 1.15 g of a colorless oil.

$[α]_D^{20}$=+23.6+/−0.9 [methanol, (c=0.5), 589 nm].

EI mass spectrum: m/z=460 (M+), 359 (M−$C_5H_9O_2$)+, 57 ($C_4H_9$+).

The enantiomer B (levorotatory), having an undetermined absolute configuration, which was eluted in the second position, is recovered and then concentrated under vacuum to give 1.25 g of a colorless oil.

$[α]_D^{20}$=−21.4+/−0.8 [methanol, (c=0.5), 589 nm].

EI mass spectrum: m/z=460 (M+), 359 (M−$C_5H_9O_2$)+, 57 ($C_4H_9$+).

EXAMPLE 65

Enantiomer A (levorotatory) of the sodium salt of 1-[3-[(2,5-difluorophenyl)thio]propyl]-3-[3-(3-fluoro-6-methoxyquinolin-4-yl)propyl]-3-pyrrolidinecarboxylic acid (undetermined absolute configuration)

By carrying out the procedure according to the method described in Example 3, but starting with methyl (±)-1-[3-[(2,5-difluorophenyl)thio]propyl]-3-[3-(3-fluoro-6-methoxyquinolin-4-yl)propyl]-3-pyrrolidinecarboxylate, the enantiomer A (levorotatory) of the sodium salt of 1-[3-[(2,5-difluorophenyl)thio]propyl]-3-[3-(3-fluoro-6-methoxyquinolin-4-yl)propyl]-3-pyrrolidinecarboxylic acid (undetermined absolute configuration) is obtained in the form of a white solid melting between 110° C. and 113° C.

$[α]_D^{20}$=−17.8+/−0.6 [methanol (c=0.5), 589 nm].

IR spectrum (KBr) cm⁻¹ 2955; 1620; 1509; 1483; 1230; 1188; 1032; 908; 825; 810; 785 and 757 cm⁻.

CI mass spectrum: m/z=519 (MH+) base peak.

Methyl (±)-1-[3-[(2,5-difluorophenyl)thio]propyl]-3-[3-(3-fluoro-6-methoxyquinolin-4-yl)propyl]-3-pyrrolidinecarboxylate may be prepared as described in Example 2, but starting with 2-[(3-bromopropyl)thio]-1,4-difluoro-benzene. An orange oil is obtained.

EI mass spectrum: m/z 532 (M+).

2-[(3-Bromopropyl)thio]-1,4-difluorobenzene may be prepared according to the method described in patent WO200240474-A2.

EXAMPLE 66

Enantiomer B (dextrorotatory) of the sodium salt of 1-[3-[(2,5-difluorophenyl)thio]propyl]-3-[3-(3-fluoro-6-methoxyquinolin-4-yl)propyl]-3-pyrrolidinecarboxylic acid (undetermined absolute configuration)

By carrying out the procedure according to the method described in Example 3, but starting with methyl (±)-1-[3-[(2,5-difluorophenyl)thio]propyl]-3-[3-(3-fluoro-6-methoxyquinolin-4-yl)propyl]-3-pyrrolidinecarboxylate, the enantiomer B (dextrorotatory) of the sodium salt of 1-[3-[(2,5-difluorophenyl)thio]propyl]-3-[3-(3-fluoro-6-methoxyquinolin-4-yl)propyl]-3-pyrrolidinecarboxylic acid (undetermined absolute configuration) is obtained in the form of a white solid melting between 121° C. and 123° C.

$[α]_D^{20}$=+18.8+/−0.8 [methanol (c=0.5), 589 nm].

IR spectrum (KBr) cm⁻¹ 2955; 1620; 1509; 1483; 1230; 1188; 1032; 908; 825; 810; 785 and 757 cm⁻¹.

ES mass spectrum: m/z=519 (MH+) base peak.

EXAMPLE 67

1-[2-[(2-Pyridinyl)thio]ethyl]-3-[3-(3-fluoro-6-methoxyquinolin-4-yl)propyl]-3-pyrrolidinecarboxylic acid (undetermined absolute configuration)

By carrying out the procedure according to the methods described in Examples 1 and 2, but starting with 2-[(2-bromoethyl)thio]pyridine, an orange oil is obtained.

ES mass spectrum: m/z=470 (MH+) base peak.

2-[(2-Bromoethyl)thio]pyridine may be prepared according to the method described in patent WO200240474-A2.

EXAMPLE 68

Enantiomer A (dextrorotatory) of 1-[2-[(2,5-difluorophenyl)amino]ethyl]-3-[3-(3-fluoro-6-methoxyquinolin-4-yl)propyl]-3-pyrrolidinecarboxylic acid (undetermined absolute configuration)

By carrying out the procedure according to the method described in Example 3, but starting with methyl (±)-1-[2-

[(2,5-difluorophenyl)amino]ethyl]-3-[3-(3-fluoro-6-methoxyquinolin-4-yl)propyl]-3-pyrrolidinecarboxylate, the enantiomer A (dextrorotatory) of 1-[2-[(2,5-difluorophenyl)amino]ethyl]-3-[3-(3-fluoro-6-methoxyquinolin-4-yl)propyl]-3-pyrrolidinecarboxylic acid (undetermined absolute configuration) is obtained in the form of a white solid.

$[\alpha]_D^{20}$=+28.5+/−0.7 [dichloromethane (c=0.5), 589 nm].

IR spectrum (KBr) cm$^{-1}$ 2929; 1635; 1621; 1531; 1510; 1231; 1187; 1030; 830 and 786 cm$^{-1}$.

ES mass spectrum: m/z=488 (MH+) base peak.

Methyl (±)-1-[2-[(2,5-difluorophenyl)amino]ethyl]-3-[3-(3-fluoro-6-methoxyquinolin-4-yl)propyl]-3-pyrrolidinecarboxylate may be prepared in the following manner:

1.65 cm$^3$ of 1,8-diazabicyclo[5.4.0]undec-7-ene (DBU) and 1.16 cm$^3$ of mercaptoethanol are added at a temperature in the region of 20° C., under an argon atmosphere, to 1.9 g (2.77 mmol) of methyl 1-[2-[(2,5-difluorophenyl)][(2-nitrophenyl)sulfonyl]amino]ethyl]-3-[3-(3-fluoro-6-methoxyquinolin-4-yl)propyl]-3-pyrrolidinecarboxylate in solution in 60 cm$^3$ of dimethylformamide. After stirring for 5 hours at a temperature in the region of 20° C., the reaction mixture is poured over 600 cm$^3$ of water and then extracted with 4 times 200 cm$^3$ of dichloromethane. The organic phases are combined, washed with 200 cm$^3$ of water, dried over anhydrous magnesium sulfate, filtered and concentrated to dryness under reduced pressure (2.7 kPa) to give 1.67 g of a yellow oil which is purified by flash chromatography [eluant: dichloromethane/methanol (95/5 by volume)]. After concentrating the fractions under reduced pressure, 1.58 g of a yellow oil are obtained, which oil is again purified by flash chromatography [eluent: dichloromethane/ethyl acetate (9/1 by volume)]. After concentrating the fractions under reduced pressure, 0.76 g of methyl (±)-1-[2-[(2,5-difluorophenyl)amino]ethyl]-3-[3-(3-fluoro-6-methoxyquinolin-4-yl)propyl]-3-pyrrolidinecarboxylate is obtained in the form of a pale yellow oil.

EI mass spectrum: m/z 501 (M+).

Methyl 1-[2-[(2,5-difluorophenyl)][(2-nitrophenyl)sulfonyl]amino]ethyl]-3-[3-(3-fluoro-6-methoxyquinolin-4-yl)propyl]-3-pyrrolidinecarboxylate may be prepared as described in Example 2, but starting with N-(2-bromoethyl)-N-(2,5-difluorophenyl)-2-nitrobenzenesulfonamide. A pale yellow oil is obtained.

CI mass spectrum: m/z 687 (MH+).

N-(2-Bromoethyl)-N-(2,5-difluorophenyl)-2-nitrobenzenesulfonamide may be prepared according to the method described in patent WO200240474-A2.

EXAMPLE 69

Enantiomer B (dextrorotatory) of 1-[2-[(2,5-difluorophenyl)amino]ethyl]-3-[3-(3-fluoro-6-methoxyquinolin-4-yl)propyl]-3-pyrrolidinecarboxylic acid (undetermined absolute configuration)

By carrying out the procedure according to the method described in Example 3, but starting with methyl (±)-1-[2-[(2,5-difluorophenyl)amino]ethyl]-3-[3-(3-fluoro-6-methoxyquinolin-4-yl)propyl]-3-pyrrolidinecarboxylate, the enantiomer B (dextrorotatory) of 1-[2-[(2,5-difluorophenyl)amino]ethyl]-3-[3-(3-fluoro-6-methoxyquinolin-4-yl)propyl]-3-pyrrolidinecarboxylic acid (undetermined absolute configuration is obtained in the form of a white solid.

$[\alpha]_D^{20}$=−40.5+/−0.9 [dichloromethane (c=0.5), 589 nm].

IR spectrum (KBr) cm$^{-1}$ 2929; 1635; 1621; 1531; 1510; 1231; 1187; 1030; 830 and 786 cm$^{-1}$.

ES mass spectrum: m/z=488 (MH+) base peak.

EXAMPLES 70 AND 71

Diastereoisomers A (dextrorotatory) and C (levorotatory) of 3-[3-(3-chloro-6-methoxyquinolin-4-yl)]-3-hydroxypropyl]-1-[(2E)-3-(2,5-difluorophenyl)-2-propenyl]-3-pyrrolidinecarboxylic acid (undetermined absolute configuration)

3-[3-(3-Chloro-6-methoxyquinolin-4-yl)]-3-hydroxypropyl]-1-[(2E)-3-(2,5-difluorophenyl)-2-propenyl]-3-pyrrolidinecarboxylic acid (mixture of the 2 diastereoisomers A and C of undetermined absolute configuration) (0.367 g) is injected into a column 6 cm in diameter and 30 cm in length containing 600 g of chiral stationary phase: CHIROBIOTIC TM having a particle size of 10 µm. The elution is carried out with a mobile phase [H$_2$O/THF/TEA/acetic acid (85/15/0.1/0.1 by volume)] at a flow rate of 90 ml/min, the detection is performed by UV at 254 nm.

The diastereoisomer A (dextrorotatory), having an undetermined absolute configuration, which was eluted in the first position, is recovered and then concentrated under vacuum to give 0.161 g of a colorless oil.

$[\alpha]_D^{20}$=+63.7+/−1.7 [methanol, (c=0.5), 589 nm].

IR spectrum (CH$_2$Cl$_2$): 3593; 1718; 1621; 1503; 1491; 1421; 1355; 1231; 1185; 1117; 1068; 1036; 975 and 835 cm$^{-1}$.

ES mass spectrum: m/z=517 (MH)+.

The diastereoisomer C (levorotatory), having an undetermined absolute configuration, which was eluted in the second position, is recovered and then concentrated under vacuum to give 0.0137 g of a colorless oil.

$[\alpha]_D^{20}$ having a negative sign in methanol [methanol, (c=0.5), 589 nm].

IR spectrum (CH$_2$Cl$_2$): 3587; 1723; 1621; 1503; 1491; 1421; 1355; 1231; 1117; 975; 897 and 836 cm−1.

ES mass spectrum: m/z=517 (MH)+.

3-[3-(3-Chloro-6-methoxyquinolin-4-yl)]-3-hydroxypropyl]-1-[3-(2,5-difluorophenyl)-2-propenyl]-3-pyrrolidinecarboxylic acid (mixture of the 2 diastereoisomers A and C of undetermined absolute configuration) may be prepared in the following manner:

0.354 g of triethylamine, 0.74 g of sodium triacetoxyborohydride and a solution of 0.294 g of (E)-3-(2,5-difluorophenyl)propenal are added at a temperature in the region 20° C., under an argon atmosphere, to 0.51 g (1.165 mmol) of the dihydrochloride of 3-[3-(3-chloro-6-methoxyquinolin-4-yl)]-3-hydroxypropyl]-3-pyrrolidinecarboxylic acid (mixture of the 2 diastereoisomers A and C of undetermined absolute configuration) in solution in 25 cm$^3$ of dichloromethane. After stirring for 2 hours at a temperature in the region of 20° C., the reaction mixture is concentrated to dryness under reduced pressure (2.7 kPa) to give 1.82 g of a residue which is purified by flash chromatography [eluent: chloroform/methanol/28% aqueous NH$_4$OH (12/2.25/0.38 by volume)]. After concentrating the fractions under reduced pressure, 0.42 g of 3-[3-(3-chloro-6-methoxyquinolin-4-yl)]-3-hydroxypropyl]-1-[3-(2,5-difluorophenyl)-2-propenyl]-3-pyrrolidinecarboxylic acid (mixture of the 2 diastereoisomers A and C of undetermined absolute configuration) is obtained in the form of a yellow oil.

EI mass spectrum: m/z 516 (M+).

The dihydrochloride of 3-[3-(3-chloro-6-methoxyquinolin-4-yl)]-3-hydroxypropyl]-3-pyrrolidinecarboxylic acid (mixture of the 2 diastereoisomers A and C of undetermined absolute configuration) may be prepared in the following manner:

16 cm³ of a 4 N hydrochloric acid solution in dioxane are added at a temperature in the region of 20° C. to 0.604 g (1.3 mmol) of 1,1-dimethylethyl 3-[3-(3-chloro-6-methoxyquinolin-4-yl)-3-hydroxypropyl]-3-pyrrolidinedicarboxylate (mixture of the 2 diastereoisomers A and C of undetermined absolute configuration) in solution in 20 cm³ of dioxane. After stirring for 48 hours at a temperature in the region of 20° C., the reaction mixture is concentrated to dryness under reduced pressure (2.7 kPa) to give 0.64 g of a yellow solid which is triturated with 10 cm³ of diethyl ether. After filtration, the solid is washed with 10 cm³ of diethyl ether and then dried under reduced pressure (2.7 kPa) to give 0.6 g of the dihydrochloride of 3-[3-(3-chloro-6-methoxyquinolin-4-yl)]-3-hydroxypropyl]-3-pyrrolidinecarboxylic acid (mixture of the 2 diastereoisomers A and C of undetermined absolute configuration), in the form of a yellow solid.

EI mass spectrum: m/z 437 (M+).

1-(1,1-Dimethylethyl) 3-[3-(3-chloro-6-methoxyquinolin-4-yl)-3-hydroxypropyl]-1,3-pyrrolidinedicarboxylate (mixture of the 2 diastereoisomers A and C of undetermined absolute configuration) may be prepared in the following manner:

Oxygen is bubbled through 2.3 g (5.12 mmol) of the enantiomer A of 1-(1,1-dimethylethyl) 3-[3-(3-chloro-6-methoxyquinolin-4-yl)-3-hydroxypropyl]-1,3-pyrrolidinedicarboxylate (of undetermined absolute configuration) in solution in 185 cm³ of dimethyl sulfoxide, at a temperature in the region of 20° C., for 20 minutes until saturation is obtained. 1.32 g (11.78 mmol) of potassium tert-butoxide in solution in 84 ml of tert-butanol are then added. Oxygen is again bubbled through for 5 hours. The reaction mixture is cooled to a temperature in the region of 0° C. 540 cm³ of water are added dropwise while the temperature is maintained in the region of 20° C., the pH is adjusted to a value between 5 and 6 by addition of 1.5 cm³ of acetic acid and then 250 cm³ of water are added. The reaction mixture is extracted with 4 times 250 cm³ of dichloromethane. The organic phases are combined, washed with 250 cm³ of water, dried over anhydrous magnesium sulfate, filtered and concentrated to dryness under reduced pressure (2.7 kPa) to give 3.14 g of a yellow oil which is taken up in 40 cm³ of diethyl ether. The ether phase is washed with twice 20 cm³ of water, dried over anhydrous magnesium sulfate, filtered and concentrated to dryness under reduced pressure (2.7 kPa) to give 1.27 g of 1-(1,1-dimethylethyl) 3-[3-(3-chloro-6-methoxyquinolin-4-yl)-3-hydroxypropyl]-1,3-pyrrolidinedicarboxylate (mixture of the 2 diastereoisomers A and C of undetermined absolute configuration), in the form of a pale yellow foam.

EI mass spectrum: m/z 464 (M+).

The enantiomer A of 1-(1,1-dimethylethyl) 3-[3-(3-chloro-6-methoxyquinolin-4-yl)-3-hydroxypropyl]-1,3-pyrrolidinedicarboxylate (of undetermined absolute configuration) may be prepared in the following manner:

50 cm³ of a 5 N aqueous sodium hydroxide solution are added at a temperature in the region of 20° C. to 2.78 g (6 mmol) of the enantiomer A of 1-(1,1-dimethylethyl) and 3-methyl 3-[3-(3-chloro-6-methoxyquinolin-4-yl)-3-hydroxypropyl]-1,3-pyrrolidinedicarboxylate (of undetermined absolute configuration) in solution in 230 cm³ of dioxane. After stirring under reflux for 18 hours, the reaction mixture is cooled and then concentrated to dryness under reduced pressure (2.7 kPa) to give a residue which is taken up in 700 cm³ of water. The pH is adjusted to a value in the region of 4 by addition of citric acid. After 4 hours at a temperature in the region of 20° C., the suspension is filtered, the solid is washed with 3 times 50 cm³ of diisopropyl ether and then dried under reduced pressure (2.7 kPa) at a temperature in the region of 43° C. to give 2.3 g of the enantiomer A of 1-(1,1-dimethylethyl) 3-[3-(3-chloro-6-methoxyquinolin-4-yl)-3-hydroxypropyl]-1,3-pyrrolidinedicarboxylate (of undetermined absolute configuration), in the form of a white solid.

EI mass spectrum: m/z 448 (M+).

The enantiomers A and B of 1-(1,1-dimethylethyl) and 3-methyl 3-[3-(3-chloro-6-methoxyquinolin-4-yl)propyl]-1,3-pyrrolidinedicarboxylate of 1-(1,1-dimethylethyl) (of undetermined absolute configuration) may be prepared in the following manner:

1-(1,1-Dimethylethyl) and 3-methyl (±)-3-[3-(3-chloro-6-methoxyquinolin-4-yl)propyl]-1,3-pyrrolidinedicarboxylate (2.55 g) is injected into a column 6 cm in diameter and 30 cm in length containing 800 g of chiral stationary phase: WHELK OI,SS TM having a particle size of 10 µm. The elution is carried out with a mobile phase [heptane/MTBE/methanol/isopropanol/TEA (74/20/1/4/0.1 by volume)] at a flow rate of 120 ml/min, the detection is performed by UV at 254 nm.

The enantiomer A (dextrorotatory), having an undetermined absolute configuration, which was eluted in the first position, is recovered and then concentrated under vacuum to give 0.46 g of colorless oil.

EI mass spectrum: m/z=462 (M+), 361 (M−$C_5H_9O_2$)+, 57 ($C_4H_9$+).

$[\alpha]_D^{20}$=+18.8+/−0.6 [methanol, (c=0.5), 589 nm].

The enantiomer B (levorotatory), having an undetermined absolute configuration, which was eluted in the second position, is recovered and then concentrated under vacuum to give 0.217 g of a colorless oil.

$[\alpha]_D^{20}$=−18.4+/−0.8 [methanol, (c=0.5), 589 nm].

EI mass spectrum: m/z=462 (M+), 361 (M−$C_5H_9O_2$)+, 57 ($C_4H_9$+).

EXAMPLES 72 AND 73

Diastereoisomers B (levorotatory) and D (dextrorotatory) of 3-[3-(3-chloro-6-methoxyquinolin-4-yl)]-3-hydroxypropyl]-1-[3-(2,5-difluorophenyl)-2-propenyl]-3-pyrrolidinecarboxylic acid (undetermined absolute configuration)

By carrying out the procedure according to the method described in Examples 70 and 71, but starting with 3-[3-(3-chloro-6-methoxyquinolin-4-yl)]-3-hydroxypropyl]-1-[3-(2,5-difluorophenyl)-2-propenyl]-3-pyrrolidinecarboxylic acid (mixture of the 2 diastereoisomers B and D of undetermined absolute configuration):

The diastereoisomer B (levorotatory), having an undetermined absolute configuration, which was eluted in the first position, is recovered and then concentrated under vacuum to give 0.192 g of a colorless oil.

$[\alpha]_D^{20}$=−68.3+/−0.9 [methanol, (c=0,5), 589 nm]; □□□D20=−48.3+/−0.9 [DMSO, (c=0,5), 589 nm].

IR spectrum (KBr): 3431; 1621; 1503; 1491; 1231; 1117; 977 and 728 cm$^{-1}$.

ES mass spectrum: m/z=517 (MH)+.

The diastereoisomer D (dextrorotatory), having an undetermined absolute configuration, which was eluted in the second position, is recovered and then concentrated under vacuum to give 0.198 g of a colorless oil.

$[\alpha]_D^{20}$=+11.8+/−0.8 [DMSO, (c=0.5), 589 nm)].

IR spectrum (KBr): 3401; 1715; 1621; 1503; 1491; 1456; 1231; 1116; 973; 832 and 728 cm$^{-1}$.

ES mass spectrum: m/z=517 (MH)+.

3-[3-(3-Chloro-6-methoxyquinolin-4-yl)]-3-hydroxypropyl]-1-[(2E)-3-(2,5-difluorophenyl)-2-propenyl]-3-pyrrolidinecarboxylic acid (mixture of the 2 diastereoisomers B and D of undetermined absolute configuration) may be prepared as described in Examples 71 and 72, but starting with the enantiomer B of 1-(1,1-dimethylethyl) and 3-methyl 3-[3-(3-chloro-6-methoxyquinolin-4-yl)propyl]-1,3-pyrrolidinedicarboxylate (of undetermined absolute configuration), and a beige foam is obtained.

EI mass spectrum: m/z=516 (M+).

EXAMPLES 74 AND 75

Diastereoisomers A (dextrorotatory) and C (levorotatory) of 1-[3-(2,5-difluorophenyl)propyl]-3-[3-(3-fluoro-6-methoxyquinolin-4-yl)]-3-hydroxypropyl]-3-pyrrolidinecarboxylic acid (undetermined absolute configuration)

1-[3-(2,5-Difluorophenyl)propyl]-3-[3-(3-fluoro-6-methoxyquinolin-4-yl)]-3-hydroxypropyl]-3-pyrrolidinecarboxylic acid (mixture of the 2 diastereoisomers A and C of undetermined absolute configuration) (0.230 g) is injected into a column 6 cm in diameter and 30 cm in length containing 600 g of chiral stationary phase: CHIROBIOTIC TM having a particle size of 10 μm. The elution is carried out with a mobile phase [H$_2$O/THF/TEA/acetic acid (80/20/0.1/0.1 by volume)] at a flow rate of 100 ml/min, the detection is performed by UV at 254 nm.

The diastereoisomer A (dextrorotatory), having an undetermined absolute configuration, which was eluted in the first position, is recovered and then concentrated under vacuum to give 0.072 g of a white foam.

$[\alpha]_D^{20}$=+48.9+/−1.0 [methanol, (c=0.5), 589 nm].

IR spectrum (KBr): 3414; 2927; 2856; 1715; 1622; 1598; 1497; 1427; 1355; 1263; 1231; 1198; 1142; 1030; 831; 813 and 789 cm$^{-1}$.

EI mass spectrum: m/z=502 (M+), 361 (M−C$_8$H$_7$F$_2$)+, 343 (361−H$_2$O)+.

The diastereoisomer C (levorotatory), having an undetermined absolute configuration, which was eluted in the second position, is recovered and then concentrated under vacuum to give 0.052 g of a white foam.

$[\alpha]_D^{20}$=−24.0+/−0.8 [methanol, (c=0.5), 589 nm].

IR spectrum (KBr): 3420; 2958; 1717; 1622; 1598; 1497; 1427; 1355; 1263; 1231; 1198; 1142; 1031; 831; 812 and 789 cm$^{-1}$.

EI mass spectrum: m/z=502 (M+), 361 (M−C$_8$H$_7$F$_2$)+, 343 (361−H$_2$O)+.

1-[3-(2,5-Difluorophenyl)propyl]-3-[3-(3-fluoro-6-methoxyquinolin-4-yl)]-3-hydroxypropyl]-3-pyrrolidinecarboxylic acid (mixture of the 2 diastereoisomers A and C of undetermined absolute configuration) may be prepared in the following manner:

25 cm$^3$ of methanol and 0.3 g (0.6 mmol) of 1-[(2E)-3-(2,5-difluorophenyl)-2-propenyl]-3-[3-(3-fluoro-6-methoxyquinolin-4-yl)]-3-hydroxypropyl]-3-pyrrolidinecarboxylic acid (mixture of the 2 diastereoisomers A and C of undetermined absolute configuration) are added at room temperature, under an argon atmosphere, to 0.03 g of 10% palladium on carbon. The reaction medium is purged 5 times with argon and then hydrogenated at a pressure of 2 bar of hydrogen at room temperature for 24 hours. The catalyst is filtered on Celite®, the Celite® is rinsed with 3 times 25 cm$^3$ of methanol and then the filtrate is concentrated to dryness under reduced pressure (2.7 kPa) to give 0.26 g of 1-[3-(2,5-difluorophenyl)propyl]-3-[3-(3-fluoro-6-methoxyquinolin-4-yl)]-3-hydroxypropyl]-3-pyrrolidinecarboxylic acid (mixture of the 2 diastereoisomers A and C of undetermined absolute configuration), in the form of a yellow lacquer.

EI mass spectrum: m/z=502 (M+).

EXAMPLES 76 AND 77

Diastereoisomers B (levorotatory) and D (dextrorotatory) of 1-[3-(2,5-difluorophenyl)propyl]-3-[3-(3-fluoro-6-methoxyquinolin-4-yl)]-3-hydroxypropyl]-3-pyrrolidinecarboxylic acid (undetermined absolute configuration)

1-[3-(2,5-Difluorophenyl)propyl]-3-[3-(3-fluoro-6-methoxyquinolin-4-yl)]-3-hydroxypropyl]-3-pyrrolidinecarboxylic acid (mixture of the 2 diastereoisomers B and D of undetermined absolute configuration) (0.600 g) is injected into a column 6 cm in diameter and 30 cm in length containing 600 g of chiral stationary phase: CHIROBIOTIC TM having a particle size of 10 μm. The elution is carried out with a mobile phase [H$_2$O/THF/TEA/acetic acid (80/20/0.1/0.1 by volume)] at a flow rate of 100 ml/min, the detection is performed by UV at 254 nm.

The diastereoisomer B (levorotatory), having an undetermined absolute configuration, which was eluted in the first position, is recovered and then concentrated under vacuum, and then crystallized in the presence of water to give 0.472 g of a white powder.

$[\alpha]_D^{20}$ of negative sign in DMSO [DMSO, (c=0.5), 589 nm].

IR spectrum (KBr): 3431; 2950; 1622; 1510; 1497; 1459; 1427; 1355; 1266; 1242; 1230; 1187; 1144; 1080; 1031; 832 and 817 cm$^{-1}$.

EI mass spectrum: m/z=502 (M+), 361 (M−C$_8$H$_7$F$_2$)+, 343 (361−H$_2$O)+.

The diastereoisomer D (dextrorotatory), having an undetermined absolute configuration, which was eluted in the second position, is recovered and then concentrated under vacuum and then crystallized in the presence of water to give 0.113 g of a white powder.

$[\alpha]_D^{20}$ of positive sign in DMSO [DMSO, (c=0.5), 589 nm)].

IR spectrum (KBr): 3418; 2953; 1622; 1593; 1509; 1497; 1467; 1427; 1384; 1355; 1266; 1231; 1197; 1142; 1069; 831 and 813 cm$^{-1}$.

EI mass spectrum: m/z=502 (M+), 361 (M−C$_8$H$_7$F$_2$)+, 343 (361−H$_2$O)+.

1-[3-(2,5-Difluorophenyl)propyl]-3-[3-(3-fluoro-6-methoxyquinolin-4-yl)]-3-hydroxypropyl]-3-pyrrolidinecarboxylic acid (mixture of the 2 diastereoisomers B and D of undetermined absolute configuration) may be prepared in the following manner:

125 cm$^3$ of methanol and 1.5 g (3 mmol) 1-[(2E)-3-(2,5-difluorophenyl)-2-propenyl]-3-[3-(3-fluoro-6-methoxyquinolin-4-yl)]-3-hydroxypropyl]-3-pyrrolidinecarboxylic acid (mixture of the 2 diastereoisomers B and D of undetermined absolute configuration) are added at room temperature, under an argon atmosphere, to 0.15 g of 10% palladium on carbon. The reaction medium is purged 5 times with argon and then hydrogenated at a pressure of 2 bar of hydrogen at room temperature for 24 hours. The catalyst is filtered on Celite®, the Celite® is rinsed with 3 times 100 cm$^3$ of methanol and then the filtrate is concentrated to dryness under reduced pressure (2.7 kPa) to give 1.31 g of 1-[3-(2,5-difluorophenyl)propyl]-3-[3-(3-fluoro-6-methoxyquinolin-4-yl)]-3-hydroxypropyl]-3-pyrrolidinecarboxylic acid (mixture of the 2 diastereoisomers B and D of undetermined absolute configuration), in the form of a beige foam.

EI mass spectrum: m/z=502 (M+).

EXAMPLES 78 AND 79

Diastereoisomers A (levorotatory) and C (dextrorotatory) of 1-[2-[(2,5-difluorophenyl)thio]ethyl]-3-[3-(3-fluoro-6-methoxyquinolin-4-yl)-3-hydroxypropyl]-3-pyrrolidinecarboxylic acid (undetermined absolute configuration)

1-[2-[(2,5-Difluorophenyl)thio]ethyl]-3-[3-(3-fluoro-6-methoxyquinolin-4-yl)-3-hydroxypropyl]-3-pyrrolidinecarboxylic acid (mixture of the 2 diastereoisomers A and C of undetermined absolute configuration) (0.170 g) is injected into a column 6 cm in diameter and 30 cm in length containing 600 g of chiral stationary phase: CHIROBIOTIC TM having a particle size of 10 μm. The elution is carried out with a mobile phase [$H_2O$/THF/TEA/acetic acid (80/20/0.1/0.1 by volume)] at a flow rate of 100 ml/min, the detection is performed by UV at 254 nm.

The diastereoisomer A (levorotatory), having an undetermined absolute configuration, which was eluted in the first position, is recovered and then concentrated under vacuum, and then crystallized in the presence of water to give 0.057 g of a white foam.

$[\alpha]_D^{20}$=−45.6+/−0.9 [methanol, (c=0.5), 589 nm].

IR spectrum (KBr): 3415; 1717; 1622; 1509; 1484; 1355; 1262; 1231; 1187; 1082; 1060; 1030; 908; 830; 804 and 757 $cm^{-1}$.

CI mass spectrum m/z=521 (MH)+, 503 (MH+−$H_2O$).

The diastereoisomer C (dextrorotatory), having an undetermined absolute configuration, which was eluted in the second position, is recovered and then concentrated under vacuum, and then crystallized in the presence of water to give 0.059 g of a white foam.

$[\alpha]_D^{20}$=+19.9+/−0.7 [methanol, (c=0.5), 589 nm].

IR spectrum (KBr): 3409; 1716; 1622; 1509; 1484; 1355; 1262; 1231; 1188; 1081; 1060; 1030; 908; 830; 805 and 757 $cm^1$.

CI mass spectrum m/z=521 (MH)+, 503 (MH+−$H_2O$).

1-[2-[(2,5-Difluorophenyl)thio]ethyl]-3-[3-(3-fluoro-6-methoxyquinolin-4-yl)-3-hydroxypropyl]-3-pyrrolidinecarboxylic acid (mixture of the 2 diastereoisomers A and C of undetermined absolute configuration) may be prepared as described in Examples 70 and 71, but starting with the enantiomer B of 1-[2-[(2,5-difluorophenyl)thio]ethyl]-3-[3-(3-fluoro-6-methoxyquinolin-4-yl)propyl]-3-pyrrolidinecarboxylic acid, a beige solid is obtained.

EI mass spectrum: m/z=520 (M+).

EXAMPLES 80 AND 81

Diastereoisomers B (dextrorotatory) and D (levorotatory) of 1-[2-[(2,5-difluorophenyl)thio]ethyl]-3-[3-(3-fluoro-6-methoxyquinolin-4-yl)-3-hydroxypropyl]-3-pyrrolidinecarboxylic acid (undetermined absolute configuration)

1-[2-[(2,5-Difluorophenyl)thio]ethyl]-3-[3-(3-fluoro-6-methoxyquinolin-4-yl)-3-hydroxypropyl]-3-pyrrolidinecarboxylic acid (mixture of the 2 diastereoisomers B and D of undetermined absolute configuration) (0.100 g) is injected into a column 6 cm in diameter and 30 cm in length containing 600 g of chiral stationary phase: CHIROBIOTIC TM having a particle size of 10 μm. The elution is carried out with a mobile phase [$H_2O$/THF/TEA/acetic acid (80/20/0.1/0.1 by volume)] at a flow rate of 100 ml/min, the detection is performed by UV at 254 nm.

The diastereoisomer B (dextrorotatory), having an undetermined absolute configuration, which was eluted in the first position, is recovered and then concentrated under vacuum, and then crystallized in the presence of water to give 0.057 g of a white foam.

$[\alpha]_D^{20}$=+42.3+/−0.9[methanol, (c=0.5), 589 nm].

IR spectrum (KBr): 3414; 1717; 1622; 1509; 1484; 1356; 1261; 1231; 1188; 1082; 1060; 1027; 908; 861; 805 and 757 $cm^{-1}$.

EI mass spectrum: m/z=520 (M)+, 361 (M−$C_7H_5SF_2$)+. 343 (361−$H_2O$)+.

The diastereoisomer D (levorotatory), having an undetermined absolute configuration, which was eluted in the second position, is recovered and then concentrated under vacuum and then crystallized in the presence of water to give 0.059 g of a white foam.

$[\alpha]_D^{20}$=−20.5+/−0.7 [methanol, (c=0.5), 589 nm].

IR spectrum (KBr): 3414; 1717; 1622; 1509; 1484; 1355; 1261; 1231; 1188; 1082; 1028; 908; 804 and 757 $cm^{-1}$.

EI mass spectrum: m/z=520 (M)+, 361 (M−$C_7H_5SF_2$)+. 343 (361−$H_2O$)+.

1-[2-[(2,5-Difluorophenyl)thio]ethyl]-3-[3-(3-fluoro-6-methoxyquinolin-4-yl)-3-hydroxypropyl]-3-pyrrolidinecarboxylic acid (mixture of the 2 diastereoisomers B and D of undetermined absolute configuration) may be prepared as described in Examples 70 and 71, but starting with the enantiomer A of 1-[2-[(2,5-difluorophenyl)thio]ethyl]-3-[3-(3-fluoro-6-methoxyquinolin-4-yl)propyl]-3-pyrrolidinecarboxylic acid, a beige solid is obtained.

EI mass spectrum: m/z=520 (M+).

What is claimed is:

1. A 4-substituted quinoline compound, of formula (I)

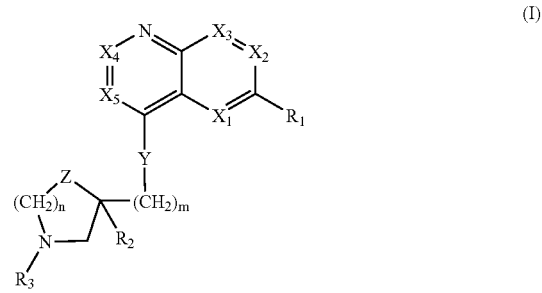

wherein $X_1$, $X_2$, $X_3$, $X_4$ and $X_5$ are C—$R'_1$ to C—$R'_5$ respectively, or alternatively at most one of them is a nitrogen atom, wherein $R_1$, $R'_1$, $R'_2$, $R'_3$, $R'_4$ and $R'_5$ are identical or different from one another and are selected from hydrogen or halogen atoms or an alkyl, cycloalkyl, phenyl, phenylthio, mono- or bicyclic heteroaryl or heteroarylthio, OH, SH, alkyloxy, difluoromethoxy, trifluoromethoxy, alkylthio, trifluoromethylthio, cycloalkyloxy, cycloalkylthio, acyl, acyloxy, acylthio, cyano, carboxyl, alkyloxycarbonyl, cycloalkyloxycarbonyl, nitro, —NRaRb or —CONRaRb radical; wherein Ra and Rb are selected from hydrogen, alkyl, cycloalkyl, phenyl, mono- or bicyclic heteroaryl or Ra and Rb form together with the nitrogen atom to which they are attached a 5- or 6-membered heterocycle which may optionally contain another heteroatom chosen from O, S and N and carrying, where appropriate, an alkyl, phenyl or mono- or bicyclic heteroaryl substituent on the nitrogen atom or, alternately, wherein the sulfur atom is oxidized to the sulfinyl or sulfonyl state, or alternately represent a methylene radical substituted with fluoro, hydroxyl, alkyloxy, alkylthio, cycloakyloxy, cycloalkylthio, phenyl, mono- or bicyclic heteroaryl, carboxyl, alkyloxycarbonyl, cycloalkyloxycarbonyl, —NRaRb or —CONRaRb wherein Ra and Rb are as defined above, or represent phenoxy, heterocyclyloxy, benzyloxy, heterocyclylmethyloxy, or alternatively $R_1$ represents difluoromethoxy, or a radical having the structure —$C_pF_{2p+1}$, —$SC_pF_{2p+1}$ or —$OC_pF_{2p+1}$ wherein p is an integer from 1 to 6 or alternatively $R'_5$ may also represent trifluoroacetyl, m is equal to 1, 2 or 3;

n is equal to 0, 1 or 2;

Y is CHR, CO, CROH, $CRNH_2$, CRF or $CF_2$, wherein R is a hydrogen atom or an alkyl ($C_{1-6}$) radical;

Z is $CH_2$ or alternatively Z is oxygen, sulfur, SO or $SO_2$ group wherein n is equal to 2;

$R_2$ is —$CO_2R$, —$CH_2CO_2R$, —$CH_2$—$CH_2CO_2R$, —$CH_2OH$ or —$CH_2$—$CH_2OH$, wherein R is as defined above;

$R_3$ is phenyl, mono- or bicyclic heteroaryl, alk-$R°_3$ wherein alk is an alkylene radical and $R°_3$ is hydrogen, halogen, hydroxyl, alkyloxy, alkylthio, alkylsulfinyl, alkylsulfonyl, alkylamino, dialkylamino, cycloalkyl, cycloalkyloxy, cycloalkylthio, cycloalkylsulfinyl, cycloalkylsulfonyl, cycloalkylamino, N-cycloalkyl-N-alkylamino, —N-(cycloalkyl)$_2$, acyl, cycloalkylcarbonyl, phenyl, phenoxy, phenylthio, phenylsulfinyl, phenylsulfonyl, phenylamino, N-alkyl-N-phenylamino, N-cycloalkyl-N-phenylamino, —N-(phenyl)2, phenylalkyloxy, phenylalkylthio, phenylalkylsulfinyl, phenylalkylsulfonyl, phenylalkylamino, N-alkyl-N-phenylaminoalkyl, N-cycloalkyl-N-phenylalkylamino, benzoyl, mono- or bicyclic heteroaryl, heteroaryloxy, heteroarylthio, heteroarylsulfinyl, heteroarylsulfonyl, heteroarylamino, N-alkyl-N-heteroarylamino, N-cycloalkyl-N-heteroarylamino, heteroarylcarbonyl, heteroarylalkyloxy, heteroarylalkylthio, heteroarylalkylsulfinyl, heteroarylalkylsulfonyl, heteroarylalkylamino, N-alkyl-N-heteroarylaminoalkyl, N-cycloalkyl-N-heteroarylaminoalkyl, wherein the heteroaryl is either mono- or bicyclic, carboxyl, alkyloxycarbonyl, —NRaRb or —CO—NRaRb wherein Ra and Rb respectively represent hydrogen, alkyl, cycloalkyl, phenyl, mono- or bicyclic heteroaryl, or one of Ra or Rb represents hydroxyl, alkyloxy, cycloalkyloxy, or Ra and Rb form together with the nitrogen atom to which they are attached a 5- or 6-membered heterocycle which may optionally contain another heteroatom chosen from O, S and N and optionally carrying, an alkyl, phenyl or mono- or bicyclic heteroaryl substituent on the nitrogen atom or alternately where the sulfur atom is oxidized to the sulfinyl or sulfonyl state, or alternatively $R°_3$ represents —CR'b═CR'c-R'a wherein R'a is phenyl, phenylalkyl, heteroaryl or heteroarylalkyl wherein the heteroaryl part is mono- or bicyclic, phenoxyalkyl, phenylthioalkyl, phenylsulfinylalkyl, phenylsulfonylalkyl, phenylaminoalkyl, N-alkyl-N-phenylaminoalkyl, heteroyloxyalkyl, heteroarylthioalkyl, heteroarylsulfinylalkyl, heteroarylsulfonylalkyl, heteroarylaminoalkyl, N-alkyl-N-heteroarylaminoalkyl, heteroarylthio, heteroarylsulfinyl, heteroarylsulfonyl, wherein the heteroaryl parts are mono- or bicyclic, phenylthio, phenylsulfinyl, phenylsulfonyl, and wherein R'b and R'c represent hydrogen, alkyl or cycloalkyl, or alternatively $R_3$ represents a radical —C≡C-Rd for which Rd is alkyl, phenyl, phenylalkyl, phenoxyalkyl, phenylthioalkyl, N-alkyl-N-phenylaminoalkyl, mono- or bicyclic heteroaryl, heteroarylalkyl, heteroaryloxyalkyl, heteroarylthioalkyl, heteroarylaminoalkyl, N-alkyl-N-heteroarylaminoalkyl, wherein the heteroaryl parts mentioned above being mono- or bicyclic, or alternatively $R°_3$ is a radical —$CF_2$-phenyl or mono- or bicyclic —$CF_2$-heteroaryl, wherein the phenyl, benzyl, benzoyl or heteroaryl radicals or portions are optionally substituted on the ring with 1 to 4 substituents chosen from halogen, hydroxyl, alkyl, alkyloxy, alkyloxyalkyl, haloalkyl, trifluoromethyl, trifluoromethoxy, trifluoromethylthio, carboxyl, alkyloxycarbonyl, cyano, alkylamino, —NRaRb for which Ra and Rb are as defined above, phenyl, hydroxyalkyl, alkylthioalkyl, alkylsulfinylalkyl, alkylsulfonylalkyl, wherein the alkyl or acyl radicals and portions contain 1 to 10 carbon atoms in the form of a straight or branched chain and the cycloalkyl radicals contain 3 to 6 carbon atoms, wherein the compound is optionally in enantiomeric or diastereoisomeric forms, or mixtures of these forms, or in a syn or an anti form or mixtures thereof, or its salts.

2. The compound of general formula (I), as defined in claim 1, wherein $X_1$, $X_2$, $X_3$, $X_4$ and $X_5$ are as defined in claim 1, wherein $R_1$, $R'_1$, $R'_2$, $R'_3$, $R'_4$ ands $R'_5$, which are identical or different from one another, are selected from hydrogen, halogen, alkyl, alkyloxy, or a methylene substituted with alkyloxy:

Y represents a radical $CH_2$, CHOH, CHF, $CHNH_2$ or C═O;

m is equal to 1;

n is as defined in claim 1;

Z is a $CH_2$ group or oxygen and in the latter case, n is equal to 2;

$R_2$ is as defined in claim 1, and $R_3$ is alk-$R°_3$ wherein alk is an alkylene radical and $R°_3$ is alkyloxy, alkylthio, alkylamino, dialkylamino, cycloalkyloxy, cycloalkylthio, cycloalkylamino, N-cycloalkyl-N-alkylamino, —N-(cycloalkyl)$_2$, phenoxy, phenylthio, phenylamino, N-alkyl-N-phenylamino, N-cycloalkyl-N-phenylamino, phenylalkyloxy, phenylalkylthio, phenylalkylamino, N-alkyl-N-phenylaminoalkyl, N-cycloalkyl-N-phenylalkylamino, heteroaryloxy, heteroarylthio, heteroarylamino, N-alkyl-N-heteroarylamino, N-cycloalkyl-N-heteroarylamino, heteroarylcarbonyl, heteroarylalkyloxy, heteroarylalkylthio, heteroarylalkylamino, N-alkyl-N-heteroarylaminoalkyl, N-cycloalkyl-N-heteroarylaminoalkyl, —NRaRb or —CO—NRaRb wherein Ra and Rb are as defined in claim 1, or alternatively $R°_3$ represents —CR'b═CR'c-R'a for which R'a represents phenyl, phenylalkyl, heteroaryl or heteroarylalkyl, phenoxyalkyl, phenylthioalkyl, phenylaminoalkyl, N-alkyl-N-phenylaminoalkyl, heteroaryloxyalkyl, heteroarylthioalkyl, heteroarylaminoalkyl, N-alkyl-N-heteroarylaminoalkyl, heteroarylthio, or phenylthio, and for which R'b and R'c is hydrogen, alkyl or cycloalkyl, or alternatively $R°_3$ is a radical —C≡C-Rd wherein Rd is alkyl, phenyl, phenylalkyl, phenoxyalkyl, phenylthioalkyl, N-alkyl-N-phenylaminoalkyl, mono- or bicyclic heteroaryl, heteroarylalkyl, heteroaryloxyalkyl, heteroarylthioalkyl, heteroarylaminoalkyl, N-alkyl-N-heteroarylaminoalkyl, or alternatively $R°_3$ is a radical —$CF_2$-phenyl or —$CF_2$-heteroaryl, wherein the phenyl, benzyl, benzoyl or heteroaryl radicals or portions are optionally substituted as set forth in claim 1, wherein the compound is optionally in enantiomeric or diastereoisomeric forms, or mixtures of these forms, or optionally in a syn or an anti form or mixtures thereof, or its salts.

3. The compound of general formula (I) as defined in claim 1, wherein $X_1$, $X_2$, $X_3$, $X_4$ and $X_5$ are >C—$R'_1$ to >C—$R'_5$ respectively, wherein $R_1$, $R'_1$, $R'_2$, $R'_3$, $R'_4$ and $R'_5$ are identical or different from one another and are selected from hydrogen, halogen, alkyl, alkyloxy, or a methylene substituted with alkyloxy;

Y is $CH_2$, CHOH, CHF, $CHNH_2$ or C=O;

m is equal to 1;

n is as defined in claim 1;

Z is a $CH_2$ group or oxygen and in the latter case, n is equal to 2;

$R_2$ is as defined in claim 1, and $R_3$ is alk-$R°_3$, wherein alk is alkylene and $R°_3$ is cycloalkyloxy, cycloalkylthio, phenoxy, phenylthio, phenylalkyloxy, phenylalkylthio, heteroaryloxy, heteroarylthio, heteroarylalkyloxy, heteroarylalkylthio, or alternatively $R_3$ is —CR'b=CR'c-R'a for which R'a represents phenyl, phenylalkyl, phenylthioalkyl, heteroaryl or heteroarylalkyl, phenoxyalkyl, heteroaryloxyalkyl, heteroarylthioalkyl, heteroarylthio, or phenylthio, and wherein R'b and R'c is hydrogen, alkyl or cycloalkyl, or alternatively $R°_3$ represents a radical —C≡C-Rd wherein Rd is alkyl, phenyl, phenylalkyl, phenoxyalkyl, phenylthioalkyl, N-alkyl-N-phenylaminoalkyl, mono- or bicyclic heteroaryl, heteroarylalkyl, heteroaryloxyalkyl, heteroarylthioalkyl, the heteroaryl parts mentioned above being mono- or bicyclic, wherein the phenyl, benzyl, benzoyl or heteroaryl radicals or portions are optionally substituted as disclosed in claim 1, and the compound is optionally enantiomeric or diastereoisomeric forms, or mixtures of these forms, or optionally in a syn or an anti form or mixtures thereof, or its salts.

4. The compound of claim 1 which is selected from the group consisting of:

1-[(2E)-3-(2,5-difluorophenyl)-2-propenyl]-3-[3-(3-fluoro-6-methoxyquinolin-4-yl)propyl]-3-pyrrolidinecarboxylic acid;

1-[(2E)-3-(2,5-difluorophenyl)-2-propenyl]-3-[3-hydroxy-(3-fluoro-6-methoxyquinolin-4-yl)propyl]-3-pyrrolidinecarboxylic acid;

1-[2-(2,5-difluorophenylsulfanyl)ethyl]-3-[3-(3-fluoro-6-methoxyquinolin-4-yl)propyl]-3-pyrrolidinecarboxylic acid;

1-[2-(2,5-difluorophenyloxy)ethyl]-3-[3-(3-fluoro-6-methoxyquinolin-4-yl)propyl]-3-pyrrolidinecarboxylic acid;

1-[2-(thiophen-2-ylsulfanyl)ethyl]-3-[3-(3-fluoro-6-methoxyquinolin-4-yl)propyl]-3-pyrrolidinecarboxylic acid;

1-[(2E)-3-(2,5-difluorophenyl)-2-propenyl]-3-[3-(3-fluoro-6-methoxyquinolin-4-yl)propyl]azetidine-3-carboxylic acid;

1-[(2E)-3-(2,5-difluorophenyl)-2-propenyl]-3-[3-hydroxy-(3-fluoro-6-methoxyquinolin-4-yl)propyl]azetidine-3-carboxylic acid;

1-[(2E)-3-(2,5-difluorophenyl)-2-propenyl]-3-[3-(3-chloro-6-methoxyquinolin-4-yl)propyl]-3-pyrrolidinecarboxylic acid;

1-[(2E)-3-(2,5-difluorophenyl)-2-propenyl]-3-[3-hydroxy-(3-chloro-6-methoxyquinolin-4-yl)propyl]-3-pyrrolidinecarboxylic acid;

1-[2-(2,5-difluorophenylsulfanyl)ethyl]-3-[3-(3-chloro-6-methoxyquinolin-4-yl)propyl]-3-pyrrolidinecarboxylic acid;

1-[2-(2,5-difluorophenyloxy)ethyl]-3-[3-(3-chloro-6-methoxyquinolin-4-yl)propyl]-3-pyrrolidinecarboxylic acid;

1-[2-(thiophen-2-ylsulfanyl)ethyl]-3-[3-(3-chloro-6-methoxyquinolin-4-yl)propyl]-3-pyrrolidinecarboxylic acid;

1-[(2E)-3-(2,5-difluorophenyl)-2-propenyl]-3-[3-(3-fluoro-6-methoxyquinolin-4-yl)-3-hydroxypropyl]-3-pyrrolidinecarboxylic acid;

3-[3-(3-chloro-6-methoxyquinolin-4-yl)]-3-hydroxypropyl]-1-[(2E)-3-2,5-difluorophenyl)-2-propenyl]-3-pyrrolidinecarboxylic acid;

1-[3-(2,5-difluorophenyl)propyl]-3-[3-(3-fluoro-6-methoxyquinolin-4-yl)-3-hydroxypropyl]-3-pyrrolidinecarboxylic acid, and 1-[2-[(2,5-difluorophenyl)thio]ethyl]-3-[3-(3-fluoro-6-methoxyquinolin-4-yl)-3-hydroxypropyl]-3-pyrrolidinecarboxylic acid;

wherein the compound is optionally in an enantiomeric or a diastereoisomeric form or mixtures of these forms, or optionally in a syn or an anti form or mixtures thereof, or its salts.

5. A process for preparing a compound of formula (I) as defined in claim 1 comprising:

reacting a 4 substituted quinoline of the formula (II)

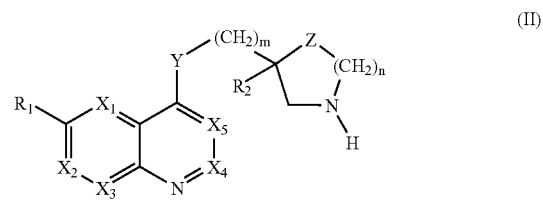

(II)

wherein $X_1$, $X_2$, $X_3$, $X_4$, $X_5$, $R_1$, $R_2$, Y, Z, m and n are as defined in claim 1, wherein $R_2$ is protected when it carries a carboxyl radical, with a compound of formula (IIa)

$R_3$—X     (IIa)

wherein $R_3$ is as defined for formula (I) in claim 1 and X is halogen, a methylsulfonyl, trifluoromethylsulfonyl or p-toluenesulfonyl;

removing the carboxyl protecting group, if necessary, to produce the compound of formula (I) as defined in claim 1;

optionally separating the enantiomers or diastereomers of formula (I);

optionally separating the syn and anti forms of formula (I); and optionally converting the compound of formula (1) into a pharmaceutically acceptable salt.

6. The process according to claim 5 wherein $R_3$ is alk-$R^o_3$, wherein alk is an alkyl radical, and $R^o_3$ is —C≡C-Rd, wherein Rd is as defined in claim 1 comprising:

reacting a compound of formula (II) with an alkynyl compound of formula HC≡C-alk-X, wherein alk is as defined above and X is halogen to give a compound of formula (I) wherein $R_3$ is HC≡C-alk-; and substituting the compound of formula (I) wherein $R_3$ is HC≡C-alk-, with an appropriate radical Rd, to give the compound of formula (I) wherein $R_3$ is Rd-C≡C-alk-.

7. The process according to claim 5 wherein $R_3$ is -alk-$R^o_3$, wherein alk is an alkyl radical, and $R^o_3$ is phenoxy, phenylthio, phenylamino, heteroaryloxy, heteroarylthio or heteroarylamino, comprising:

condensing a chain of formula HO-alk-X wherein X is halogen with a compound of formula (II) to produce a compound of formula (I) wherein $R_3$ is OH-alk-;

optionally converting the compound of formula (I) wherein $R_3$ is OH-alk- to the compound of formula (I) wherein $R_3$ is methanesulfonyl-alk-, halogen-alk- or p-toluenesulfonyl-alk-; and reacting the compound of the previous step with an aromatic compound having the formula $R^o_3$H or $R^o_3$H$_2$ wherein said aromatic compound acts as basic reaction medium or optionally reacting directly said aromatic compound with a compound produced in the first condensing reaction under dehydration conditions.

8. The process according to claim 5 for preparing compound of formula (I) wherein $R_3$ is hydroxymethyl or hydroxyethyl further comprising:

reducing a compound of formula (I) wherein $R_2$ is selected from the group consisting of either carboxyl, protected carboxyl, carboxymethyl and protected carboxymethyl.

9. The process according to claim 5 for preparing the compound of formula (II), wherein Y is a group CHR comprising:

condensing a compound of formula (III)

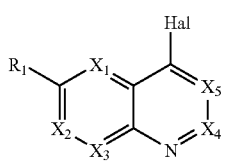

(III)

wherein $R_1$, $X_1$, $X_2$, $X_3$, $X_4$ and $X_5$ are as defined in claim 1 and Hal is halogen, with compound of formula (IV)

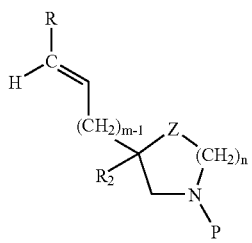

(IV)

wherein P is a protecting group and R, Z, m, n and $R_2$ are as defined in claim 1 or $R_2$ represents a protected radical if $R_2$ represents or carries a carboxylic acid functional group;

removing the protecting groups;

optionally converting the substituents of the aromatic bicycle of formula (II) thus obtained, to give the expected compound substituted with $R_1$, $R'_1$, $R'_2$, $R'_3$, $R'_4$, $R'_5$; and optionally removing any remaining protecting groups to give compound of formula (II) wherein R is CHR.

10. The process according to claim 9 for preparing compound of formula (IV) wherein R, Z, P, $R_2$ and n are as defined in claim 9 and m is equal to 2 or 3 comprising:

reacting a compound of formula (V)

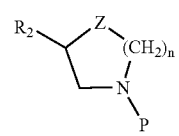

(V)

wherein Z and $R_2$ are as defined in claim 1 and P is a protecting group, with a compound of formula (VI)

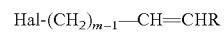

Hal-(CH$_2$)$_{m-1}$—CH=CHR  (VI)

wherein Hal is halogen and m and R are as defined in claim 1.

11. The process according to claim 9 for preparing a compound of formula (IV) wherein R, Z, P, $R_2$ and n are as defined in claim 9 and m is equal to 1, comprising:

reacting a compound of formula (V)

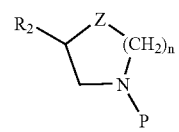

(V)

wherein Z and $R_2$ are as defined above and P is a protecting group, with a compound of formula (VI')

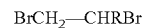

BrCH$_2$—CHRBr  (VI')

wherein R is as defined above; and removing the hydrobromide from the product to obtain compound of formula (IV) wherein R, Z, P, $R_2$ and n are as defined in claim 9 and m is equal to 1.

12. A compound of formula (II)

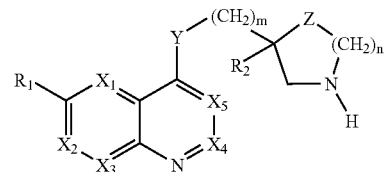

(II)

wherein $X_1$, $X_2$, $X_3$, $X_4$ and $X_5$ is C—$R'_1$ to C—$R'_5$ respectively, or alternatively at most one of them is a nitrogen atom, wherein $R_1$, $R'_1$, $R'_2$, $R'_3$, $R'_4$ and $R'_5$ are identical or different from one another and represent a hydrogen or halogen atom or an alkyl, cycloalkyl, phenyl, phenylthio, mono- or bicyclic heteroaryl or heteroarylthio, OH, SH, alkyloxy, difluoromethoxy, trifluoromethoxy, alkylthio, trifluoromethylthio, cycloalkyloxy, cycloalkylthio, acyl, acyloxy, acylthio, cyano, carboxyl, alkyloxycarbonyl, cycloalkyloxycarbonyl, nitro, —NRaRb or —CONRaRb radical (for which Ra and Rb can represent hydrogen, alkyl, cycloalkyl, phenyl, mono- or bicyclic heteroaryl or Ra and Rb form together with the nitrogen atom to which they are attached a 5- or 6-membered heterocycle which may optionally contain another heteroatom chosen from O, S and N and carrying, where appropriate, an alkyl, phenyl or mono- or bicyclic heteroaryl substituent on the nitrogen atom or, wherein the sulfur atom is oxidized to the sulfinyl or sulfonyl state, or methylene substituted with fluoro, hydroxyl, alkyloxy, alkylthio, cycloalkyloxy, cycloalkylthio, phenyl, mono- or bicyclic heteroaryl, carboxyl, alkyloxycarbonyl, cycloalkyloxycarbonyl, —NRaRb or —CONRaRb wherein Ra and Rb are as defined above, or is phenoxy, heterocyclyloxy, benzyloxy, heterocyclylmethyloxy, or alternatively $R_1$ may also be difluoromethoxy, or a radical having the structure —$C_pF_{2p+1}$, —$SC_pF_{2p+1}$ or —$OC_pF_{2p+1}$ wherein p is an integer from 1 to 6 or alternatively R'$_5$ may also be trifluoroacetyl, m is equal to 1, 2 or 3;

n is equal to 0, 1 or 2;

Y is CHR, CO, CROH, CRNH$_2$, CRF or CF$_2$, wherein R is hydrogen atom or alkyl ($C_{1-6}$);

Z is CH$_2$, oxygen, sulfur, SO, or SO$_2$ and, in this case, n is equal to 2; and $R_2$ is —CO$_2$R, —CH$_2$CO$_2$R, —CH$_2$—CH$_2$CO$_2$R, —CH$_2$OH or —CH$_2$—CH$_2$OH, wherein R is as defined above.

13. A method for the treatment or prophylaxis of bacterial infections comprising administering to a patient in need of said treatment an effective amount of a compound according to claim 1 or a pharmacologically tolerable salt thereof.

14. A pharmaceutical composition, or a pharmacologically tolerable salt thereof comprising a compound of claim 1, in the pure state or in combination with one or more compatible and pharmaceutically acceptable diluents or adjuvants.

15. The compound of general formula (I), as defined in claim 1, wherein Y is selected to be CROH, wherein R is a hydrogen atom or an alkyl ($C_{1-6}$) radical.

16. The compound of general formula (I), as defined in claim 1, wherein $X_1$, $X_2$, $X_3$, $X_4$ and $X_5$ are as defined in claim 1, $R_1$, R'$_1$, R'$_2$, R'$_3$, R'$_4$ ands R'$_5$, which are identical or different, are selected from hydrogen, halogen, alkyl, alkyloxy, or a methylene substituted with alkyloxy:

Y represents a species selected from CH$_2$, CHF, CHNH$_2$, C═O, or CROH, wherein R is a hydrogen or an alkyl ($C_{1-6}$ radical);

m is equal to 2;

n is as defined in claim 1;

Z is a CH$_2$ group or oxygen and in the latter case, n is equal to 2;

$R_2$ is as defined in claim 1, and $R_3$ is alk-$R°_3$ wherein alk is an alkylene radical and $R°_3$ is alkyloxy, alkylthio, alkylamino, dialkylamino, cycloalkyloxy, cycloalkylthio, cycloalkylamino, N-cycloalkyl-N-alkylamino, —N-(cycloalkyl)$_2$, phenoxy, phenylthio, phenylamino, N-alkyl-N-phenylamino, N-cycloalkyl-N-phenylamino, phenylalkyloxy, phenylalkylthio, phenylalkylamino, N-alkyl-N-phenylaminoalkyl, N-cycloalkyl-N-phenylalkylamino, heteroaryloxy, heteroarylthio, heteroarylamino, N-alkyl-N-heteroarylamino, N-cycloalkyl-N-heteroarylamino, heteroarylcarbonyl, heteroarylalkyloxy, heteroarylalkylthio, heteroarylalkylamino, N-alkyl-N-heteroarylaminoalkyl, N-cycloalkyl-N-heteroarylaminoalkyl, —NRaRb or —CO—NRaRb wherein Ra and Rb are as defined in claim 1, or alternatively $R°_3$ represents —CR'b═CR'c-R'a for which R'a represents phenyl, phenylalkyl, heteroaryl or heteroarylalkyl, phenoxyalkyl, phenylthioalkyl, phenylaminoalkyl, N-alkyl-N-phenylaminoalkyl, heteroaryloxyalkyl, heteroarylthioalkyl, heteroarylaminoalkyl, N-alkyl-N-heteroarylaminoalkyl, heteroarylthio, or phenylthio, and for which R'b and R'c is hydrogen, alkyl or cycloalkyl, or alternatively $R°_3$ is a radical —C≡C-Rd wherein Rd is alkyl, phenyl, phenylalkyl, phenoxyalkyl, phenylthioalkyl, N-alkyl-N-phenylaminoalkyl, mono- or bicyclic heteroaryl, heteroarylalkyl, heteroaryloxyalkyl, heteroarylthioalkyl, heteroarylaminoalkyl, N-alkyl-N-heteroarylaminoalkyl, or alternatively $R°_3$ is a radical —CF$_2$-phenyl or —CF$_2$-heteroaryl, wherein the phenyl, benzyl, benzoyl or heteroaryl radicals or portions thereof are optionally substituted as set forth in claim 1, and wherein the compound includes enantiomeric or diastereoisomeric forms or mixtures of these forms, or alternately a syn or an anti form of the compound or mixtures thereof, or its salts.

* * * * *